US010239882B2

(12) United States Patent
Allan et al.

(10) Patent No.: US 10,239,882 B2
(45) Date of Patent: Mar. 26, 2019

(54) SUBSTITUTED 5-METHYL-[1,2,4]
TRIAZOLO[1,5-A]PYRIMIDIN-2-AMINE
COMPOUNDS AS PDE2 INHIBITORS

(71) Applicant: DART NEUROSCIENCE (CAYMAN) LTD., Grand Cayman (KY)

(72) Inventors: Amy Lynn Allan, Encinitas, CA (US); James Breitenbucher, Escondido, CA (US); Laurent Gomez, San Diego, CA (US); Terence Patrick Keenan, San Diego, CA (US); Robert Lemus, Escondido, CA (US); Kiev Ly, San Diego, CA (US); Tami Jo Marrone, Carlsbad, CA (US)

(73) Assignee: DART NEUROSCIENCE (CAYMAN) LTD., Grand Cayman (KY)

( * ) Notice: Subject to any disclaimer, the term of this patent is extended or adjusted under 35 U.S.C. 154(b) by 0 days.

(21) Appl. No.: 15/524,586

(22) PCT Filed: Nov. 3, 2015

(86) PCT No.: PCT/US2015/058749
§ 371 (c)(1),
(2) Date: May 4, 2017

(87) PCT Pub. No.: WO2016/073424
PCT Pub. Date: May 12, 2016

(65) Prior Publication Data
US 2018/0282338 A1 Oct. 4, 2018

Related U.S. Application Data

(60) Provisional application No. 62/075,764, filed on Nov. 5, 2014.

(51) Int. Cl.
| *C07D 487/04* | (2006.01) |
| *A61K 31/519* | (2006.01) |
| *A61P 25/16* | (2006.01) |
| *A61P 25/18* | (2006.01) |
| *A61P 25/22* | (2006.01) |
| *A61P 25/24* | (2006.01) |
| *A61P 25/28* | (2006.01) |
| *A61P 25/02* | (2006.01) |
| *A61P 31/04* | (2006.01) |
| *A61P 29/00* | (2006.01) |
| *A61P 7/00* | (2006.01) |
| *A61P 9/00* | (2006.01) |
| *A61P 17/00* | (2006.01) |
| *A61P 3/04* | (2006.01) |
| *A61P 25/00* | (2006.01) |

(52) U.S. Cl.
CPC ............ *C07D 487/04* (2013.01); *A61P 25/00* (2018.01)

(58) Field of Classification Search
CPC ................................ C07D 487/04; A61P 25/00
USPC ......................................................... 514/259.3
See application file for complete search history.

(56) References Cited

U.S. PATENT DOCUMENTS

| 4,447,438 A | 5/1984 | Ledelec et al. |
| 4,938,949 A | 7/1990 | Borch et al. |
| 5,478,825 A | 12/1995 | Reiter et al. |
| 6,573,263 B2 | 6/2003 | Niewöhner et al. |
| 6,998,402 B2 | 2/2006 | Niewöhner et al. |
| 7,410,963 B2 | 8/2008 | Abarghaz et al. |
| 7,671,050 B2 | 3/2010 | Schmidt et al. |
| 7,851,472 B2 | 12/2010 | Schmidt et al. |
| 7,868,015 B2 | 1/2011 | Tully et al. |
| 7,947,731 B2 | 5/2011 | Tully et al. |
| 8,106,047 B2 | 1/2012 | Schmidt et al. |
| 8,598,155 B2 | 12/2013 | Helal et al. |
| 9,932,345 B2 * | 4/2018 | Breitenbucher ..... C07D 519/00 |

(Continued)

FOREIGN PATENT DOCUMENTS

| WO | WO 2002/064211 | 8/2002 |
| WO | WO 2004/044234 | 5/2004 |

(Continued)

OTHER PUBLICATIONS

Gomez; Bioorganic & Medicinal Chemistry Letters 23 (2013) 6522-6527. (Year: 2013).*
CAS Database Registry Nos. 2012:1381754-80-8; 1381750-79-3; 1381747-28-9; 1381743-97-0; "Methanone, . . . "; Entered Jul. 5, 2012; 2 pages.
CAS Database Registry Nos. 2010:1240215-31-9; 1240208-98-3; 1240201-99-3; 1240195-90-7; 1240195-65-6; 1340181-24-1; 1240169-61-2; 1240166-99-7; 1240166-22-6; 1240153-22-3; 1240128-18-0; 1240115-42-7; 1240102-95-7; 1240093-87-1; 1240091-60-4; "Methanone, . . . "; Entered Sep. 7/8, 2010; 8 pages.
CAS Database Registry Nos. 2010:1214610-92-0; 1214601-85-0; 1214591-56-6; 1214486-88-0; 1214427-36-7; "Methanone, . . . "; Entered Mar. 25, 2010; 3 pages.

(Continued)

*Primary Examiner* — Daniel R Carcanague
(74) *Attorney, Agent, or Firm* — Knobbe Martens Olson & Bear LLP

(57) ABSTRACT

The invention provides a chemical entity of Formula (I): (I), wherein $R^1$, $R^2$, $R^3$, and $R^4$, have any of the values described herein, and compositions comprising such chemical entities; methods of making them; and their use in a wide range of methods, including metabolic and reaction kinetic studies; detection and imaging techniques; radioactive treatments; modulating and treating disorders mediated by PDE2 activity; treating neurological disorders, CNS disorders, dementia, neurodegenerative diseases, and trauma-dependent losses of function; treating stroke, including cognitive and motor deficits during stroke rehabilitation; facilitating neuroprotection and neurorecovery; enhancing the efficiency of cognitive and motor training; and treating peripheral disorders, including hematological, cardiovascular, gastroenterological, and dermatological disorders.

20 Claims, No Drawings

(56) References Cited

U.S. PATENT DOCUMENTS

| | | |
|---|---|---|
| 2007/0112006 A1 | 5/2007 | Schiemann et al. |
| 2008/0188525 A1 | 8/2008 | Hallam et al. |
| 2009/0053140 A1 | 2/2009 | Scott et al. |
| 2011/0082137 A1 | 4/2011 | Giovannini et al. |
| 2012/0214791 A1 | 8/2012 | Helal et al. |
| 2017/0057967 A1 | 3/2017 | Breitenbucher et al. |
| 2018/0179216 A1* | 6/2018 | Breitenbucher ..... C07D 519/00 |

FOREIGN PATENT DOCUMENTS

| | | |
|---|---|---|
| WO | WO 2004/108136 | 12/2004 |
| WO | WO 2005/041957 | 5/2005 |
| WO | WO 2005/054246 | 6/2005 |
| WO | WO 2008/117943 | 10/2008 |
| WO | WO 2009/152825 | 12/2009 |
| WO | WO 2010/054253 | 5/2010 |
| WO | WO 2010/054260 | 5/2010 |
| WO | WO 2011/011312 | 1/2011 |
| WO | WO 2012/080729 | 6/2012 |
| WO | WO 2012/104293 | 8/2012 |
| WO | WO 2012/114222 | 8/2012 |
| WO | WO 2012/168817 | 12/2012 |
| WO | WO 2013/000924 | 1/2013 |
| WO | WO 2013/034755 | 3/2013 |
| WO | WO 2013/034758 | 3/2013 |
| WO | WO 2013/034761 | 3/2013 |
| WO | WO 2015/164508 | 4/2015 |

OTHER PUBLICATIONS

CAS Database Registry Nos. 2007:958707-04-5; 958706-09-7; 958706-04-2; 958618-14-9; 958596-27-5; 958586-25-9; 958585-88-1; 958583-82-9; 958583-78-3; "Methanone structures"; Entered Dec. 18/19, 2007; 6 pages.

International Search Report and Written Opinion dated Dec. 21, 2015 for International Application No. PCT/US2015/058749, filed Nov. 3, 2015.

* cited by examiner

SUBSTITUTED 5-METHYL-[1,2,4]TRIAZOLO[1,5-A]PYRIMIDIN-2-AMINE COMPOUNDS AS PDE2 INHIBITORS

CROSS REFERENCE TO RELATED APPLICATIONS

Any and all priority claims identified in the Application Data Sheet, or any correction thereto, are hereby incorporated by reference under 37 CFR 1.57. For example, this application is a U.S. National Phase of International Application No. PCT/US2015/058749, filed on Nov. 3, 2015 and published on May 12, 2016 as WO 2016/073424, which claims the benefit of U.S. Provisional Application 62/075,764, filed on Nov. 5, 2014, which is incorporated herein by reference in its entirety.

BACKGROUND

Field

The present disclosure relates to the fields of chemistry and medicine. More specifically, the present disclosure relates to compounds and compositions that can inhibit PDE2 and are useful in various methods.

Description of the Related Technology

The mammalian phosphodiesterases (PDEs) are a group of closely related enzymes divided into 11 families (PDE1-11) based on substrate specificity, inhibitor sensitivity and more recently, on sequence homology. The 11 families are coded by 21 genes, providing several of the families with multiple members. All mammalian PDEs share a conserved catalytic domain located in the COOH-terminal portion of the protein. In GAF-containing PDEs, one or both GAFs can provide dimerization contacts. In addition, one of the GAFs in these PDEs provides for allosteric cGMP binding (PDE2, PDE5, PDE6, PDE11), allosteric cAMP binding (PDE10), and regulation of catalytic site functions (PDE2, PDE5, PDE6). The other families of PDEs have unique complements of various subdomains (UCR, NHR, PAS, membrane association) that contribute to regulation of activity. PDEs 1, 2, 3, and 4 are expressed in many tissues, whereas others are more restricted. Numerous studies have highlighted a role for PDEs generally in modulating intracellular signaling pathways that regulate many physiological processes, including those underling neural plasticity, cognition, and memory (Menniti et al, *Nat Rev Drug Discov.* 2006, 5, 660-670). In particular, PDEs play an important role in intracellular signal transduction pathways involving the cyclic nucleotides, cAMP and cGMP as second messengers. These cyclic nucleotides function as ubiquitous intracellular signaling molecules in all mammalian cells. PDE enzymes hydrolyze cAMP and cGMP by breaking phosphodiester bonds to form the corresponding monophosphates (Bender and Beavo, *Pharmacol. Rev.,* 2006, 58(3), 488-520). PDE activities are modulated in coordination with adenylyl cyclase (AC) and guanylyl cyclase (GC) activities through direct effectors and feedback pathways, thereby maintaining cAMP and cGMP levels within optimum ranges for responsiveness to signals. The ability of extracellular signals to modulate the intracellular concentration of cyclic nucleotides allows cells to respond to external stimuli across the boundary of the cell membrane.

The cyclic nucleotide signaling cascades have been adapted to respond to a host of transduction systems, including G-protein coupled receptors (GPCRs) and voltage and ligand gated ion channels. Cyclic nucleotides transmit their signals in the cell through a variant of tertiary elements. The best described of these are cAMP dependent protein kinase (PKA) and cGMP dependent protein kinase (PKG). The binding of the cyclic nucleotide to each enzyme enables the phosphorylation of downstream enzymes and proteins functioning as effectors or additional elements in the signaling cascade. Of particular importance to memory formation is cAMP activation of PKA which phosphorylates cAMP response element-binding protein (CREB). Phosphorylated CREB is an activated transcription factor that binds to specific DNA loci and initiates transcription of multiple genes involved in neuronal plasticity. Both in vitro and in vivo studies have associated alterations in cyclic nucleotide concentrations with biochemical and physiological process linked to cognitive function (Kelly and Brandon, *Progress in Brain Research,* 2009, 179, 67-73; Schmidt, *Current Topics in Medicinal Chemistry,* 2010, 10, 222-230).

Signal intensity and the levels of coincident activity at a synapse are established variables that can result in potentiation of transmission at a particular synapse. Long term potentiation (LTP) is the best described of these processes and is known to be modulated by both the cAMP and cGMP signaling cascades. PDE2 inhibitors can enhance long term potentiation of synaptic transmission and can improve memory acquisition and consolidation in the object recognition and in the social recognition tests in rats. PDE2 inhibitors have shown activity in forced swim test and light/dark box models; and anxiolytic-like effects in elevated plus-maze, hole-board and open-field tests; and they can prevent stress-induced changes in apoptosis and behaviour (Boess et al., *Neuropharmacology,* 2004, 47, 1081-92; Masood et al., *J. Pharmacol. Exp. Ther.* 2009, 331, 690-699). Additionally, a selective PDE2 inhibitor appears to be efficacious in the novel object recognition test, the social recognition test and the T-maze, an animal model of working memory (Rutten et al., *Eur. J. Neurosci.,* 2007, 558, 107-112). Moreover, PDE2 inhibitors appear beneficial in reducing oxidative stress-induced anxiety, supporting their use in treating anxiety in psychiatric disorders and neurodegenerative disorders that involve oxidative stress, such as Alzheimer's disease, Parkinson's disease and multiple sclerosis (Masood et al., *J. Pharmacol. Exp. Ther.* 2008, 326, 369-379).

Such observations highlight the interest in inhibiting PDEs, including PDE2, as a therapeutic target for numerous disorders and in cognitive enhancement.

However, there remains a need for effective PDE2 inhibitors with desirable pharmaceutical properties, such as potency, exposure, selectivity, and side effect profile. The present invention addresses these and other needs in the art by disclosing 5-methyl-[1,2,4]triazolo[1,5-a]pyrimidin-2-amine compounds as potent, selective, and well-tolerated PDE2 inhibitors.

SUMMARY

Some embodiments provide a chemical entity of Formula (I):

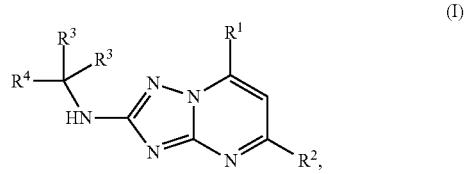

wherein $R^1$, $R^2$, $R^3$, and $R^4$ have any of the values described herein.

In one aspect the chemical entity is selected from the group consisting of, but not limited to, compounds of Formula (I) and all pharmaceutically acceptable forms thereof.

In certain embodiments, the compound of Formula (I) is a compound selected from those species described or exemplified in the detailed description herein.

Some embodiments provide pharmaceutical compositions for treating a disease, disorder, or medical condition mediated by PDE2 activity, comprising an effective amount of at least one chemical entity selected from compounds of Formula (1), pharmaceutically acceptable salts of compounds of Formula (I), pharmaceutically acceptable prodrugs of compounds of Formula (I), and pharmaceutically active metabolites of Formula (I).

In some embodiments, the pharmaceutical compositions may further comprise one or more pharmaceutically acceptable excipients.

Some embodiments provide a method of treating a subject suffering from or diagnosed with a disease, disorder, or condition mediated by PDE2 activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

Chemical entities of compounds of Formula (I) are useful in wide range of methods, as described herein. Isotopically-labeled compounds and prodrugs can be used in metabolic and reaction kinetic studies, detection and imaging techniques and radioactive treatments. In some aspects, the chemical entities of the present disclosure can be used to inhibit PDE2; to treat a disorder mediated by PDE2; to enhance neuronal plasticity; to treat neurological disorders, including neurodegenerative disorders, cognitive disorders, and cognitive deficits associated with CNS disorders; to confer neuroprotection; and to treat peripheral disorders, as disclosed herein. In some aspects, the chemical entities of the present disclosure are also useful as augmenting agents to enhance the efficiency of cognitive and motor training, including in stroke rehabilitation; to facilitate neurorecovery and neurorehabilitation; and to increase the efficiency of non-human animal training protocols. The invention is further directed to the general and specific embodiments defined, respectively, by the independent and dependent claims appended hereto, which are incorporated by reference herein.

Additional embodiments, features, and advantages of the disclosure will be apparent from the following detailed description and through practice of the exemplary embodiments.

DETAILED DESCRIPTION

The embodiments may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present embodiments.

Terms and Definitions

The use of headings and subheadings provided in the sections of this specification is solely for convenience of reference and does not limit the various embodiments herein, which are to be construed by reference to the specification as a while.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5-fold, or within 2-fold on either side of a value. Numerical quantities given herein are approximate unless stated otherwise, meaning that the term "about" or "approximately" can be inferred when not expressly stated.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

Furthermore, although items, elements or components of the embodiments may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. Thus, the term "example" is used to provide exemplary instances of the item in discussion, not an exhaustive or limiting list thereof. Similarly, adjectives such as "conventional," "traditional," "normal," "criterion," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to," or other like phrases in some instances should not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemical Terms

The term "alkyl" refers to a fully saturated aliphatic hydrocarbon group. The alkyl moiety may be a straight- or branched-chain alkyl group having from 1 to 12 carbon atoms in the chain.

Examples of alkyl groups include, but are not limited to, methyl (Me, which also may be structurally depicted by the symbol, "———"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, hydroxyl, alkoxy, thioalkoxy, amino, and aminoalkyl.

The term "haloalkyl" refers to a straight- or branched-chain alkyl group having from 1 to 12 carbon atoms in the chain, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl," "thioalkyl," and "sulfonylalkyl" are analogous to alkoxy, replacing the terminal oxygen atom of alkoxy with, respectively, NH (or NR), S, and $SO_2$.

The term "cyano" refers to the group —CN.

The term "aryl" refers to a monocyclic, or fused or spiro polycyclic, aromatic carbocycle (ring structure having ring atoms that are all carbon), having from 3 to 12 ring atoms per ring (carbon atoms in aryl groups are sp2 hybridized).

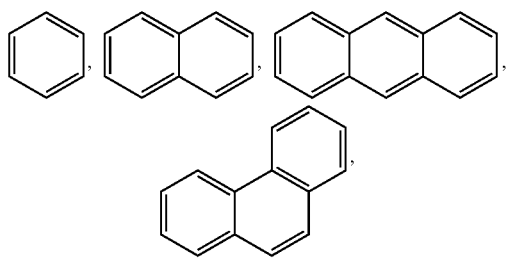

and the like.

The term "phenyl" represents the following moiety:

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

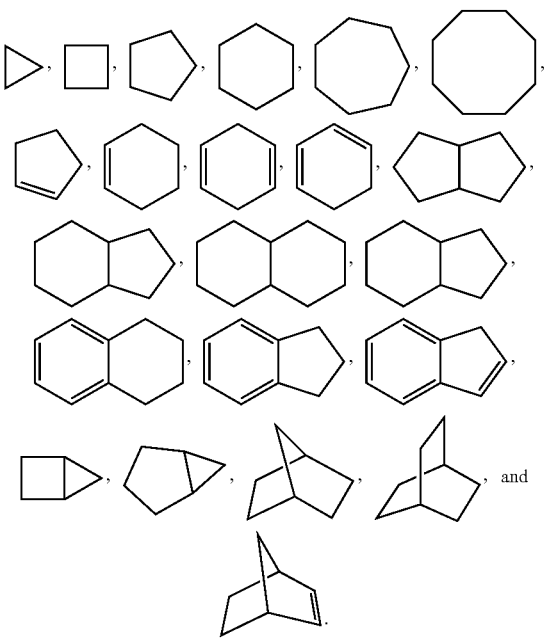

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

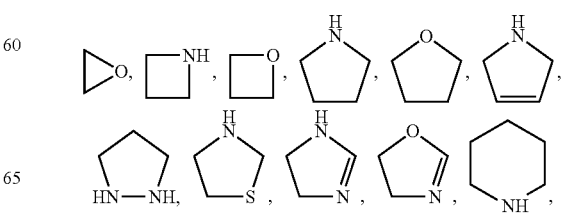

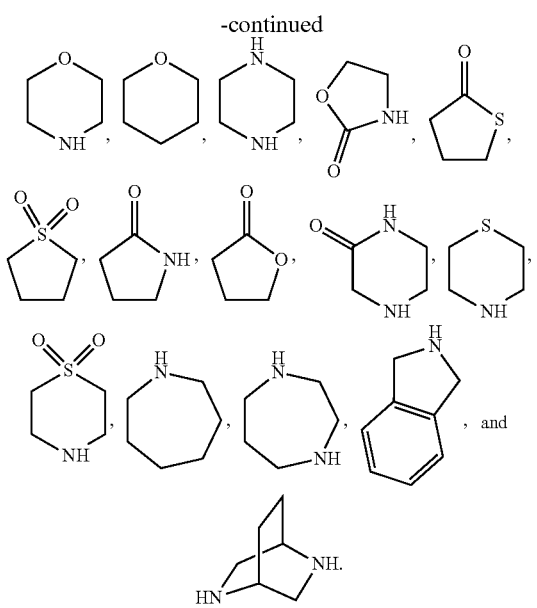

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

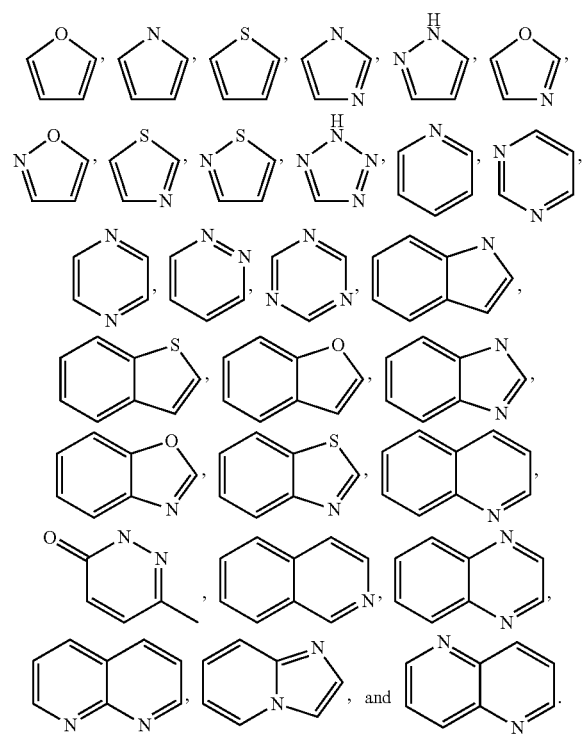

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

By "optional" or "optionally" is meant that the subsequently described event or circumstance may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted" used herein means that any one or more hydrogens on the designated atom or group is replaced with a selection from the indicated group, provided that the designated atom's normal valence is not exceeded. When a substituent is oxo (i.e., =O) then 2 hydrogens on the atom are replaced.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols —— and —◂ are used as meaning the same spacial arrangement in chemical structures shown herein. Analogously, the symbols ııııı and ⋯ııı are used as meaning the same spacial arrangement in chemical structures shown herein.

Chemical Entities

Generally

Chemical entities of the present embodiments include, but are not limited to, compounds of Formula (I) and all pharmaceutically acceptable forms thereof. Pharmaceutically acceptable forms of the compounds recited herein include pharmaceutically acceptable chelates, solvates, conformers, crystalline forms/polymorphs, salts, prodrugs, pharmaceutically active metabolites, and mixtures thereof. In certain embodiments, the compounds described herein are in the form of pharmaceutically acceptable salts. Hence, the terms "chemical entity" and "chemical entities" also encompass pharmaceutically acceptable chelates, solvates, conformers, crystalline forms/polymorphs, salts, prodrugs, pharmaceutically active metabolites, and mixtures.

The term "pharmaceutically acceptable," as used in connection with compositions of the embodiments, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

Chelates

The term "chelate" refers to the chemical entity formed by the coordination of a compound to a metal ion at two (or more) points.

Solvates

Additionally, any formula given herein is intended to refer also to hydrates, solvates, and polymorphs of such compounds, and mixtures thereof, even if such forms are not listed explicitly. Some embodiments provide a solvate of a compound of Formula (I), and the use of such solvates in methods described herein. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the embodiments with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as MeOH, methyl t-butyl ether, EtOAc, mEtOAc, (S)-propylene glycol, (R)-propylene glycol, 1,4-butyne-diol, and the like. Hydrates include compounds formed by an incorporation of one or more water molecules.

Conformers and Crystalline Forms/Polymorphs

Some embodiments provide conformer and crystalline forms of a compound of Formula (I), and the use of these entities in methods of present disclosure. A conformer is a structure that is a conformational isomer.

Conformational isomerism is the phenomenon of molecules with the same structural formula but different conformations (conformers) of atoms about a rotating bond.

A polymorph is a composition having the same chemical formula, but a different solid state or crystal structure. In certain embodiments, compounds of Formula (I) are obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in its chemically relevant form (or forms) that exists in the medium in which such reacting takes place, with (b) the chemically relevant form (or forms) of the compound R—COOH that exists in the medium in which such reacting takes place. In this regard, if such entity is, for example, in an aqueous environment, it is understood that the compound R—COOH is in the same such medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but is merely an illustration. It is understood that analogous examples can be provided in terms of other functional groups, including, but not limited to, hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that may form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts".

Salts

Embodiments include pharmaceutically acceptable salts of the compounds represented by Formula (I), and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methane-sulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Prodrugs

Some embodiments provide prodrugs of the compounds of Formula (I), and the use of such pharmaceutically acceptable prodrugs in methods of the present disclosure, particularly therapeutic methods.

A "prodrug" is a drug precursor that is initially inactive or partially active and upon administration in vivo undergoes chemical conversion by metabolic processes into an active pharmacological agent. A "pharmaceutically acceptable prodrug" is a prodrug that is preferably non-toxic, biologically tolerable, and otherwise biologically suitable for administration to the subject. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters include $C_{1-6}$alkyl, $C_{1-6}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy) methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

Some embodiments provide pharmaceutically active metabolites of the compounds of Formula (I), which may also be used in the methods of the disclosure. A "pharmaceutically active metabolite" means a pharmacologically active product of metabolism in the body of a compound of Formula (I) or salt thereof.

Prodrugs and active metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, *Drug Dev. Res.* 1995, 34, 220-230; and Bodor, *Adv Drug Res.* 1984, 13, 224-231).

Isotopes

Isotopes may be present in the compounds described. Each chemical element present in a compound either specifically or generically described herein may include any isotope of the element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present embodiments encompass any composition made by admixing a compound of Formula (I) and a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

The term "carrier" refers to an adjuvant, vehicle, or excipients, with which the compound is administered. In preferred embodiments, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refers to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" refers to a sterile, pharmaceutical product produced under good manufacturing practices (GMP) that is prepared and presented in a manner such that the composition not likely to cause any untoward or deleterious effects when orally administered to a subject. Unless specified otherwise, all of the compositions disclosed herein are suitable for oral administration.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the embodiments, "an effective amount" of at least one compound according to the embodiments is administered to a subject (e.g., a mammal). An "effective amount" also means an amount or dose of a compound or composition effective to modulate activity of PDE2 or an associated signaling pathway. The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present embodiments are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to the embodiments of the present disclosure, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Chemical Entities

Some embodiments provide certain substituted 5-methyl-[1,2,4]triazolo[1,5-a]pyrimidin-2-amine derivatives, which are useful, for example, as inhibitors of PDE2 enzymatic activity.

In certain embodiments of Formula (I), $R^1$ is —$C_{3-6}$ branched alkyl unsubstituted or substituted with one or more members selected from halo and —$C_{1-4}$alkoxy. In certain embodiments of Formula (I), $R^1$ is —$C_{3-6}$cycloalkyl unsubstituted or substituted with one or more members selected from halo and —$C_{1-4}$alkyl. In certain embodiments of Formula (I), $R^1$ is carbon-linked heterocycloalkyl selected from oxolan-2-yl, oxolan-3-yl, oxan-3-yl, oxan-4-yl, -3,6-dihydro-2H-pyran-4-yl, and piperidin-4-yl each unsubstituted or substituted with halo, —$C_{1-4}$alkyl, or —C(=O)CH$_3$.

In some embodiments, $R^1$ is -isopropyl, -tert-butyl, 2-methoxypropan-2-yl, -butan-2-yl, cyclopropyl, 1-methylcyclopropyl, cyclobutyl, cyclopentyl, 4,4-difluorocyclohexyl, oxolan-2-yl, oxolan-3-yl, oxan-3-yl, -4-methyloxan-4-yl, 4-fluorooxan-4-yl, -3,6-dihydro-2H-pyran-4-yl, -oxan-4-yl, or 1-acetyl-piperidin-4-yl In some embodiments, $R^2$ is —$C_{1-6}$alkyl, —$C_{1-6}$haloalkyl, or -cyclopropyl.

In some embodiments, $R^2$ is —CH$_3$, —CHF$_2$, —CH$_2$F, —CF$_3$, or -cyclopropyl.

In some embodiments, $R^3$ is independently —H or —CH$_3$.

In some embodiments, $R^4$ is phenyl substituted with one, two, three or four $R^a$ members independently selected from —$C_{1-6}$alkyl, —$C_{1-6}$haloalkyl, —OC$_{1-6}$alkyl, —CN, —Br, —Cl, —F, or optionally two $R^a$ members come together to form a cyclopentyl, furan, dioxane, or 2,2-difluorodioxolane ring.

In some embodiments, each $R^a$ is independently —$C_{1-6}$alkyl, —$C_{1-6}$haloalkyl, —OCH$_3$, —CN, —Br, —Cl, or —F.

In some embodiments, $R^4$ is 2,2-difluoro-2H-1,3-benzodioxol-5-yl, 2,3-dihydro-1,4-benzodioxin-6-yl, 2,3-dihydro-1-benzofuran-5-yl, 2,3-dihydro-1-benzofuran-5-yl, 2,3-dihydro-1-benzofuran-6-yl, 2,3-dihydro-1H-inden-5-yl, 2,4-difluorophenyl, 2,5-difluorophenyl, 2,6-difluoro-4-methoxyphenyl, 2,6-difluorophenyl, 2-chlorophenyl, 2-fluoro-4-methoxyphenyl, 2-fluoro-5-methoxyphenyl, 2-fluoro-5-methylphenyl, 2-methylphenyl, 3,4-difluorophenyl, 3,5-difluorophenyl, 3-bromo-2-fluorophenyl, 3-bromo-5-fluorophenyl, 3-bromophenyl, 3-chloro-2,4-difluorophenyl, 3-chloro-4-methoxyphenyl, 3-chloro-5-fluorophenyl, 3-chlorophenyl, 3-cyanophenyl, 3-fluorophenyl, 3-methoxyphenyl, 3-methylphenyl, 3-trifluoromethylphenyl, 4-fluorobenzonitrile, 4-fluorophenyl, 4-methoxyphenyl, 5-chloro-2,4-difluorophenyl, 5-chloro-2-fluorophenyl, difluoromethyl-4-methoxyphenyl, difluoromethylphenyl, or phenyl.

In some embodiments, $R^4$ is (2,2-difluoroethyl)-3-methyl-1H-pyrazol-4-yl, 1-(2-methylphenyl)-1H-pyrazol-4-yl, 1-cyclopentyl-3-methyl-1H-pyrazol-4-yl, 1-methyl-3-(trifluoromethyl)-1H-pyrazol-5-yl, 1-methyl-3-phenyl-1H-pyrazol-5-yl, 1-phenyl-1H-pyrazol-4-yl, 2-(trifluoromethyl)pyridin-4-yl, 2,6-dimethylpyridin-4-yl, 2-methylpyridin-4-yl, 3,5-difluoropyridin-4-yl, 3-methyl-1-(propan-2-yl)-1H-pyrazol-4-yl, 3-methyl-1-phenyl-1H-pyrazol-4-yl, 3-phenyl-1,2-oxazol-5-yl, 4-methyl-2-phenyl-1,3-oxazol-5-yl, 5-methylpyridin-3-yl, difluoromethylpyridin-4-yl or quinolin-4-yl.

In certain embodiments of Formula (I), $R^2$ is —$C_{1-4}$alkyl and is $R^4$ is phenyl substituted with one, two, or three $R^a$ members independently selected from —$C_{1-6}$alkyl, —$C_{1-6}$haloalkyl, —OC$_{1-6}$alkyl, —Br, —Cl, or —F.

In certain embodiments of Formula (I), $R^1$ is an optionally substituted oxan-4-yl and $R^2$ is —$C_{1-4}$alkyl.

In certain embodiments of Formula (I), $R^3$ is —H and $R^4$ is 2,4-difluorophenyl, 2,5-difluorophenyl, 2,6-difluoro-4-methoxyphenyl, 2,6-difluorophenyl, 2-chlorophenyl, 2-fluoro-4-methoxyphenyl, 2-fluoro-5-methoxyphenyl, 2-fluoro-5-methylphenyl, 2-fluorophenyl, 2-methylphenyl, 3,4-difluorophenyl, 3,5-difluorophenyl, 3-bromo-2-fluorophenyl, 3-bromo-5-fluorophenyl, 3-bromophenyl, 3-chloro-2,4-difluorophenyl, 3-chloro-4-methoxyphenyl, 3-chloro-5-fluorophenyl, 3-chlorophenyl, 3-fluorophenyl, 3-methoxyphenyl, 3-methylphenyl, 3-trifluoromethylphenyl, 4-fluorophenyl, 4-methoxyphenyl, 5-chloro-2,4-difluorophenyl, 5-chloro-2-fluorophenyl, difluoromethyl-4-methoxyphenyl or difluoromethylphenyl.

In some embodiments, $R^1$ is an optionally substituted oxan-4-yl and $R^2$ is —CH$_3$.

In some embodiments, the chemical entity of Formula (I) has the structure of Formula (Ia):

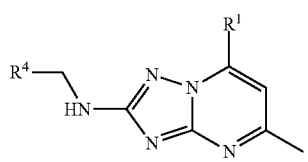

(Ia), wherein the chemical entity is selected from the group consisting of compounds of Formula (Ia), pharmaceutically acceptable salts of compounds of Formula (Ia), pharmaceutically acceptable prodrugs of compounds of Formula (Ia), and pharmaceutically active metabolites of compounds of Formula (Ia).

In certain embodiments, a compound, or pharmaceutically acceptable salt thereof, of Formula (I) is selected from the group consisting of:

| Example | Compound Name |
|---|---|
| 1 | N-[(4-Methoxyphenyl)methyl]-5-methyl-7-(oxan-4-yl)-[1,2,4]triazolo[1,5-a]pyrimidin-2-amine; |
| 2 | 7-Cyclopropyl-N-(2,3-dihydro-1-benzofuran-5-ylmethyl)-5-methyl-[1,2,4]triazolo[1,5-a]pyrimidin-2-amine; |
| 3 | 7-Cyclopropyl-N-(2,3-dihydro-1-benzofuran-6-ylmethyl)-5-methyl-[1,2,4]triazolo[1,5-a]pyrimidin-2-amine; |
| 4 | 7-Cyclopropyl-N-[(4-methoxyphenyl)methyl]-5-methyl-[1,2,4]triazolo[1,5-a]pyrimidin-2-amine; |
| 5 | 7-Cyclopentyl-N-(2,3-dihydro-1H-inden-5-ylmethyl)-5-methyl-[1,2,4]triazolo[1,5-a]pyrimidin-2-amine; |
| 6 | N-(2,3-Dihydro-1H-inden-5-ylmethyl)-5-methyl-7-(propan-2-yl)-[1,2,4]triazolo[1,5-a]pyrimidin-2-amine; |
| 7 | N-[(3-Chlorophenyl)methyl]-5-methyl-7-(propan-2-yl)-[1,2,4]triazolo[1,5-a]pyrimidin-2-amine; |
| 8 | N-Benzyl-5-methyl-7-(propan-2-yl)-[1,2,4]triazolo[1,5-a]pyrimidin-2-amine; |
| 9 | 7-tert-Butyl-N-[(3-chlorophenyl)methyl]-5-methyl-[1,2,4]triazolo[1,5-a]pyrimidin-2-amine; |
| 10 | N-[(4-Methoxyphenyl)methyl]-5-methyl-7-(propan-2-yl)-[1,2,4]triazolo[1,5-a]pyrimidin-2-amine; |
| 11 | 7-(Butan-2-yl)-N-[(4-methoxyphenyl)methyl]-5-methyl-[1,2,4]triazolo[1,5-a]pyrimidin-2-amine; |
| 12 | N-[(4-Methoxyphenyl)methyl]-5-methyl-7-(oxolan-2-yl)-[1,2,4]triazolo[1,5-a]pyrimidin-2-amine; |
| 13 | N-[(5-Chloro-2-fluorophenyl)methyl]-5-methyl-7-(oxan-4-yl)-[1,2,4]triazolo[1,5-a]pyrimidin-2-amine; |
| 14 | N-[(3,5-Difluorophenyl)methyl]-5-methyl-7-(oxan-4-yl)-[1,2,4]triazolo[1,5-a]pyrimidin-2-amine; |
| 15 | N-[(2-Fluoro-4-methoxyphenyl)methyl]-5-methyl-7-(oxan-4-yl)-[1,2,4]triazolo[1,5-a]pyrimidin-2-amine; |
| 16 | N-(2,3-Dihydro-1,4-benzodioxin-6-ylmethyl)-5-methyl-7-(oxan-4-yl)-[1,2,4]triazolo[1,5-a]pyrimidin-2-amine; |
| 17 | 5-Methyl-7-(oxan-4-yl)-N-[(1-phenyl-1H-pyrazol-4-yl)methyl]-[1,2,4]triazolo[1,5-a]pyrimidin-2-amine; |
| 18 | 1-[4-(2-{[(4-Methoxyphenyl)methyl]amino}-5-methyl-[1,2,4]triazolo[1,5-a]pyrimidin-7-yl)piperidin-1-yl]ethan-1-one; |
| 19 | 1-{4-[2-({[3-(Difluoromethyl)-4-methoxyphenyl]methyl}amino)-5-methyl-[1,2,4]triazolo[1,5-a]pyrimidin-7-yl]piperidin-1-yl}ethan-1-one; |
| 20 | 1-{4-[2-({[3-(Difluoromethyl)phenyl]methyl}amino)-5-methyl-[1,2,4]triazolo[1,5-a]pyrimidin-7-yl]piperidin-1-yl}ethan-1-one; |
| 21 | N-[(3-Chloro-4-methoxyphenyl)methyl]-5-methyl-7-(oxan-4-yl)-[1,2,4]triazolo[1,5-a]pyrimidin-2-amine; |
| 22 | 7-(4,4-Difluorocyclohexyl)-N-[(4-methoxyphenyl)methyl]-5-methyl-[1,2,4]triazolo[1,5-a]pyrimidin-2-amine; |
| 23 | N-{[3-(Difluoromethyl)phenyl]methyl}-5-methyl-7-(oxan-4-yl)-[1,2,4]triazolo[1,5-a]pyrimidin-2-amine; |
| 24 | N-[(3-Methoxyphenyl)methyl]-5-methyl-7-(oxan-4-yl)-[1,2,4]triazolo[1,5-a]pyrimidin-2-amine; |
| 25 | N-{[3-(Difluoromethyl)-4-methoxyphenyl]methyl}-5-methyl-7-(oxan-4-yl)-[1,2,4]triazolo[1,5-a]pyrimidin-2-amine; |
| 26 | N-[(2-Fluorophenyl)methyl]-5-methyl-7-(oxan-4-yl)-[1,2,4]triazolo[1,5-a]pyrimidin-2-amine; |
| 27 | N-[(2-Fluoro-5-methylphenyl)methyl]-5-methyl-7-(oxan-4-yl)-[1,2,4]triazolo[1,5-a]pyrimidin-2-amine; |
| 28 | 5-Methyl-N-[(3-methylphenyl)methyl]-7-(oxan-4-yl)-[1,2,4]triazolo[1,5-a]pyrimidin-2-amine; |
| 29 | 5-(Difluoromethyl)-N-[(4-methoxyphenyl)methyl]-7-(oxan-4-yl)-[1,2,4]triazolo[1,5-a]pyrimidin-2-amine; |
| 30 | 5-(Fluoromethyl)-N-[(4-methoxyphenyl)methyl]-7-(oxan-4-yl)-[1,2,4]triazolo[1,5-a]pyrimidin-2-amine; |
| 31 | N-{[1-(3-Methoxyphenyl)-1H-pyrazol-4-yl]methyl}-5-methyl-7-(oxan-4-yl)-[1,2,4]triazolo[1,5-a]pyrimidin-2-amine; |
| 32 | N-[(2-Fluoro-5-methoxyphenyl)methyl]-5-methyl-7-(oxan-4-yl)-[1,2,4]triazolo[1,5-a]pyrimidin-2-amine; |
| 33 | N-Benzyl-5-methyl-7-(oxan-4-yl)-[1,2,4]triazolo[1,5-a]pyrimidin-2-amine; |
| 34 | N-[(4-Methoxyphenyl)methyl]-5-methyl-7-(4-methyloxan-4-yl)-[1,2,4]triazolo[1,5-a]pyrimidin-2-amine; |
| 35 | 5-Methyl-N-[(2-methylpyridin-4-yl)methyl]-7-(oxan-4-yl)-[1,2,4]triazolo[1,5-a]pyrimidin-2-amine; |
| 36 | 5-Methyl-N-{[1-(2-methylphenyl)-1H-pyrazol-4-yl]methyl}-7-(oxan-4-yl)-[1,2,4]triazolo[1,5-a]pyrimidin-2-amine; |
| 37 | 5-Methyl-7-(oxan-4-yl)-N-[(3-phenyl-1,2-oxazol-5-yl)methyl]-[1,2,4]triazolo[1,5-a]pyrimidin-2-amine; |
| 38 | N-[(4-Methoxyphenyl)methyl]-5-methyl-7-(oxan-3-yl)-[1,2,4]triazolo[1,5-a]pyrimidin-2-amine; |
| 39 | N-[(3-Bromophenyl)methyl]-5-methyl-7-(oxan-4-yl)-[1,2,4]triazolo[1,5-a]pyrimidin-2-amine; |
| 40 | N-[(3-Chlorophenyl)methyl]-5-methyl-7-(oxan-4-yl)-[1,2,4]triazolo[1,5-a]pyrimidin-2-amine; |

-continued

| Example | Compound Name |
|---|---|
| 41 | 5-Methyl-7-(oxan-4-yl)-N-{[3-(trifluoromethyl)phenyl]methyl}-[1,2,4]triazolo[1,5-a]pyrimidin-2-amine; |
| 42 | N-(2,3-Dihydro-1-benzofuran-5-ylmethyl)-5-methyl-7-(oxan-4-yl)-[1,2,4]triazolo[1,5-a]pyrimidin-2-amine; |
| 43 | 5-Methyl-7-(4-methyloxan-4-yl)-N-[(2-methylpyridin-4-yl)methyl]-[1,2,4]triazolo[1,5-a]pyrimidin-2-amine; |
| 44 | N-[(4-Methoxyphenyl)methyl]-5-methyl-7-(oxolan-3-yl)-[1,2,4]triazolo[1,5-a]pyrimidin-2-amine; |
| 45 | N-[(2,2-Difluoro-2H-1,3-benzodioxol-5-yl)methyl]-5-methyl-7-(oxan-4-yl)-[1,2,4]triazolo[1,5-a]pyrimidin-2-amine; |
| 46 | 5-Methyl-N-[(3-methyl-1-phenyl-1H-pyrazol-4-yl)methyl]-7-(oxan-4-yl)-[1,2,4]triazolo[1,5-a]pyrimidin-2-amine; |
| 47 | 5-Methyl-N-[(2-methylphenyl)methyl]-7-(oxan-4-yl)-[1,2,4]triazolo[1,5-a]pyrimidin-2-amine; |
| 48 | N-[(2-Chlorophenyl)methyl]-5-methyl-7-(oxan-4-yl)-[1,2,4]triazolo[1,5-a]pyrimidin-2-amine; |
| 49 | N-[(2,5-Difluorophenyl)methyl]-5-methyl-7-(oxan-4-yl)-[1,2,4]triazolo[1,5-a]pyrimidin-2-amine; |
| 50 | N-[(2,6-Difluoro-4-methoxyphenyl)methyl]-5-methyl-7-(oxan-4-yl)-[1,2,4]triazolo[1,5-a]pyrimidin-2-amine; |
| 51 | N-[(2,6-Difluorophenyl)methyl]-5-methyl-7-(oxan-4-yl)-[1,2,4]triazolo[1,5-a]pyrimidin-2-amine; |
| 52 | N-{[2-(Difluoromethyl)pyridin-4-yl]methyl}-5-methyl-7-(oxan-4-yl)-[1,2,4]triazolo[1,5-a]pyrimidin-2-amine; |
| 53 | N-[(2,6-Dimethylpyridin-4-yl)methyl]-5-methyl-7-(oxan-4-yl)-[1,2,4]triazolo[1,5-a]pyrimidin-2-amine; |
| 54 | 5-Methyl-N-[(5-methylpyridin-3-yl)methyl]-7-(oxan-4-yl)-[1,2,4]triazolo[1,5-a]pyrimidin-2-amine; |
| 55 | 7-(4-Fluorooxan-4-yl)-N-[(4-methoxyphenyl)methyl]-5-methyl-[1,2,4]triazolo[1,5-a]pyrimidin-2-amine; |
| 56 | N-[(3,4-Difluorophenyl)methyl]-5-methyl-7-(oxan-4-yl)-[1,2,4]triazolo[1,5-a]pyrimidin-2-amine; |
| 57 | N-[(4-Fluorophenyl)methyl]-5-methyl-7-(oxan-4-yl)-[1,2,4]triazolo[1,5-a]pyrimidin-2-amine; |
| 58 | N-[(3-Fluorophenyl)methyl]-5-methyl-7-(oxan-4-yl)-[1,2,4]triazolo[1,5-a]pyrimidin-2-amine; |
| 59 | 5-Methyl-7-(oxan-4-yl)-N-{[2-(trifluoromethyl)pyridin-4-yl]methyl}-[1,2,4]triazolo[1,5-a]pyrimidin-2-amine; |
| 60 | 5-Methyl-7-(oxan-4-yl)-N-(quinolin-4-ylmethyl)-[1,2,4]triazolo[1,5-a]pyrimidin-2-amine; |
| 61 | 5-Methyl-N-[(3-methyl-1-phenyl-1H-pyrazol-4-yl)methyl]-7-(4-methyloxan-4-yl)-[1,2,4]triazolo[1,5-a]pyrimidin-2-amine; |
| 62 | 5-Methyl-7-(4-methyloxan-4-yl)-N-[(1-phenyl-1H-pyrazol-4-yl)methyl]-[1,2,4]triazolo[1,5-a]pyrimidin-2-amine; |
| 63 | 7-Cyclopropyl-5-methyl-N-[(3-methyl-1-phenyl-1H-pyrazol-4-yl)methyl]-[1,2,4]triazolo[1,5-a]pyrimidin-2-amine; |
| 64 | N-[(1R)-1-(4-Methoxyphenyl)ethyl]-5-methyl-7-(oxan-4-yl)-[1,2,4]triazolo[1,5-a]pyrimidin-2-amine; |
| 65 | N-{[1-(2,2-Difluoroethyl)-3-methyl-1H-pyrazol-4-yl]methyl}-5-methyl-7-(oxan-4-yl)-[1,2,4]triazolo[1,5-a]pyrimidin-2-amine; |
| 66 | 5-Methyl-N-{[3-methyl-1-(propan-2-yl)-1H-pyrazol-4-yl]methyl}-7-(oxan-4-yl)-[1,2,4]triazolo[1,5-a]pyrimidin-2-amine; |
| 67 | N-[(1-Cyclopentyl-3-methyl-1H-pyrazol-4-yl)methyl]-5-methyl-7-(oxan-4-yl)-[1,2,4]triazolo[1,5-a]pyrimidin-2-amine; |
| 68 | N-[(2,4-Difluorophenyl)methyl]-5-methyl-7-(oxan-4-yl)-[1,2,4]triazolo[1,5-a]pyrimidin-2-amine; |
| 69 | N-[(1S)-1-(4-Methoxyphenyl)ethyl]-5-methyl-7-(oxan-4-yl)-[1,2,4]triazolo[1,5-a]pyrimidin-2-amine; |
| 70 | N-[(3,5-Difluoropyridin-4-yl)methyl]-5-methyl-7-(oxan-4-yl)-[1,2,4]triazolo[1,5-a]pyrimidin-2-amine; |
| 71 | 7-Cyclobutyl-5-methyl-N-[(3-methyl-1-phenyl-1H-pyrazol-4-yl)methyl]-[1,2,4]triazolo[1,5-a]pyrimidin-2-amine; |
| 72 | 5-Methyl-N-[(3-methyl-1-phenyl-1H-pyrazol-4-yl)methyl]-7-(oxolan-3-yl)-[1,2,4]triazolo[1,5-a]pyrimidin-2-amine; |
| 73 | 4-Fluoro-3-({[5-methyl-7-(oxan-4-yl)-[1,2,4]triazolo[1,5-a]pyrimidin-2-yl]amino}methyl)benzonitrile |
| 74 | 5-Methyl-N-[(3-methyl-1-phenyl-1H-pyrazol-4-yl)methyl]-7-(propan-2-yl)-[1,2,4]triazolo[1,5-a]pyrimidin-2-amine; |
| 75 | N-[(4-Methoxyphenyl)methyl]-5-methyl-7-(1-methylcyclopropyl)-[1,2,4]triazolo[1,5-a]pyrimidin-2-amine; |
| 76 | 5-Methyl-N-[(3-methyl-1-phenyl-1H-pyrazol-4-yl)methyl]-7-(1-methylcyclopropyl)-[1,2,4]triazolo[1,5-a]pyrimidin-2-amine; |
| 77 | N-[(4-Methoxyphenyl)methyl]-7-(2-methoxypropan-2-yl)-5-methyl-[1,2,4]triazolo[1,5-a]pyrimidin-2-amine; |
| 78 | N-[(3-Chloro-2,4-difluorophenyl)methyl]-5-methyl-7-(oxan-4-yl)-[1,2,4]triazolo[1,5-a]pyrimidin-2-amine; |

-continued

| Example | Compound Name |
|---|---|
| 79 | 5-Methyl-N-[(4-methyl-2-phenyl-1,3-oxazol-5-yl)methyl]-7-(oxan-4-yl)-[1,2,4]triazolo[1,5-a]pyrimidin-2-amine; |
| 80 | N-[(5-Chloro-2,4-difluorophenyl)methyl]-5-methyl-7-(oxan-4-yl)-[1,2,4]triazolo[1,5-a]pyrimidin-2-amine; |
| 81 | N-[(3-Bromo-5-fluorophenyl)methyl]-5-methyl-7-(oxan-4-yl)-[1,2,4]triazolo[1,5-a]pyrimidin-2-amine; |
| 82 | 5-Methyl-N-[(1-methyl-3-phenyl-1H-pyrazol-5-yl)methyl]-7-(oxan-4-yl)-[1,2,4]triazolo[1,5-a]pyrimidin-2-amine; |
| 83 | N-[(3-Bromo-2-fluorophenyl)methyl]-5-methyl-7-(oxan-4-yl)-[1,2,4]triazolo[1,5-a]pyrimidin-2-amine; |
| 84 | N-[(3-Chloro-5-fluorophenyl)methyl]-5-methyl-7-(oxan-4-yl)-[1,2,4]triazolo[1,5-a]pyrimidin-2-amine; |
| 85 | 5-Methyl-N-{[1-methyl-3-(trifluoromethyl)-1H-pyrazol-5-yl]methyl}-7-(oxan-4-yl)-[1,2,4]triazolo[1,5-a]pyrimidin-2-amine; and |
| 86 | 3-({[5-Methyl-7-(oxan-4-yl)-[1,2,4]triazolo[1,5-a]pyrimidin-2-yl]amino}methyl)benzonitrile. |

Further embodiments are provided by pharmaceutically acceptable salts of compounds of Formula (I), pharmaceutically acceptable prodrugs of compounds of Formula (I), and pharmaceutically active metabolites of compounds of Formula (I).

Isotopically-Labeled Compounds

Compounds of Formula I may include any isotope where one or more atoms are replaced by an atom having an atomic mass or mass number different from the atomic mass or mass number usually found in nature. For example, the isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Each chemical element as represented in a compound of Formula I (and derivatives of such compounds, such as pharmaceutically acceptable salts and prodrugs) may include any isotope of said element. Isotopically-labeled compounds of the present embodiments are useful in drug and substrate tissue distribution and target occupancy assays. For example, isotopically labeled compounds are particularly useful in SPECT (single photon emission computed tomography) and in PET (positron emission tomography), as discussed further herein.

Compositions

In some embodiments compounds of Formula (I) and pharmaceutically acceptable salts thereof are used, alone or in combination with one or more additional active ingredients, to formulate pharmaceutical compositions. Some embodiments provide a pharmaceutical composition comprising: (a) an effective amount of at least one active agent as disclosed and described herein; and (b) a pharmaceutically acceptable excipient.

Formulations and Administration

Numerous standard references are available that describe procedures for preparing various formulations suitable for administering the compounds according to the embodiments. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present embodiments. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present embodiments is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present embodiments or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present embodiments or stabilized form of the compound (e.g., complex with a cyclodextrin derivative or other known complexation agent)) is dissolved in a suitable solvent in the presence of one or more of the excipients described above. The compound of the present embodiments is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Dosage Forms

The present compounds may be systemically administered, e.g., orally, in combination with a pharmaceutically acceptable vehicle such as an inert diluent or an assimilable edible carrier. Hence in some embodiments, chemical entities of the present embodiments are suitable for oral administration. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present embodiments may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

In some embodiments, the active ingredient can be administered to achieve peak plasma concentrations of the active compound of from about 0.5 to about 75 µM, preferably, about 1 to 50 µM, and more preferably, about 2 to about 30 µM. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present embodiments.

Effective amounts or doses of the active agents of the present disclosure may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

Some embodiments provide a method of using isotopically labeled compounds and prodrugs of the present disclosure in: (i) metabolic studies (preferably with $^{14}C$), reaction kinetic studies (with, for example $^2H$ or $^3H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the embodiments thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^2H$) may afford certain therapeutic advantages resulting from greater metabolic stability, for example increased in vivo half-life or reduced dosage requirements.

THERAPEUTIC METHODS

Generally

Chemical entities of the present embodiments are useful in methods (or in the manufacture of a medicament for use in such methods) of treating a disorder mediated by PDE2 by administering to a subject in need thereof an effective amount of a chemical entity of the present embodiments. They are also useful in methods (or in the manufacture of a medicament for use in such methods) of enhancing cognitive or motor function by administering to a subject in need an effective amount of a chemical entity of the present embodiments.

Some embodiments provide a method of treating a subject suffering from or diagnosed with a disorder mediated by PDE2 activity, comprising administering to a subject in need of such treatment an effective amount of at least one chemical entity of the present disclosure. In a further embodiment, the subject is diagnosed with a disorder mediated by PDE2 activity.

Chemical entities disclosed and described herein are also useful in enhancing neuronal plasticity—an essential property of the brain that can be augmented in healthy animals and impaired in numerous CNS disorders. Without being limited by mechanism, such chemical entities can enhance cyclic adenosine monophosphate (cAMP) response element binding protein (CREB) pathway function in cells, modulating transcription of multiple genes involved in synaptic plasticity (see, e.g., Tully et al., *Nat. Rev. Drug Discov.* 2003, 2, 267-277; Alberini, *Physiol. Rev.* 2009, 89, 121-145). Some embodiments provide a method of enhancing neuronal plasticity, comprising administering to a subject in need thereof an effective amount of a chemical entity of Formula I.

Chemical entities of the present embodiments are also useful as "agents" (also referred to as "augmenting agents") to augment the efficiency of training protocols, which facilitate functional reorganization in targeted "domains" (or "functions") in the brain. Training protocols can be directed to rehabilitating or enhancing a cognitive or motor function. The training protocol (cognitive or motor training) induces neuronal activity in specific brain regions and produces improved performance of a specific brain (cognitive or motor) function. Chemical entities of the present embodiments agents act as "augmenting agents," which shorten the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc.; and a general administration of CREB pathway-enhancing drugs.

Neurological Disorders

Chemical entities of the present embodiments are useful in methods of treating a neurological disorder, comprising administering to a subject in need thereof an effective amount of a chemical entity of Formula (I). In a specific aspect, the methods are directed to a cognitive deficit ("cognitive impairment") or motor deficit ("motor impairment") associated with (or "due to") the neurological disorder.

A neurological disorder (or condition or disease) is any disorder of the body's nervous system. Neurological disorders can be categorized according to the primary location affected, the primary type of dysfunction involved, or the primary type of cause. The broadest division is between peripheral nervous system (PNS) disorders and central nervous system (CNS) disorders (such as mental and psychiatric disorders). Neurological disorders are well-known in the art, and they include, but are not limited to, the following mental and psychiatric disorders:

Neurodevelopmental (or "developmental" disorders), such as intellectual disability disorders (e.g., Rubinstein-Taybi syndrome, Down syndrome); communication disorders; autism-spectrum disorders; attention-deficit/hyperactivity disorders; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, and schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder, persistent depressive disorder (dysthymia), and other depressive disorders;

Anxiety disorders, such as specific phobia, social anxiety disorder, panic disorder, generalized anxiety disorder (social phobia), posttraumatic stress disorder (PTSD), and other anxiety disorders;

Obsessive-compulsive and related disorders, such as obsessive-compulsive disorder, body dysmorphic disorder, and other obsessive-compulsive and related disorders;

Dissociative disorders, such as dissociative identity disorder, dissociative amnesia, and other dissociative disorders;

Disruptive, impulse-control, and conduct disorders, such as conduct disorders, antisocial personality disorders, and other disruptive, impulse-control, and conduct disorders;

Trauma- and stressor-related disorders, such as posttraumatic stress disorder, adjustment disorders, and other trauma- and stressor-related disorders;

Feeding and eating disorders, such as anorexia, bulimia, and binge-eating disorder;

Sleep-wake disorders, such as insomnia, narcolepsy, parasomnias, and other sleep-wake disorders;

Sexual disorders, such as arousal disorders, desire disorders, substance. medication-induced dysfunctions, and other sexual disorders;

Substance-related and addictive disorders, such as those involving alcohol, drugs, stimulants, opioids, tobacco, and non-substance-related disorders; and other substance-related and addictive disorders; and Personality disorders, such as paranoid personality disorders, antisocial and borderline personality disorders, avoidance personality disorders, and other personality disorders; and In particular embodiments, the disorder is schizophrenia or an anxiety disorder.

In other embodiments, the neurological disorder is an acquired disorder, in which the primary clinical feature is impaired cognition. That is, it is a disorder in which the primary cognitive deficit has not been present since birth or very early life and therefore represents a decline from a previously attained level of functioning. Such disorders, which may be referred to herein as "cognitive disorders" or "neurocognitive disorders" include one or more of the following:

Delirium, such as substance-intoxication (or withdrawal) delirium, medication-induced delirium, and other forms of delirium;

Dementias and other cognitive impairments due to HIV infection or due to neurodegenerative diseases, such as Alzheimer's disease, Parkinson's disease, Huntington's disease, Lewy body disease, Pick's disease, a prion disease (e.g., Creutzfeldt-Jakob disease), Amyotrophic lateral sclerosis (ALS), multiple sclerosis, frontotemporal lobar degeneration, and corticobasal degeneration; dementia due to a vascular disease ("vascular disease"); and other dementias and neurodegenerative diseases;

Age-associated cognitive deficits, including age-associated memory impairment (AAMI), also referred to as age-related memory impairment (AMI) (see, e.g., Crook et al., *Devel. Neuropsychol.* 1986, 2, 261-276); and deficits affecting patients in early stages of cognitive decline, as in Mild Cognitive Impairment (MCI) (see, e.g., Amrniz and Almkvist, *Acta Neurol. Scand. Suppl.* 2003, 179, 34-41), and;

Trauma-dependent losses of cognitive function, such as vascular diseases due to stroke (e.g., ischemic or hemorrhagic stroke) or ischemia; microvascular disease arising from diabetes or arterosclerosis; traumatic brain injury (TBI), such as brain trauma, including subdural hematoma and brain tumor; head trauma (closed and penetrating); head injury; tumors, such as nervous system cancers, including cerebral tumors affecting the thalamic or temporal lobe; hypoxia, and viral infection (e.g., encephalitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such acquired disorders are not necessarily limited to cognitive impairments. For example, trauma related disorders, such as stroke, traumatic brain injury, head trauma, and head injury, may also include impairments in other neurological functions, such as impairments in motor functions.

As used herein, the terms "Neurodevelopment disorders," "Schizophrenia spectrum and other psychotic disorders," Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep-wake disorders," "Sexual disorders," "Substance-related and addictive disorders," Personality disorders," "Delirium," "Neurocognitive disorders," "Delirium," "Dementias," and "Trauma" includes treatment of those mental disorders as described in the Diagnostic and Statistical Manual of Mental Disorders (DSM-5; 5$^{th}$ ed., 2013, American Psychiatric Association). The skilled artisan will recognize that there are alternative nomenclatures and classification systems for mental disorders, and that these systems evolve with medical and scientific progress. Thus the terms described in this paragraph are intended to include like disorders that are described in other diagnostic sources.

In other embodiments, the neurological disorder is a movement or motor disorder, a group that includes, but is not limited to: kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor); chorea, such as that in Huntington's disease; myoclonus (including generalized myoclonus and focal myoclonus); tics (including simple tics, complex tics and symptomatic tics); dystonia; restless leg syndromes; Wilson's Disease; Hallerworden-Spatz disease; basal ganglia disorders; hyperkinetic, hypokinetic, and dyskinetic disorders; movement disorders induced by drugs; and other movement and motor disorders.

Augmented Training

In certain embodiments, chemical entities of the present disclosure provide augmenting agents to enhance the efficiency of training protocols, including cognitive training and motor training protocols. Such methods are known as "augmented training," and, more particularly, "augmented cognitive training" or "augmented motor training."

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (see, e.g., U.S. Pat. No. 7,868,015; U.S. Pat. No. 7,947,731; US 2008-0188525). When administered in combination with training protocols (or "training"), augmenting agents enhance functional reorganization in targeted domains (or "functions") in the brain.

Cognitive domains (or functions) that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory) memory, such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols

Training protocols (or "modules") are well known in the art and typically comprise a set of distinct exercises that can be process-specific or skill-based: See, e.g., Kim et al., *J. Phys. Ther. Sci.* 2014, 26, 1-6, Allen et al., *Parkinsons Dis.* 2012, 2012, 1-15; Jaeggi et al., *Proc. Natl. Acad. Sci. USA* 2011, 108, 10081-10086; Chein et al., *Psychon. Bull. Rev.* 2010, 17, 193-199; Klingberg, *Trends Cogn. Sci.* 2010, 14, 317-324; Owen et al., Nature 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of fact, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a PDE2 inhibitor, and more particularly, is a chemical entity of the present disclosure, and is administered in conjunction with training. By "in conjunction" is meant that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a compound or composition of the present disclosure can be used as an augmenting agent in conjunction with any psychotherapeutic approach intended to modulate cognitive function in the brain, thereby enhancing the efficacy of such therapy by reducing the number of sessions necessary to attain benefits.

Stroke

In some embodiments, chemical entities and compositions of the present disclosure are useful in treating stroke, and in more specific embodiments, treating motor or cognitive impairments during post-stroke rehabilitation. Stroke care is a temporal continuum that includes immediate (acute) treatments and subsequent rehabilitative therapy.

Acute treatments directly target the initial damage, such as that triggered by ischemic or hemorrhagic stroke; they usually involve using agents to dissolve clots and restore blood flow to reduce tissue damage and stabilize the patient. The efficacy of acute treatments is typically limited to a short time window extending only a few hours from stroke onset.

The focus of stroke treatment shifts to rehabilitation after the patient has been medically stabilized. Rehabilitation (also referred to as "stroke rehabilitation" or "post-stroke rehabilitation") is directed to cognitive and motor deficits that persist after the initial stroke injury, the goal being to restore and recover neurological function as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; by problems with balance or coordination; deficits in gross motor skills such as gait and walking speed; deficits in fine motor skills or manual dexterity; and deficits in upper and lower extremity function.

Accordingly, the present disclosure provides the use of a PDE2 inhibitor in the treatment of stroke, including post stroke rehabilitation. In certain embodiments, chemical entities are useful during stroke rehabilitation to treat stroke deficits (or "post-stroke deficits") resulting from impaired neurological functions. Some embodiments provide methods of treating a neurological deficit during post-stroke rehabilitation comprising: (a) administering to a subject in need thereof a PDE2 inhibitor during recovery of the subject from stroke; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE2 inhibitor is a chemical entity of the present disclosure. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions are useful in treating traumatic brain injury (TBI), and in more specific embodiments, treating motor or cognitive impairments during rehabilitation after the initial trauma. Like stroke care, TBI case is a temporal continuum that includes immediate (acute) treatments and subsequent rehabilitative therapy.

Some embodiments provide the use of a PDE2 inhibitor in the treatment of TBI, including during TBI rehabilitation to treat TBI deficits (or "post-TBI deficits") resulting from impaired neurological functions. Some embodiments provide methods of treating a neurological deficit during post-TBI rehabilitation comprising: (a) administering to a subject in need thereof a PDE2 inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE2 inhibitor is a chemical entity of the present disclosure. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Peripheral Disorders

Chemical entities of the present disclosure are useful in methods of treating peripheral disorders, that is, disorders other than a primary neurological disorder. These uses are supported by PDE2A expression studies and other observations (see, e.g., Bayer Healthcare AG, Intl. Pat. Appl. Publ. WO/2004/044234, May 27, 2004; Donzeau-Gouge et al., *J. Physiol.* 2001, 533, 329-340; Herring et al., *Card. Res.* 2001, 52, 446-453; Keravis et al., *J. Vasc. Res.* 2000, 37, 235-249; Wolda et al., *J. Histochem. Cytochem.* 1999, 47, 895-906; Dickinson et al., *Biochem. J.* 1997, 323, 371-377; Fischmeister et al., *J. Clin. Invest.* 1997, 99, 2710-2718; Houslay et al., *Cell. Signal.* 1996, 8, 97-110; and Haynes et al., *J. Pharm. Exp. Ther.* 1996, 276, 752-757).

Some embodiments provide methods of treating a peripheral disorder, comprising administering to a subject in need thereof an effective amount of a chemical entity of Formula (I). Peripheral disorders include, but are not limited to, infectious diseases, such as bacterial, fungal, protozoan, and viral infections; hematological diseases, such as anemias, myeloproliferative disorders, hemorrhagic disorders, leukopenias, eosinophilic disorders, leukemias, lymphomas, and plasma cell dyscrasias; cardiovascular diseases such as congestive heart failure, myocardial infarction, ischemic diseases, atrial and ventricular anhythmias, pulmonary hypertension, hypertensive vascular diseases, and atherosclerosis; gastroenterological disorders, such as diseases of the esophagus, stomach, duodenum, pancreas, bowel, and liver; dermatological disorders, such as psoriasis, dermatitis, impetigo, folliculitis, melanoma; and other peripheral disorders, including renal diseases, in particular kidney failure, inflammatory diseases; migraine and cancer pain.

Animal Skill Training Protocols

In some embodiments, chemical entities of the present invention are used to enhance the efficiency of training protocols directed to cognitive and motor skills in an animal. Such augmented training reduces the time necessary to acquire or enhance a cognitive or motor skill in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a single drug in a service animal. In other embodiments, the training protocol may be directed to a complex set of skills, such as those underlying search and rescue training of a service animal; for a complex set of skills, training will therefore comprise more than one task.

Some embodiments provide a method of teaching a non-human animal one or more skills, comprising (a) administering to a non-human animal in need thereof a PDE2 inhibitor; (b) providing training to the animal under conditions sufficient to improve performance of the one or more skills; and (c) repeating steps (a) and (b) one or more times, whereby the amount of training sufficient to improve the performance is reduced compared to that produced by training alone.

EXAMPLES

The present disclosure will be further illustrated by the following non-limiting Examples. These Examples are understood to be exemplary only, and they are not to be construed as limiting the scope of the one or more embodiments, and as defined by the appended claims.

PREPARATIVE EXAMPLES

Exemplary compounds will now be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

Abbreviations

The specification includes numerous abbreviations, whose meanings are listed in the following Table:

TABLE 1

| Abbreviation | Definition |
| --- | --- |
| ACN | Acetonitrile |
| BOC or Boc$_2$O | tert-butoxycarbonyl or Di-tert-butyl dicarbonate |
| CELITE ® | Diatomaceous earth |
| CDI | 1,1'-Carbonyldiimidazole |
| DCM | Dichloromethane |
| DIPEA, DIEA | N,N-ethyl-diisopropylamine or N,N-Diisopropyl-ethyl amine |
| DMA | N,N-Dimethylacetamide |
| DME | Dimethoxyethane |
| DMF | N,N-Dimethylformamide |
| DMSO | Dimethylsulfoxide |
| dppf | 1,1'-Bis(diphenylphosphino)ferrocene |
| EtOAc, or EA | Ethyl Acetate |
| EtOH | Ethanol |
| Fe(acac)$_3$ | Tris(acetylacetonato)Iron (III) |
| IPA | Isopropyl alcohol |
| HOAc or AcOH | Acetic Acid |
| HPLC | High-performance liquid chromatography |
| LiHMDS, LHMDS | Lithium bis(trimethylsilyl)amide |
| LDA | Lithium diisopropylamide |
| LCMS, LC/MS | Liquid chromatography-mass spectrometry |
| MeOH | Methanol |
| NMP | 1-Methyl-2-pyrrolidinone |
| Pd/C | Palladium on activated carbon |
| Pd$_2$(dba)$_3$ | Tris(dibenzylideneacetone)dipalladium (0) |
| PdCl$_2$(dPPf)-Cl$_2$ adduct | [1'1'-Bis(diphenylphosphino)ferrocene] palladium(11)dichloride dichloromethane adduct |
| Pd(PPh$_3$)$_4$ | Palladium-tetrakis(triphenylphosphine) |
| TEA, Et$_3$N | Triethylamine |
| TFA | Trifluoroacetic acid |
| THF | Tetrahydrofuran |

Synthetic Schemes

SCHEME A

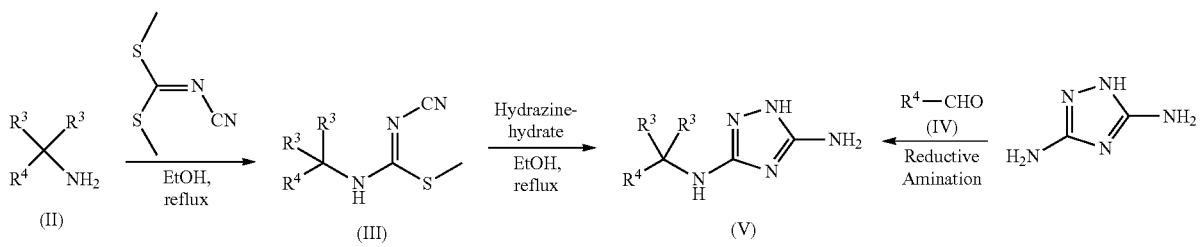

According to Scheme A, a diamino-1,2,4-triazole compound of formula (V) is prepared in two steps from commercially available or synthetically accessible compounds of formula (II). Amines of formula (II), where each $R^3$ is independently —H or —$C_{1-4}$alkyl, and $R^4$ is phenyl or heteroaryl, are reacted with a dialkyl cyanodithioimino carbonate such as dimethyl cyanocarbonimidodithioate, in a solvent such as EtOH, and the like, to provide compounds of formula (III). Subsequent reaction with hydrazine, in an appropriate solvent, at the reflux temperature of the solvent, provides diamino-1,2,4-triazole compounds of formula (V). In an alternate method, 1H-1,2,4-triazole-3,5-diamine is reacted with appropriately substituted commercially available or synthetically accessible aldehydes of formula (IV), where $R^4$ is phenyl or heteroaryl, employing reductive amination reaction conditions known to one skilled in the art. For example, reaction of 1H-1,2,4-triazole-3,5-diamine with an aldehyde of formula (IV), where $R^4$ is phenyl or heteroaryl, in the presence of a suitable reducing agent such as $NaBH_4$, and the like, in a solvent such as EtOH, DCM, DMA, and the like, at temperatures ranging from room temperature to the reflux temperature of the solvent, for a period of 3-6 h, to provide a compound of formula (V) where each $R^3$ is —H. Alternately, ketones of formula $R^4$—C(O)$C_{1-4}$alkyl, where $R^4$ is as described above, may be reacted in a reductive amination reaction with 1H-1,2,4-triazole-3,5-diamine to provide a compound of formula (V) where one $R^3$ is —H and the other $R^3$ is —$C_{1-4}$alkyl.

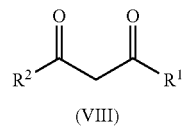

According to Scheme B, β-diketo compounds of formula (VIII) are commercially available or synthetically accessible. Acids of formula (VI), where $R^1$ is an optionally substituted —$C_{1-6}$alkyl, —$C_{3-6}$cycloalkyl, or heterocycloalkyl group, are activated with an activating agent, such as CDI and the like, followed by reaction with the lithium enolate of a compound of formula $R^2$—C(O)$CH_3$ (formula (VII)), where $R^2$ is —$C_{1-3}$alkyl or —$C_{3-6}$cycloalkyl, in a solvent such as THF, at a temperature of about −78° C., for a period of 1-2 h, provides β-diketo compounds of formula (VIII).

SCHEME C

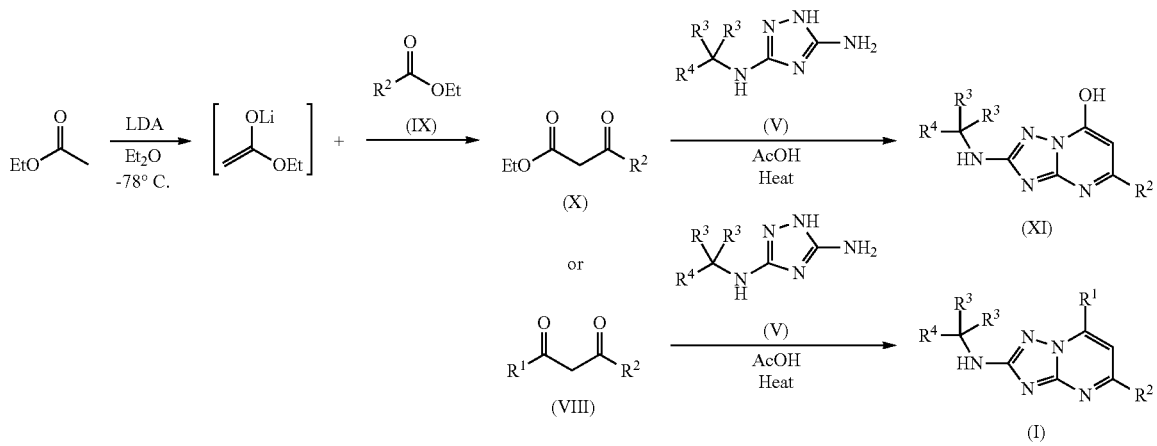

According to Scheme C, Claisen Condensation of the ester enolate of ethyl acetate and a ester of formula (IX), employing conditions known to one of skill in the art, provides β-keto esters of formula (X). Condensation of commercially available or synthetically accessible compounds of formula (X) with compounds of formula (V), where each $R^3$ is independently —H or —$C_{1-4}$alkyl, and $R^4$ is phenyl or heteroaryl, in a solvent such as AcOH, at temperatures ranging from 80° C. to 100° C., for a period of 8 to 24 h, provides compounds of formula (XI). Condensation of commercially available or synthetically accessible compounds of formula (VIII) with compounds of formula (V), as previously described, provides compounds of Formula (I).

SCHEME B

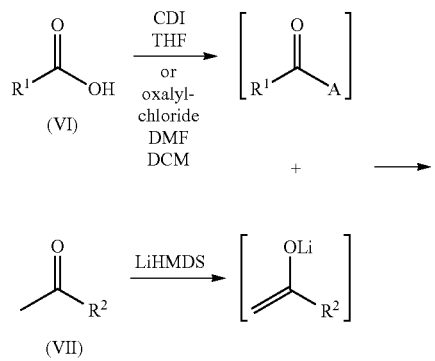

SCHEME D

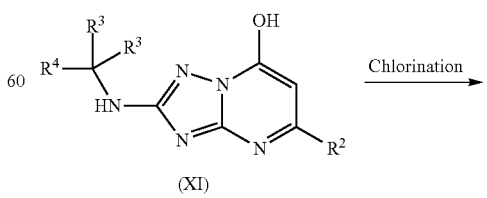

SCHEME E

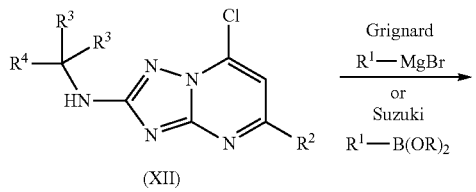 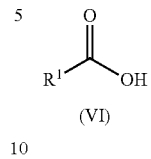 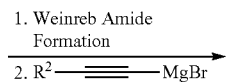

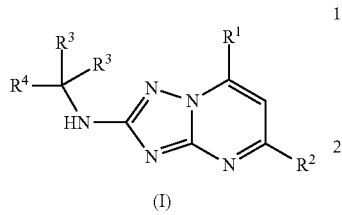 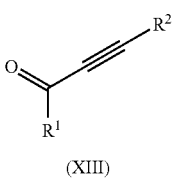 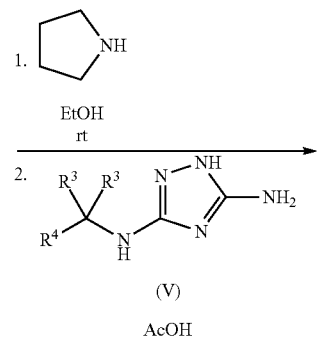

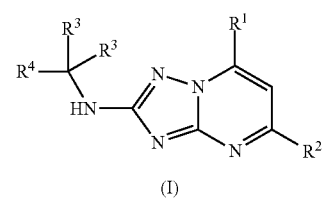

As shown in Scheme D, a compound of formula (XI) is chlorinated, employing conditions known to one of skill in the art to provide a compound of formula (XII). For example, reaction of a compound of formula (XI), with a chlorinating agent such as $POCl_3$, and the like, in a suitable solvent, at temperatures ranging from rt to 80° C., provides a compound of formula (XII).

A compound of formula (XII), is reacted under cross coupling conditions known to one of ordinary skill in the art. For example, reaction with a Grignard reagent such as, $R^1$—MgBr, $R^1$—MgCl, and the like, where $R^1$ is —$C_{1-6}$alkyl or —$C_{3-6}$cycloalkyl, a catalyst such as CuI, $Fe(acac)_3$, and the like, in a solvent such as THF, $Et_2O$, and the like, at temperatures ranging from 0° C. to room temperature, for a period of 0.3 to 2 h, to provide a compound of Formula (I), where $R^1$ is —$C_{1-6}$alkyl, —$C_{3-6}$cycloalkyl, or heterocycloalkyl. Alternate metal catalyzed cross-coupling conditions employ organozinc reagents.

According to Scheme D, chloro compounds of formula (XII), are reacted under palladium or copper catalyzed coupling conditions, for example, under Suzuki reaction conditions, by the reaction of chloro compounds of formula (XII), with commercially available or synthetically accessible boronic acids or esters of formula $R^1$—$B(OR)_2$, where $R^1$ is —$C_{1-6}$alkyl, —$C_{3-6}$cycloalkyl or heterocycloalkyl, in a solvent such as DME, ACN, toluene, EtOH, $H_2O$, or a mixture thereof, in the presence of a base such as, $NaHCO_3$, $Na_2CO_3$, $K_2CO_3$, $K_3PO_4$, $Cs_2CO_3$, and the like, and on organotransition metal catalyst such as $Pd_2(dba)_3$, $Pd(dppf)_2$, $Pd(PPh_3)_4$, and the like, using conventional or microwave heating, at temperatures ranging from 80 to 120° C., to provide a compound of Formula (I). Subsequent reduction of compounds of Formula (I) that include a double bond, employing conditions known to one skilled in the art, for example, Pd/C, under a hydrogen atmosphere, provides compounds of Formula (I) where the double bond is hydrogenated.

Compounds of formula (XIII) are prepared in two steps from compounds of formula (VI). Formation of the Weinreb Amide of a compound of formula (VI), followed by Grignard reaction, employing conditions known to one of skill in the art. For example, reaction of a compound of formula (VI), where $R^1$ is a heterocycloalkyl group, with N,O-dimethylhydroxylamine hydrochloride, in a solvent such as DCM, and the like, a base such as DIEA, and the like, and 2,4,6-tripropyl-1,3,5,2,4,6-trioxatriphosphinane 2,4,6-trioxide, at temperatures ranging from 0° C. to room temperature provides the Weinreb amide of a compound of formula (VI). Subsequent reaction with an alkylmagnesium halide reagent such as prop-1-yn-1-ylmagnesium bromide, in a suitable solvent such as toluene, and the like, at temperatures ranging from 0° C. to room temperature provides a compound of formula (XIII), where $R^1$ is as defined above. A compound of Formula (I) is prepared in two steps from a compound of formula (XIII). Reaction of a compound of formula (XIII), with pyrrolidine, in a solvent such as EtOH, and the like, at as appropriate temperature, for a period of 30 min to 1 h, provides the corresponding aminoenone. Reaction of the aminoenone with a compound of formula (V), in a solvent such as AcOH/water, at a temperature of about 55° C., for a period of 18 to 24 h, provides a compound of Formula (I).

SCHEME F

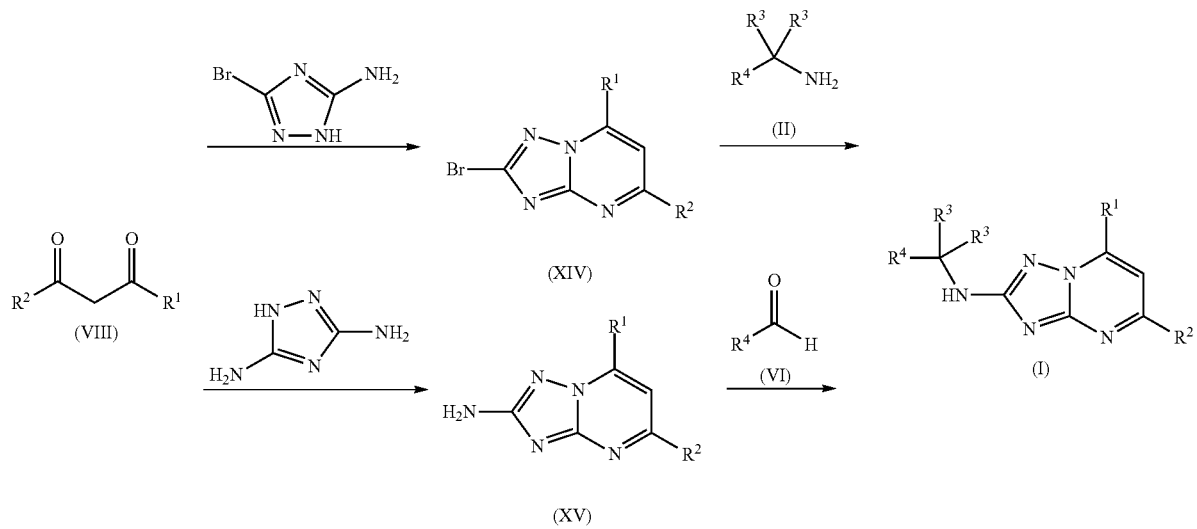

Condensation of 3-bromo-1H-1,2,4-triazol-5-amine or 1H-1,2,4-triazole-3,5-diamine, with a commercially available or synthetically accessible diketo compound of formula (VIII), as previously described, provides compounds of formula (XIV) or formula (XV). A compound of Formula (I), is prepared from the corresponding bromo compound of formula (XIV), and an amine compound of formula (II), employing conventional and/or microwave heating, at temperatures ranging from 100 to 200° C., to provide a compound of Formula (I).

A compound of Formula (I), is prepared from the corresponding amine compounds of formula (XV), employing methods known to one skilled in the art, such as but not limited to a reductive amination reaction. For example, a compound of formula (XV), is reacted with an appropriate synthetically accessible or commercially available carbonyl intermediates of formula (VI), where $R^4$ is phenyl or heteroaryl, in a solvent such as THF, DCM, MeOH and the like, with a reducing agent, such as $NaBH(OAc)_3$, $NaBH_3CN$, $NaBH_4$, and the like, at temperatures ranging from 0 to 50° C., for a period of 1 to 4 h, to provide a compounds of Formula (I).

Compounds prepared according to the schemes described above may be obtained as single enantiomers, diastereomers, or regioisomers, by enantio-, diastero-, or regiospecific synthesis, or by resolution. Where the compounds have at least one chiral center, they may accordingly exist as enantiomers. Where the compounds possess two or more chiral centers, they may additionally exist as diastereomers. It is to be understood that all such isomers and mixtures thereof are encompassed within the scope of the present embodiments. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the embodiments.

EXAMPLES

Chemistry:

In obtaining the compounds described in the examples below, and the corresponding analytical data, the following experimental and analytical protocols were followed unless otherwise indicated.

Unless otherwise stated, reaction mixtures were magnetically stirred at room temperature (rt) under nitrogen atmosphere. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on Silica ($SiO_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Preparative HPLC was performed on a Shimadzu SIL-10AP system using a Waters SunFire™ OBD 30 mm×100 mm×2.5 m (particle size) $C^{18}$ column with a 15 minute gradient of 10-100% acetonitrile in water and 0.05% trifluoroacetic acid added as a modifier to both phases. Elution profiles were monitored by UV at 254 and 220 nm.

Nuclear magnetic resonance (NMR) spectra were obtained in a Varian 400 MHz or Bruker 400 MHz NMR. Samples were analyzed in either deuterated acetone (($CD_3)_2CO$)), chloroform ($CDCl_3$), mEtOH-$d_4$ ($CD_3OD$), or dimethyl sulfoxide-$d_6$ (DMSO-$d_6$). For $CDCl_3$ samples, the residual central resonance peak at 7.26 for ¹H was used for chemical shift assignment for ¹H NMR spectra. For CD₃OD the residual central resonance peak at 3.31 for ¹H was used for chemical shift assignment and for DMSO-d₆ the residual central resonance peak at 2.50 ppm for ¹H was used for chemical shift assignment. The format of the ¹H NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, Mass.) or ChemAxon.

Intermediate 1. N³-(4-Methoxybenzyl)-1H-1,2,4-triazole-3,5-diamine

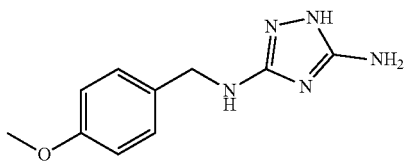 [SMILES: COc1ccc(CNc2n[nH]c(N)n2)cc1]

Step 1. Methyl N'-cyano-N-(4-methoxybenzyl)carbamimidothioate. To a solution of dimethyl N-cyanodithioiminocarbonate (11.67 g, 82.5 mmol) in EtOH (140 mL) was added (4-methoxyphenyl)methanamine (11.54 g, 75 mmol) drop-wise at 10° C. After addition, the mixture was stirred at room temperature for 3 h. The mixture was then filtered and the collected precipitate was air dried to afford the title compound as a colorless solid (17.50 g, 99%). ¹H NMR (400 MHz, DMSO-d₆) δ=8.82 (br s, 1H), 7.22 (d, J=8.4 Hz, 2H), 6.90 (d, J=8.4 Hz, 2H), 4.41 (s, 2H), 3.73 (s, 3H), 2.59 (s, 3H); [M+H]=236.33.

Step 2. N³-(4-Methoxybenzyl)-1H-1,2,4-triazole-3,5-diamine. A solution of methyl N'-cyano-N-(4-methoxybenzyl)carbamimidothioate (17.5 g, 74.4 mmol) in EtOH (150 mL) was treated with hydrazine monohydrate (7.45 g, 148.7 mmol), the resulting mixture was heated at reflux for 5 h. The mixture was then cooled, filtered, and the collected precipitate was air dried to afford the title compound as a colorless solid (15.05 g, 92%). ¹H NMR (400 MHz, DMSO-d₆) δ=10.66 (br s, 1H), 7.22 (d, J=8.3 Hz, 2H), 6.84 (d, J=8.3 Hz, 2H), 5.59 (br s, 2H), 4.99-4.46 (m, 1H), 4.13 (d, J=6.0 Hz, 2H), 3.71 (s, 3H); [M+H]=220.06.

Intermediate 2. N³-((1-Phenyl-1H-pyrazol-4-yl)methyl)-1H-1,2,4-triazole-3,5-diamine

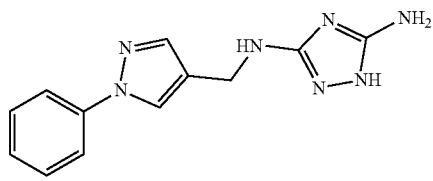 [SMILES: Nc1nc(NCc2cnn(-c3ccccc3)c2)n[nH]1]

A suspension of 1H-1,2,4-triazole-3,5-diamine (1.98 g, 20 mmol) in EtOH (80 mL) was treated with 1-phenyl-1H-pyrazole-4-carbaldehyde-hydrate (3.52 g, 20 mmol) and the resulting mixture heated at reflux for 3 h. The mixture was cooled to rt and NaBH₄ (832 mg, 22.0 mmol) was added portion-wise. The reaction mixture reheated to 40° C. for 15 minutes. The solvent of the mixture was then evaporated to ~half volume, the solids filtered, and the collected precipitate was air dried to afford the title compound as a colorless solid (2.45 g, 48%). ¹H NMR (400 MHz, DMSO-d₆) δ=10.78 (br s, 1H), 8.33 (s, 1H), 7.77 (d, J=1.2 Hz, 1H), 7.76-7.74 (m, 1H), 7.67 (s, 1H), 7.47 (dd, J=7.6, 8.4 Hz, 2H), 7.31-7.24 (m, 1H), 5.82 (br s, 1H), 5.34 (br s, 2H), 4.14 (d, J=6.3 Hz, 2H); [M+H]=256.22.

Intermediate 3. 7-Chloro-N-(4-methoxybenzyl)-5-methyl-[1,2,4]triazolo[1,5-a]pyrimidin-2-amine

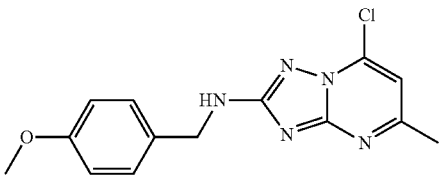

Step 1. 2-((4-Methoxybenzyl)amino)-5-methyl-[1,2,4]triazolo[1,5-a]pyrimidin-7-ol. A solution of N³-(4-methoxybenzyl)-1H-1,2,4-triazole-3,5-diamine (Intermediate 1, 10.96 g, 50 mmol) in glacial acetic acid (860 mL) was treated with ethyl acetoacetate (6.51 g, 50 mmol). The resulting mixture heated at 70-80° C. for 12 h. The mixture was cooled and solids filtered. The collected precipitate was air dried to afford the title compound as a colorless solid (14.3 g, 97%). ¹H NMR (400 MHz, DMSO-d₆) δ=12.31 (br s, 1H), 7.23 (d, J=8.6 Hz, 2H), 7.01 (t, J=6.3 Hz, 1H), 6.84 (d, J=8.6 Hz, 2H), 5.61 (s, 1H), 4.28 (d, J=6.7 Hz, 2H), 3.31 (br s, 3H), 2.20 (s, 3H); [M+H]=286.22.

Step 2. 7-Chloro-N-(4-methoxybenzyl)-5-methyl-[1,2,4]triazolo[1,5-a]pyrimidin-2-amine. A solution of 2-((4-methoxybenzyl)amino)-5-methyl-[1,2,4]triazolo[1,5-a]pyrimidin-7-ol (1.60 g, 5.6 mmol) in phosphorus oxychloride (5 mL) was treated with pyridine (250 μL). The resulting mixture heated at 60° C. for 6 h. The reaction was then concentrated under reduced pressure and partitioned between DCM (50 mL) and a 10% aqueous solution of Na₂CO₃ (50 mL). The organic portion was dried (MgSO₄), filtered, and concentrated under reduced pressure to afford a crude solid which was triturated with EtOAc to afford the title compound as a yellow solid (1.70 g, 44%); [M+H]=304.18.

Intermediate 4. 1-(Tetrahydro-2H-pyran-4-yl)butane-1,3-dione

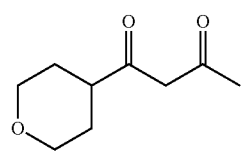

A solution of tetrahydro-2H-pyran-4-carboxylic acid (16.27 g, 125 mmol) and CDI (24.32 g, 150 mmol) in THF (400 mL) was stirred for 3 h at room temperature. The mixture was then cooled to −78° C. and added to a solution of LiHMDS (250 mL, 1 mol/L, 250 mmol) in THF (100 mL) which had been treated with propan-2-one (18 mL, 250 mmol) and stirred for 1 h at −78° C. The reaction mixture was allowed to warm to room temperature over a 1 h period then diluted with EtOAc (100 mL) and treated with sat. aqueous NH$_4$Cl (400 mL). The organic layer was separated and washed with a brine solution (2×50 mL). The aqueous portion was adjusted to pH~6 with concentrated HCl followed by extraction with EtOAc (200 mL). The organic portions were dried (MgSO$_4$), filtered, and concentrated under reduced pressure to provide an oil. Purification (FCC, SiO$_2$, 30% EtOAc/hexane) provided the title compound as a clear oil (5.70 g, 27%). $^1$H NMR (400 MHz, CDCl$_3$) δ=5.51 (s, 1H), 4.03 (td, J=3.6, 11.5 Hz, 2H), 3.53-3.35 (m, 2H), 2.52-2.31 (m, 1H), 2.08 (s, 3H), 1.84-1.60 (m, 4H); [M+H]=171.27.

Intermediate 5. 2-Bromo-5-methyl-7-(tetrahydro-2H-pyran-4-yl)-[1,2,4]triazolo[1,5-a]pyrimidine

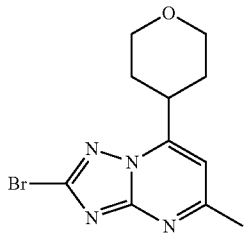 [SMILES: Cc1cc(C2CCOCC2)n2nc(Br)nc2n1]

A solution of 3-bromo-1H-1,2,4-triazol-5-amine (1.63 g, 10 mmol) in AcOH (12 mL) at room temperature was treated with 1-(tetrahydro-2H-pyran-4-yl)butane-1,3-dione (Intermediate 4, 2.04 g, 12 mmol). The reaction mixture was stirred at room temperature for 16 h. The reaction was evaporated to ~one third volume, then filtered and washed with a small amount of EtOAc. The colorless solid was air dried to provide the title compound (270 mg, 40%). $^1$H NMR (400 MHz, CDCl$_3$) δ=6.79 (s, 1H), 4.25-4.03 (m, 2H), 3.76-3.53 (m, 3H), 2.70 (s, 3H), 2.14-2.04 (m, 2H), 1.92-1.77 (m, 2H); [M+H]=297.33/299.34.

Intermediate 6. 7-Chloro-5-(difluoromethyl)-N-(4-methoxybenzyl)-[1,2,4]triazolo[1,5-a]pyrimidin-2-amine

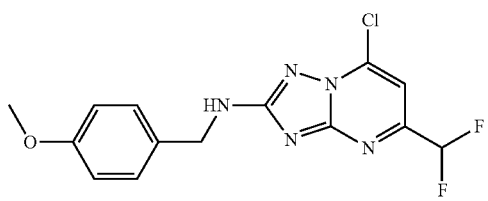 [SMILES: COc1ccc(CNc2nc3nc(C(F)F)cc(Cl)n3n2)cc1]

Step 1. 5-(Difluoromethyl)-2-((4-methoxybenzyl)amino)-[1,2,4]triazolo[1,5-a]pyrimidin-7-ol. A solution of N3-(4-methoxybenzyl)-1H-1,2,4-triazole-3,5-diamine (Intermediate 1, 2.19 g, 10 mmol) in glacial acetic acid (15 mL) was treated with ethyl 4,4-difluoro-3-oxobutanoate (1.99 g, 12 mmol). The resulting mixture was heated at 70-80° C. for 20 h. The mixture was cooled to rt, evaporated to half-volume, and solids filtered. The collected precipitate was air dried to afford the title compound as a colorless solid (2.3 g, 72%). $^1$H NMR (400 MHz, DMSO-d$_6$) δ=7.68 (br s, 1H), 7.29 (d, J=8.6 Hz, 2H), 6.89 (d, J=9.0 Hz, 2H), 6.75 (t, J=52 Hz, 1H), 6.17 (s, 1H), 4.35 (d, J=5.9 Hz, 2H), 3.72 (s, 3H); 19F NMR (376 MHz, DMSO-d6) δ=−118.70 (d, J=56.0 Hz, 2F); [M+H]=322.4.

Step 2. 7-Chloro-5-(difluoromethyl)-N-(4-methoxybenzyl)-[1,2,4]triazolo[1,5-a]pyrimidin-2-amine. The title compound was prepared in a manner analogous to Intermediate 3, Step 2. [M+H]=340.37.

Intermediate 7-Intermediate 12 were prepared in a manner analogous to Intermediate 4 with the appropriate starting material substitutions.

Intermediate 7. 1-(4-Methyltetrahydro-2H-pyran-4-yl)butane-1,3-dione

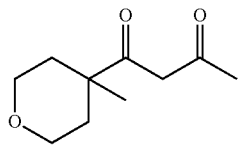

$^1$H NMR (400 MHz, CDCl$_3$) δ=5.60 (s, 1H), 3.73 (ddd, J=3.7, 6.0, 11.8 Hz, 2H), 3.65-3.51 (m, 2H), 2.09 (s, 3H), 2.00 (dddd, J=1.2, 3.2, 5.7, 13.8 Hz, 2H), 1.58-1.45 (m, 2H), 1.20 (s, 3H); [M+H]=185.33.

Intermediate 8. 1-(4-Fluorotetrahydro-2H-pyran-4-yl)butane-1,3-dione

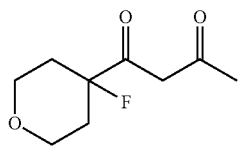

$^1$H NMR (400 MHz, CDCl$_3$) δ=5.92 (d, J=3.5 Hz, 1H), 3.95-3.87 (m, 2H), 3.73 (dt, J=2.0, 11.9 Hz, 2H), 2.12 (s, 3H), 2.29-2.07 (m, 2H), 1.74-1.64 (m, 2H), $^{19}$F NMR (376 MHz, CDCl$_3$) δ=−168.52-169.41 (m, 1F).

Intermediate 9. 1-(Tetrahydro-2H-pyran-3-yl)butane-1,3-dione

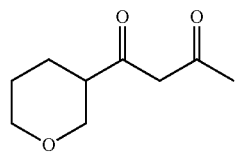

$^1$H NMR (400 MHz, CDCl$_3$) δ=5.53 (s, 1H), 4.00 (ddd, J=1.8, 4.2, 11.2 Hz, 1H), 3.94-3.85 (m, 1H), 3.50 (dd, J=10.0, 11.2 Hz, 1H), 3.45-3.37 (m, 1H), 2.51 (tt, J=4.0, 10.1 Hz, 1H), 2.08 (s, 3H), 1.97 (tdd, J=1.8, 3.6, 10.8 Hz, 1H), 1.81-1.56 (m, 3H); [M+H]=171.31.

Intermediate 10.
1-(Tetrahydrofuran-3-yl)butane-1,3-dione

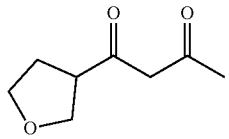

$^1$H NMR (400 MHz, CDCl$_3$) δ=5.52 (s, 1H), 3.96-3.74 (m, 4H), 2.99 (dq, J=6.7, 7.7 Hz, 1H), 2.16-2.06 (m, 2H), 2.03 (s, 3H); [M+H]=157.3.

Intermediate 11.
1-(4,4-Difluorocyclohexyl)butane-1,3-dione

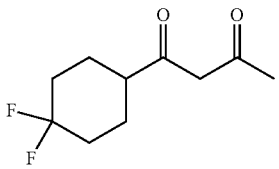

$^1$H NMR (400 MHz, CDCl$_3$) δ=5.52 (s, 1H), 2.25 (br s, 1H), 2.16 (d, J=8.2 Hz, 2H), 2.08 (s, 3H), 1.94 (d, J=10.2 Hz, 2H), 1.87-1.64 (m, 4H), $^{19}$F NMR (376 MHz, CDCl$_3$) δ=−89.13--96.23 (m, 1F), −98.73--104.10 (m, 1F); [M+H]=205.33.

Intermediate 12.
5-Methoxy-5-methylhexane-2,4-dione

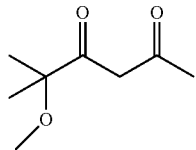

$^1$H NMR (400 MHz, CDCl$_3$) δ=5.91 (s, 1H), 3.23 (s, 3H), 2.19 (s, 3H), 1.32 (s, 6H); [M+H]=159.11.

Intermediate 13.
1-(1-Methylcyclopropyl)butane-1,3-dione

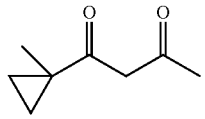

Step 1. 1-Methylcyclopropanecarbonyl chloride. To a solution of 1-methylcyclopropanecarboxylic acid in DCM was added oxalylchloride and a catalytic amount of DMF. The resulting mixture was heated and then the mixture was cooled and concentrated under reduced pressure to afford the title compound which was used crude in the next step without further purification.

Step 2. 1-(1-Methylcyclopropyl)butane-1,3-dione. A solution of 1-methylcyclopropanecarbonyl chloride (1.48 g, 12.5 mmol) in THF (8 mL) was cooled to −78° C. and added to a separate −78° C. solution of lithium bis(trimethylsilyl) amide (25 mL, 1 mol/L, 25 mmol) and THF (25 mL) which had been treated with propan-2-one (1.8 mL, 25 mmol) and stirred for 1 h at −78° C. The reaction mixture was allowed to stir at −78° C. for 1 h. The reaction mixture was quenched with a saturated aqueous solution of NH$_4$Cl (50 mL) and EtOAc (50 mL). The reaction was allowed to warm to room temperature and the organic layer was then separated and washed with a brine solution (50 mL), dried (MgSO$_4$), filtered, and concentrated under reduced pressure. Purification (FCC, SiO$_2$, 10% EtOAc/hexane) provided the title compound (1.06 g, 61%) of light yellow-tinted liquid. $^1$H NMR (400 MHz, CDCl$_3$) δ=5.60 (s, 1H), 2.05 (s, 3H), 1.36-1.32 (m, 1H), 1.30 (s, 3H), 0.80-0.69 (m, 2H), 0.18-0.09 (m, 1H); [M+H]=140.91.

Intermediate 14. Ethyl 4-fluoro-3-oxobutanoate

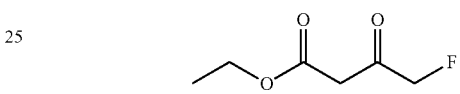

A solution of EtOAc (10.7 mL, 110 mmol) in diethyl ether (100 mL) at −78° C. was treated with LDA (60 mL, 2 mol/L, 120 mmol) and allowed to stir for 45 min. After this time ethyl 2-fluoroacetate (9.7 mL 100 mmol) was added dropwise and the reaction mixture allowed to warm to room temperature and stirred for 16 h. The reaction mixture was then treated with EtOAc (100 mL) and a 20% solution of HCl to adjust the pH to ~4. The organic layer was then separated and washed with brine (50 mL), dried (MgSO$_4$), filtered, and concentrated under reduced pressure. Purification (FCC, SiO$_2$, 25% EtOAc/hexane) provided the title compound as a yellow tinted liquid. $^1$H NMR (400 MHz, CDCl$_3$) δ=4.99-4.82 (m, 2H), 4.20 (q, J=7.0 Hz, 2H), 3.58 (d, J=3.9 Hz, 1H), 1.30-1.24 (m, 3H); [M+H]=148.91.

Intermediate 15.
(3-(Difluoromethyl)-4-methoxyphenyl)methanamine

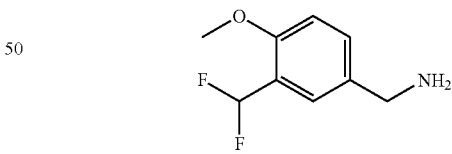

Step 1. 3-Formyl-4-methoxybenzonitrile. Sodium pieces (6 g, 260 mmol) were carefully added to a solution of anhydrous MeOH (200 mL) at 5° C. The reaction mixture was stirred until the sodium was dissolved (~15 minutes) then 4-fluoro-3-formylbenzonitrile (30 g, 200 mmol) was added and the mixture was stirred at 35° C. for 3.5 h. The reaction mixture was then cooled to room temperature and the suspension collected by filtration. The resulting solid was then recrystallized from EtOAc to afford the title compound (27 g, 83%) as an off-white solid. $^1$H NMR (400 MHz, CDCl$_3$) δ=10.43 (s, 1H), 8.13 (d, J=2.2 Hz, 1H), 7.83 (dd, J=8.6, 2.0 Hz, 1H), 7.11 (d, J=8.8 Hz, 1H), 4.03 (s, 3H).

Step 2. 3-(Difluoromethyl)-4-methoxybenzonitrile. A solution of 3-formyl-4-methoxybenzonitrile (15 g, 93 mmol, 1 eq) in anhydrous DCM (200 mL) was treated with DAST (17.9 g, 112 mmol). The reaction mixture was stirred 3-5° C. under nitrogen atmosphere overnight. Then the reaction was quenched with saturated NaHCO$_3$ (200 mL) and extracted with DCM. The extracted organic phase was concentrated under reduced pressure. Purification (FCC, SiO$_2$, petroleum ether/DCM=1:1) afforded the title compound (10 g, 58%) as a colorless solid. $^1$H NMR (400 MHz, CDCl$_3$) δ=7.86 (s, 1H), 7.75 (d, J=8.8 Hz, 1H), 7.04 (br s, 1H), 6.75-7.01 (m, 1H).

Step 3. (3-(Difluoromethyl)-4-methoxyphenyl)methanamine. A solution of 3-(difluoromethyl)-4-methoxybenzonitrile (10 g, 5.4 mmol) in MeOH (500 mL) was treated with Raney Ni (5 g) and ammonia (3.5 g). The mixture was stirred at 20° C. under hydrogen atmosphere for 4 h. The mixture was then filtered though a pad of CELITE® and concentrated under reduced pressure. Purification (FCC, SiO$_2$, (petroleum ether/DCM=1:3-DCM/EtOH=10:1) afforded the title compound (5.5 g, 54%) as a light yellow-tinted oil. $^1$H NMR (400 MHz, CDCl$_3$) δ=7.52 (s, 1H), 7.39 (d, J=8.4 Hz, 1H), 6.95 (t, J=55.2 Hz, 1H), 6.91 (d, J=8.4 Hz, 1H), 3.87 (s, 3H), 3.85 (s, 2H).

Intermediate 16-Intermediate 46 were prepared in a manner analogous to Intermediate 1 with the appropriate starting material substitutions.

Intermediate 16. N$^3$-((2,3-Dihydro-1H-inden-5-yl)methyl)-1H-1,2,4-triazole-3,5-diamine

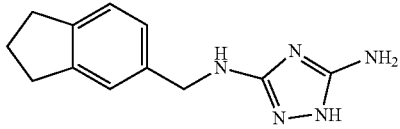 [SMILES: Nc1nc(NCc2ccc3c(c2)CCC3)n[nH]1]

$^1$H NMR (400 MHz, DMSO-d$_6$) δ=7.14 (s, 1H), 7.08-7.04 (dd, 2H), 4.37 (s, 2H), 2.80-2.76 (t, 4H), 1.98-1.94 (m, 2H).

Intermediate 17. N$^3$—Benzyl-1H-1,2,4-triazole-3,5-diamine

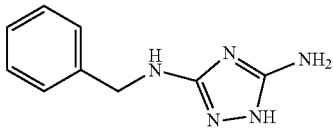 [SMILES: Nc1nc(NCc2ccccc2)n[nH]1]

$^1$H NMR (400 MHz, DMSO-d$_6$) δ=7.14 (s, 1H), 7.08-7.04 (dd, 2H), 4.37 (s, 2H), 2.80-2.76 (t, 4H), 1.98-1.94 (m, 2H).

Intermediate 18. N$^3$-(3-Chlorobenzyl)-1H-1,2,4-triazole-3,5-diamine

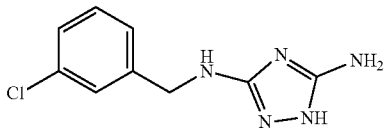 [SMILES: Nc1nc(NCc2cccc(Cl)c2)n[nH]1]

[M+H]=224.07.

Intermediate 19. N$^3$-(2,6-Difluoro-4-methoxybenzyl)-1H-1,2,4-triazole-3,5-diamine

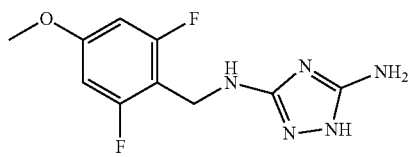 [SMILES: COc1cc(F)c(CNc2n[nH]c(N)n2)c(F)c1]

$^1$H NMR (400 MHz, DMSO-d$_6$) δ=6.68 (d, J=9.8 Hz, 2H), 5.72-5.27 (m, 2H), 4.35 (t, J=5.1 Hz, 1H), 4.16 (d, J=5.9 Hz, 2H), 3.76 (s, 3H); [M+H]=256.28.

Intermediate 20. N$^3$-((2,3-Dihydrobenzo[b][1,4]dioxin-6-yl)methyl)-1H-1,2,4-triazole-3,5-diamine

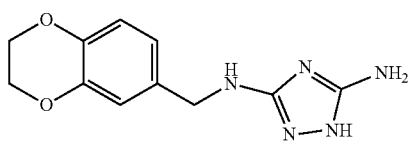 [SMILES: Nc1nc(NCc2ccc3c(c2)OCCO3)n[nH]1]

[M+H]=248.17.

Intermediate 21. N$^3$-(3-(Difluoromethyl)-4-methoxybenzyl)-1H-1,2,4-triazole-3,5-diamine

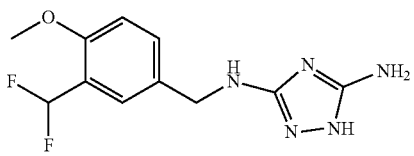 [SMILES: COc1ccc(CNc2n[nH]c(N)n2)cc1C(F)F]

$^1$H NMR (400 MHz, DMSO-d$_6$) δ=10.60 (br s, 1H), 7.47-7.37 (m, 2H), 7.05 (d, J=8.2 Hz, 1H), 7.02 (t, J=1.0 Hz, 1H), 6.0 (br s, 2H), 5.30 (br s, 1H), 4.33 (t, J=4.9 Hz, 1H), 4.16 (d, J=6.7 Hz, 2H), 3.79 (s, 3H); $^{19}$F NMR (376 MHz, DMSO-d$_6$) δ=−113.80 (d, J=1.0 Hz, 2F); [M+H]=270.34.

Intermediate 22. N$^3$-((1-(3-Methoxyphenyl)-1H-pyrazol-4-yl)methyl)-1H-1,2,4-triazole-3,5-diamine

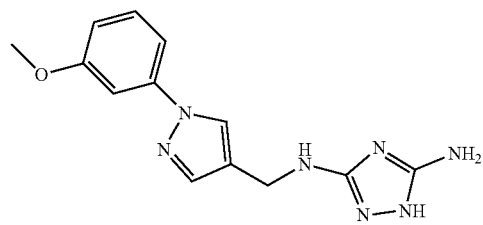 [SMILES: COc1cccc(-n2cc(CNc3n[nH]c(N)n3)cn2)c1]

¹H NMR (400 MHz, DMSO-d₆) δ=10.76 (br s, 1H), 8.35 (s, 1H), 7.66 (s, 1H), 7.41-7.28 (m, 3H), 6.88-6.79 (m, 1H), 5.51 (br s, 3H), 4.13 (d, J=5.9 Hz, 2H), 3.81 (s, 3H); [M+H]=286.38.

Intermediate 23. N³-(3-Methoxybenzyl)-1H-1,2,4-triazole-3,5-diamine

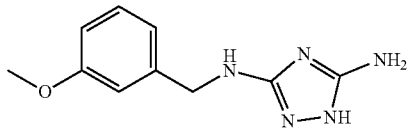 [SMILES: COc1cccc(CNc2n[nH]c(N)n2)c1]

[M+H]=220.12.

Intermediate 24. N³-((2-Methylpyridin-4-yl)methyl)-1H-1,2,4-triazole-3,5-diamine

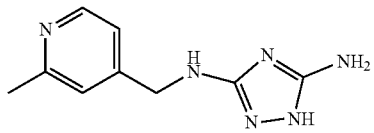

¹H NMR (400 MHz, DMSO-d₆) δ=10.60 (br s, 1H), 8.28 (d, J=4.3 Hz, 1H), 7.12 (s, 1H), 7.06 (dd, J=1.2, 5.1 Hz, 1H), 5.90 (br s, 1H), 5.60 (br s, 2H), 4.79-4.08 (br s, 2H), 2.39 (s, 3H); [M+H]=205.11.

Intermediate 25. N³-((1-(o-Tolyl)-1H-pyrazol-4-yl)methyl)-1H-1,2,4-triazole-3,5-diamine

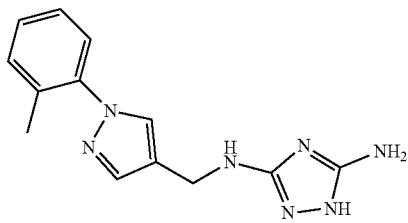 [SMILES: Cc1ccccc1-n1cc(CNc2n[nH]c(N)n2)cn1]

¹H NMR (400 MHz, DMSO-d₆) δ=7.84 (s, 1H), 7.62 (s, 1H), 7.37-7.25 (m, 4H), 4.12 (d, J=6.3 Hz, 2H), 2.18 (s, 3H); [M+H]=270.11.

Intermediate 26. N³-((3-Phenylisoxazol-5-yl)methyl)-1H-1,2,4-triazole-3,5-diamine

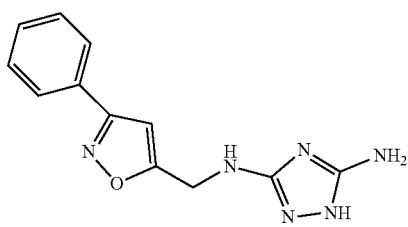 [SMILES: Nc1nc(NCc2cc(-c3ccccc3)no2)n[nH]1]

¹H NMR (400 MHz, DMSO-d₆) δ=10.77 (br s, 1H), 7.84-7.78 (m, 2H), 7.54-7.42 (m, 3H), 6.74 (s, 1H), 6.00 (br s, 1H), 5.65 (br s, 2H), 4.36 (d, J=5.5 Hz, 2H); [M+H]=256.75.

Intermediate 27. N³-(3-Bromobenzyl)-1H-1,2,4-triazole-3,5-diamine

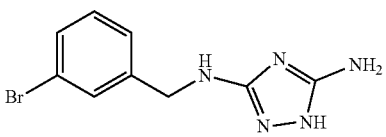 [SMILES: Nc1nc(NCc2cccc(Br)c2)n[nH]1]

[M+H]=268.12.

Intermediate 28. N³-(3-(Trifluoromethyl)benzyl)-1H-1,2,4-triazole-3,5-diamine

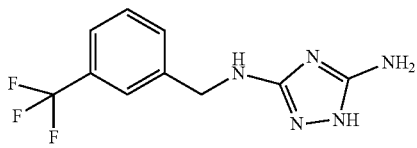 [SMILES: Nc1nc(NCc2cccc(C(F)(F)F)c2)n[nH]1]

[M+H]=258.16.

Intermediate 29. N³-((2,3-Dihydrobenzofuran-5-yl)methyl)-1H-1,2,4-triazole-3,5-diamine

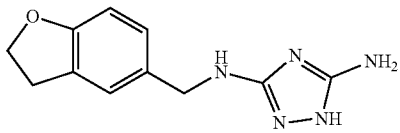 [SMILES: Nc1nc(NCc2ccc3c(c2)CCO3)n[nH]1]

¹H NMR (400 MHz, DMSO-d₆) δ=10.68 (br s, 1H), 7.17 (s, 1H), 7.09-6.96 (m, 1H), 6.65 (d, J=8.2 Hz, 1H), 5.56 (br s, 2H), 4.47 (t, J=8.6 Hz, 2H), 4.11 (d, J=6.7 Hz, 2H), 3.12 (t, J=8.8 Hz, 2H); [M+H]=232.18.

Intermediate 30. N³-((2,3-Dihydrobenzofuran-6-yl)methyl)-1H-1,2,4-triazole-3,5-diamine

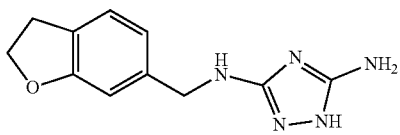 [SMILES: Nc1nc(NCc2ccc3c(c2)OCC3)n[nH]1]

¹H NMR (400 MHz, DMSO-d₆) δ=10.68 (br s, 1H), 7.10 (d, J=7.4 Hz, 1H), 6.75 (dd, J=1.4, 7.6 Hz, 1H), 6.71 (s, 1H), 5.55 (br s, 2H), 4.47 (t, J=8.8 Hz, 2H), 4.13 (d, J=6.7 Hz, 2H), 3.10 (t, J=8.8 Hz, 2H); [M+H]=232.11.

Intermediate 31. $N^3$-(2-Fluorobenzyl)-1H-1,2,4-triazole-3,5-diamine

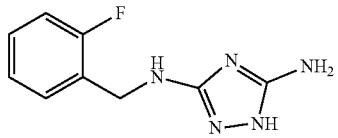 [SMILES: Nc1nc(NCc2ccccc2F)n[nH]1]

[M+H]=208.13.

Intermediate 32. $N^3$-(2-Fluoro-5-methylbenzyl)-1H-1,2,4-triazole-3,5-diamine

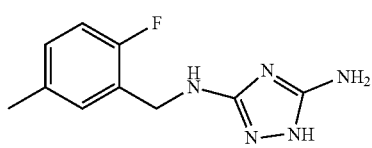 [SMILES: Cc1ccc(F)c(CNc2n[nH]c(N)n2)c1]

[M+H]=222.25.

Intermediate 33. $N^3$-(3-Methylbenzyl)-1H-1,2,4-triazole-3,5-diamine

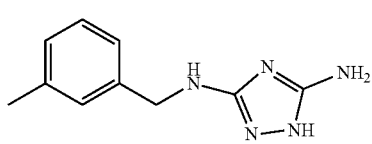

[M+H]=204.33.

Intermediate 34. $N^3$-(2-Methylbenzyl)-1H-1,2,4-triazole-3,5-diamine

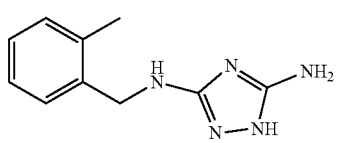

$^1$H NMR (400 MHz, DMSO-d$_6$) δ=10.68 (br s, 1H), 7.30-7.24 (m, 1H), 7.15-7.06 (m, 3H), 5.57 (br s, 3H), 4.19 (d, J=6.3 Hz, 2H), 2.26 (s, 3H); [M+H]=204.36.

Intermediate 35. $N^3$-(2-Chlorobenzyl)-1H-1,2,4-triazole-3,5-diamine

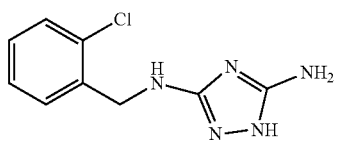 [SMILES: Nc1nc(NCc2ccccc2Cl)n[nH]1]

$^1$H NMR (400 MHz, DMSO-d$_6$) δ=10.72 (br s, 1H), 7.44-7.35 (m, 2H), 7.32-7.19 (m, 2H), 6.02 (br s, 1H), 5.52 (br s, 2H), 4.30 (d, J=6.3 Hz, 2H); [M+H]=224.32.

Intermediate 36. $N^3$-(2,5-Difluorobenzyl)-1H-1,2,4-triazole-3,5-diamine

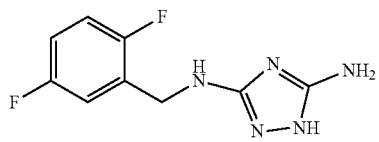 [SMILES: Nc1nc(NCc2cc(F)ccc2F)n[nH]1]

$^1$H NMR (400 MHz, DMSO-d$_6$) δ=10.75 (br s, 1H), 7.33-6.89 (m, 3H), 6.03 (br s, 1H), 5.59 (br s, 2H), 4.25 (d, J=6.3 Hz, 2H); $^{19}$F NMR (376 MHz, DMSO-d$_6$) δ=−119.28 (br s, 1F), −125.10 (br s, 1F); [M+H]=226.34.

Intermediate 37. $N^3$-(3,5-Difluorobenzyl)-1H-1,2,4-triazole-3,5-diamine

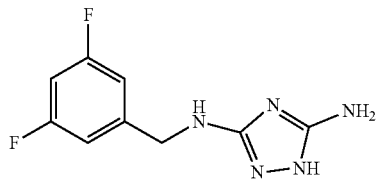 [SMILES: Nc1nc(NCc2cc(F)cc(F)c2)n[nH]1]

$^1$H NMR (400 MHz, DMSO-d$_6$) δ=10.74 (br s, 1H), 7.14-6.77 (m, 3H), 6.11 (br s, 1H), 5.57 (br s, 2H), 4.22 (d, J=6.7 Hz, 2H); $^{19}$F NMR (376 MHz, DMSO-d$_6$) δ=−110.75 (br s, 2F); [M+H]=226.34.

Intermediate 38. $N^3$-(2,6-Difluorobenzyl)-1H-1,2,4-triazole-3,5-diamine

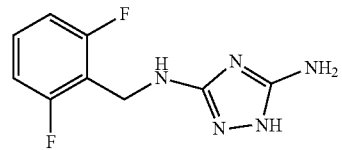 [SMILES: Nc1nc(NCc2c(F)cccc2F)n[nH]1]

$^1$H NMR (400 MHz, DMSO-d$_6$) δ=10.76 (br s, 1H), 7.47-7.19 (m, 1H), 7.15-6.89 (m, 2H), 5.60 (br s, 3H), 4.26 (d, J=5.5 Hz, 2H); $^{19}$F NMR (376 MHz, DMSO-d$_6$) δ=−114.94 (t, J=6.1 Hz, 2F); [M+H]=226.34.

Intermediate 39. $N^3$-((5-Methylpyridin-3-yl)methyl)-1H-1,2,4-triazole-3,5-diamine

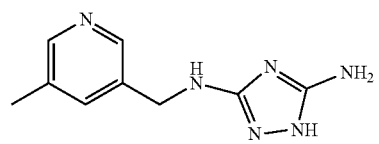

$^1$H NMR (400 MHz, DMSO-d$_6$) δ=10.73 (br s, 1H), 8.31 (d, J=1.6 Hz, 1H), 8.24 (d, J=1.6 Hz, 1H), 7.53-7.49 (m, 1H), 6.00 (br. s, 1H), 5.54 (br s, 2H), 4.19 (d, J=6.7 Hz, 2H), 2.26 (s, 3H); [M+H]=205.34.

Intermediate 40. N$^3$-(3,4-Difluorobenzyl)-1H-1,2,4-triazole-3,5-diazole-3,5-diamine

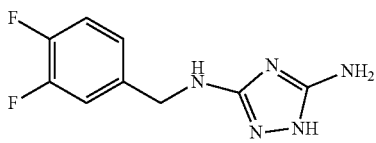 [SMILES: Nc1nc(NCc2ccc(F)c(F)c2)n[nH]1]

$^1$H NMR (400 MHz, DMSO-d$_6$) δ=10.73 (br s, 1H), 7.39-7.25 (m, 2H), 7.19-7.06 (m, 1H), 5.99 (br s, 1H), 5.59 (br s, 2H), 4.18 (d, J=6.3 Hz, 2H); $^{19}$F NMR (376 MHz, DMSO-d$_6$) δ=−139.65 (br s, 1F), −142.55 (br s, 1F); [M+H]=226.34.

Intermediate 41. N$^3$-(4-Fluorobenzyl)-1H-1,2,4-triazole-3,5-diamine

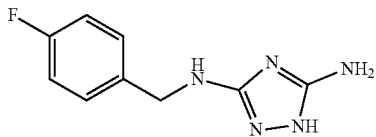 [SMILES: Nc1nc(NCc2ccc(F)cc2)n[nH]1]

$^1$H NMR (400 MHz, DMSO-d$_6$) δ=10.69 (br s, 1H), 7.41-7.21 (m, 2H), 7.08 (t, J=9.0 Hz, 2H), 5.56 (br s, 3H), 4.16 (d, J=6.7 Hz, 2H); [M+H]=208.32.

Intermediate 42. N$^3$-(3-Fluorobenzyl)-1H-1,2,4-triazole-3,5-diamine

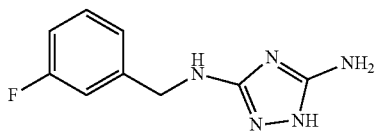 [SMILES: Nc1nc(NCc2cccc(F)c2)n[nH]1]

$^1$H NMR (400 MHz, DMSO-d$_6$) δ=10.72 (br s, 1H), 7.35-7.27 (m, 1H), 7.16-7.07 (m, 2H), 7.00 (dt, J=2.3, 8.6 Hz, 1H), 5.97 (br s, 1H), 5.56 (br s, 2H), 4.23 (d, J=6.7 Hz, 2H); $^{19}$F NMR (376 MHz, DMSO-d$_6$) δ=−114.09 (br s, 1F); [M+H]=208.36.

Intermediate 43. N$^3$-((2-(Trifluoromethyl)pyridin-4-yl)methyl)-1H-1,2,4-triazole-3,5-diamine

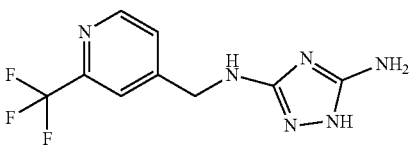 [SMILES: Nc1nc(NCc2ccnc(C(F)(F)F)c2)n[nH]1]

$^1$H NMR (400 MHz, DMSO-d$_6$) δ=10.72 (br s, 1H), 8.64 (d, J=4.7 Hz, 1H), 7.78 (s, 1H), 7.59 (d, J=3.9 Hz, 1H), 6.15 (br s, 1H), 5.67 (br s, 2H), 4.34 (d, J=3.9 Hz, 2H); $^{19}$F NMR (376 MHz, DMSO-d$_6$) δ=−66.48 (br s, 3F); [M+H]=259.4.

Intermediate 44. (R)—N$^3$-(1-(4-Methoxyphenyl)ethyl)-1H-1,2,4-triazole-3,5-diamine

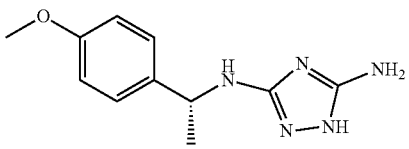 [SMILES: COc1ccc([C@@H](C)Nc2n[nH]c(N)n2)cc1]

$^1$H NMR (400 MHz, DMSO-d$_6$) δ=10.61 (br s, 1H), 7.25 (d, J=8.6 Hz, 2H), 6.82 (d, J=8.6 Hz, 2H), 4.35 (d, J=3.5 Hz, 1H), 3.70 (s, 3H), 1.32 (d, J=7.0 Hz, 3H); [M+H]=234.4.

Intermediate 45. N$^3$-(2,4-Difluorobenzyl)-1H-1,2,4-triazole-3,5-diazole-3,5-diamine

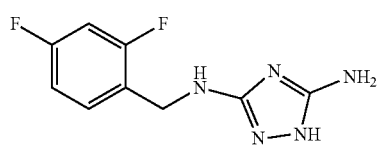 [SMILES: Nc1nc(NCc2ccc(F)cc2F)n[nH]1]

$^1$H NMR (400 MHz, DMSO-d$_6$) δ=10.72 (br s, 1H), 7.50-7.36 (m, 1H), 7.14 (dt, J=2.3, 10.0 Hz, 1H), 7.07-6.95 (m, 1H), 5.95 (m, 1H), 5.57 (br s, 2H), 4.23 (d, J=6.3 Hz, 2H); $^{19}$F NMR (376 MHz, DMSO-d$_6$) δ=−113.40 (br s, 1F), −115.31 (br s, 1F); [M+H]=226.3.

Intermediate 46. (S)—N$^3$-(1-(4-Methoxyphenyl)ethyl)-1H-1,2,4-triazole-3,5-diamine

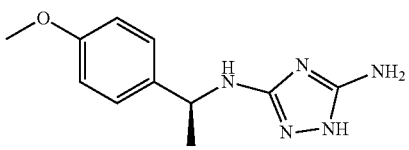 [SMILES: COc1ccc([C@H](C)Nc2n[nH]c(N)n2)cc1]

$^1$H NMR (400 MHz, DMSO-d$_6$) δ=10.55 (br s, 1H), 7.25 (d, J=8.6 Hz, 2H), 6.82 (d, J=8.6 Hz, 2H), 6.00 (br s, 1H), 5.21 (br s, 2H), 4.50 (dd, J=7.0, 9.0 Hz, 1H), 3.70 (s, 3H), 1.32 (d, J=7.0 Hz, 3H); [M+H]=234.4.

Intermediate 47-Intermediate 60 were prepared in a manner analogous to Intermediate 2

Intermediate 47. N$^3$-(2-Fluoro-4-methoxybenzyl)-1H-1,2,4-triazole-3,5-diamine

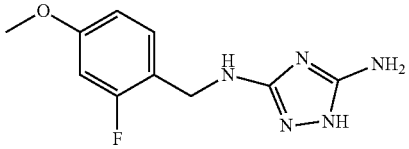 [SMILES: COc1ccc(CNc2n[nH]c(N)n2)c(F)c1]

¹H NMR (400 MHz, DMSO-d₆) δ=7.29 (t, J=8.8 Hz, 1H), 6.88-6.54 (m, 2H), 5.93 (br s, 1H), 5.35 (br s, 2H), 5.10 (br s, 1H), 4.18 (d, J=6.3 Hz, 2H), 3.87-3.64 (s, 3H); ¹⁹F NMR (376 MHz, DMSO-d₆) δ=−117.40 (t, J=9.5 Hz, 1F); [M+H]=238.19.

Intermediate 48. N³-(3-(Difluoromethyl)benzyl)-1H-1,2,4-triazole-3,5-diamine

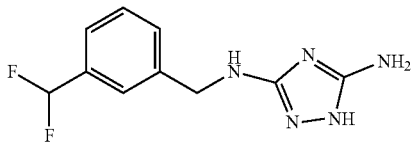 [SMILES: Nc1nc(NCc2cccc(C(F)F)c2)n[nH]1]

[M+H]=240.10.

Intermediate 49. N³-(3-Chloro-4-methoxybenzyl)-1H-1,2,4-triazole-3,5-diamine

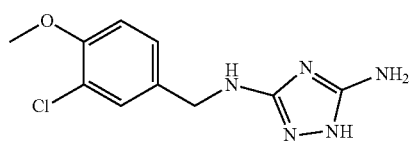 [SMILES: COc1ccc(CNc2n[nH]c(N)n2)cc1Cl]

¹H NMR (400 MHz, DMSO-d₆) δ=10.70 (br s, 1H), 7.35 (d, J=2.0 Hz, 1H), 7.22 (dd, J=2.2, 8.4 Hz, 1H), 7.05 (d, J=8.6 Hz, 1H), 5.90 (br s, 1H), 5.46 (br s, 2H), 4.13 (d, J=6.3 Hz, 2H), 3.81 (s, 3H); [M+H]=254.13.

Intermediate 50. N³-(2-Fluoro-5-methoxybenzyl)-1H-1,2,4-triazole-3,5-diamine

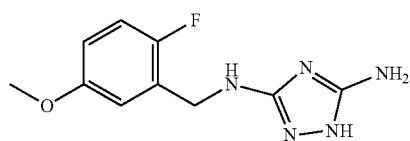 [SMILES: COc1ccc(F)c(CNc2n[nH]c(N)n2)c1]

¹H NMR (400 MHz, DMSO-d₆) δ=7.10-6.99 (m, 1H), 6.95 (dd, J=3.1, 6.3 Hz, 1H), 6.77 (td, J=3.6, 8.9 Hz, 1H), 6.04 (br s, 1H), 5.40 (br s, 2H), 4.23 (d, J=6.7 Hz, 2H), 3.68 (s, 2H); [M+H]=238.17.

Intermediate 51. N³-((2,2-Difluorobenzo[d][1,3]dioxol-5-yl)methyl)-1H-1,2,4-triazole-3,5-diamine

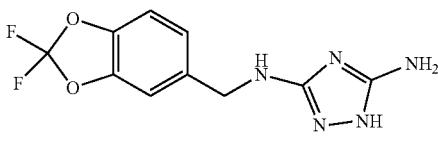 [SMILES: Nc1nc(NCc2ccc3c(c2)OC(F)(F)O3)n[nH]1]

¹H NMR (400 MHz, DMSO-d₆) δ=7.33-7.27 (m, 2H), 7.17-7.10 (m, 1H), 6.15 (br s, 1H), 5.39 (br s, 2H), 5.09 (br s, 1H), 4.20 (d, J=6.7 Hz, 2H); ¹⁹F NMR (376 MHz, DMSO-d₆) δ=−49.14 (s, 2F); [M+H]=270.16.

Intermediate 52. N³-((3-Methyl-1-phenyl-1H-pyrazol-4-yl)methyl)-1H-1,2,4-triazole-3,5-diamine

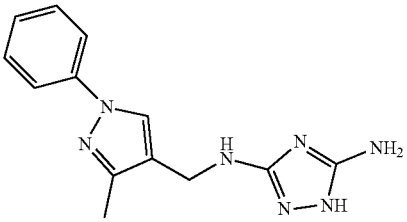 [SMILES: Cc1nn(-c2ccccc2)cc1CNc1n[nH]c(N)n1]

¹H NMR (400 MHz, DMSO-d₆) δ=8.24 (s, 1H), 7.70 (dd, J=1.0, 8.8 Hz, 2H), 7.44 (dd, J=7.6, 8.4 Hz, 2H), 7.27-7.18 (m, 1H), 4.07 (d, J=5.9 Hz, 2H), 2.23 (s, 3H); [M+H]=270.24.

Intermediate 53. N³-((2-(Difluoromethyl)pyridin-4-yl)methyl)-1H-1,2,4-triazole-3,5-diamine

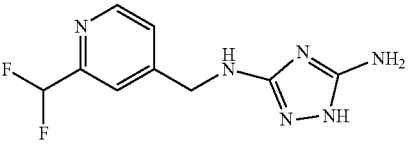 [SMILES: Nc1nc(NCc2ccnc(C(F)F)c2)n[nH]1]

¹H NMR (400 MHz, DMSO-d₆) δ=10.77-10.59 (m, 1H), 8.55 (d, J=5.1 Hz, 1H), 7.61 (s, 1H), 7.53-7.40 (m, 1H), 6.91 (t, J=0.1 Hz, 1H), 6.10 (br s, 1H), 5.65 (br s, 2H), 4.30 (br s, 2H); ¹⁹F NMR (376 MHz, DMSO-d₆) δ=−115.16 (d, J=1.0 Hz, 2F); [M+H]=241.4.

Intermediate 54. N³-((2,6-Dimethylpyridin-4-yl)methyl)-1H-1,2,4-triazole-3,5-diamine

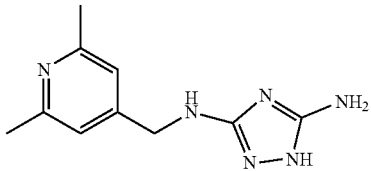 [SMILES: Cc1cc(CNc2n[nH]c(N)n2)cc(C)n1]

¹H NMR (400 MHz, DMSO-d₆) δ=10.74 (br s, 1H), 6.93 (s, 2H), 6.03 (br s, 1H), 5.45 (br s, 2H), 4.15 (d, J=6.3 Hz, 2H), 2.36 (s, 6H); [M+H]=219.4.

Intermediate 55. N³-(Quinolin-4-ylmethyl)-1H-1,2,4-triazole-3,5-diamine

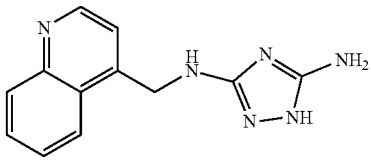 [SMILES: Nc1nc(NCc2ccnc3ccccc23)n[nH]1]

¹H NMR (400 MHz, DMSO-d₆) δ=10.80 (br s, 2H), 8.81 (d, J=4.3 Hz, 1H), 8.21-8.12 (m, 1H), 8.03 (dd, J=1.2, 8.6 Hz, 1H), 7.79-7.69 (m, 1H), 7.62 (ddd, J=1.6, 6.9, 8.3 Hz, 1H), 7.47-7.39 (m, 1H), 6.30 (br s, 1H), 5.42 (br s, 2H), 4.75 (d, J=6.3 Hz, 2H); [M+H]=241.4.

Intermediate 56. N³-((1-(2,2-Difluoroethyl)-3-methyl-1H-pyrazol-4-yl)methyl)-1H-1,2,4-triazole-3,5-diamine

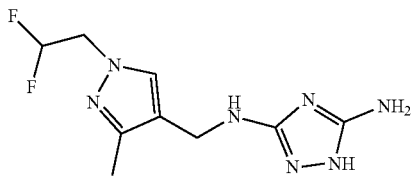 [SMILES: Cc1nn(CC(F)F)cc1CNc1n[nH]c(N)n1]

¹H NMR (400 MHz, DMSO-d₆) δ=11.12-10.29 (m, 2H), 7.53 (s, 1H), 6.45-6.09 (m, 2H), 5.68 (br s, 1H), 5.27 (br s, 2H), 4.45 (dt, J=3.9, 15.1 Hz, 2H), 3.99 (d, J=5.9 Hz, 2H), 2.12 (s, 3H); ¹⁹F NMR (376 MHz, DMSO-d₆) δ=-122.11--122.78 (m, 2F); [M+H]=258.4.

Intermediate 57. N³-((1-Isopropyl-3-methyl-1H-pyrazol-4-yl)methyl)-1H-1,2,4-triazole-3,5-diamine

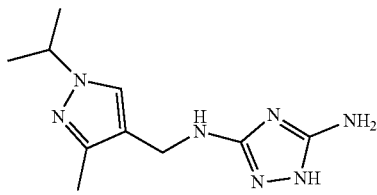 [SMILES: Cc1nn(C(C)C)cc1CNc1n[nH]c(N)n1]

¹H NMR (400 MHz, DMSO-d₆) δ=10.70 (br s, 1H), 5.27 (br s, 3H), 4.32 (td, J=6.7, 13.3 Hz, 1H), 3.97 (d, J=6.3 Hz, 2H), 2.10 (s, 3H), 1.33 (d, J=6.7 Hz, 6H); [M+H]=236.4.

Intermediate 58. N³-((1-Cyclopentyl-3-methyl-1H-pyrazol-4-yl)methyl)-1H-1,2,4-triazole-3,5-diamine

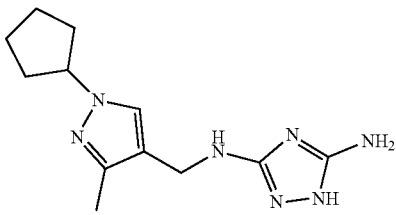 [SMILES: Cc1nn(C2CCCC2)cc1CNc1n[nH]c(N)n1]

¹H NMR (400 MHz, DMSO-d₆) δ=10.69 (br s, 1H), 5.80-5.48 (m, 1H), 5.25 (br s, 2H), 4.57-4.43 (m, 1H), 3.96 (d, J=5.9 Hz, 2H), 2.09 (s, 3H), 2.05-1.91 (m, 2H), 1.89-1.66 (m, 4H), 1.64-1.52 (m, 2H); [M+H]=262.4.

Intermediate 59. N³-((3,5-Difluoropyridin-4-yl)methyl)-1H-1,2,4-triazole-3,5-diamine

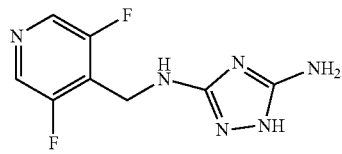 [SMILES: Nc1nc(NCc2c(F)cncc2F)n[nH]1]

¹H NMR (400 MHz, DMSO-d₆) δ=10.77 (br s, 1H), 8.44 (s, 2H), 5.90 (br s, 1H), 5.54 (br s, 2H), 4.33 (d, J=5.9 Hz, 2H); ¹⁹F NMR (376 MHz, DMSO-d₆) δ=-129.71 (s, 2F); [M+H]=227.4.

Intermediate 60. 3-(((5-Amino-1H-1,2,4-triazol-3-yl)amino)methyl)-4-fluorobenzonitrile

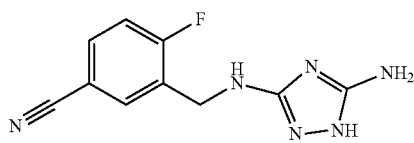 [SMILES: N#Cc1ccc(F)c(CNc2n[nH]c(N)n2)c1]

¹H NMR (400 MHz, DMSO-d₆) δ=10.79 (br s, 1H), 7.92-7.67 (m, 2H), 7.39 (t, J=9.6 Hz, 1H), 6.17 (br s, 1H), 5.53 (br s, 2H), 4.28 (d, J=6.3 Hz, 2H); ¹⁹F NMR (376 MHz, DMSO-d₆) δ=-109.35 (br s, 1F); [M+H]=233.4.

Intermediate 61. 7-Chloro-5-(fluoromethyl)-N-(4-methoxybenzyl)-[1,2,4]triazolo[1,5-a]pyrimidin-2-amine

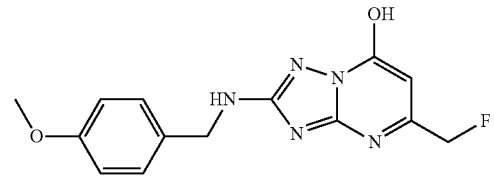 [SMILES: COc1ccc(CNc2nc3nc(CF)cc(O)n3n2)cc1]

Step 1. 5-(Fluoromethyl)-2-((4-methoxybenzyl)amino)-[1,2,4]triazolo[1,5-a]pyrimidin-7-ol. A solution of N³-(4-methoxybenzyl)-1H-1,2,4-triazole-3,5-diamine (Intermediate 1, 1.1 g, 5 mmol) in glacial acetic acid (15 mL) was treated with ethyl 4-fluoro-3-oxobutanoate (0.89 g, 12 mmol). The resulting mixture was heated at 70 to 80° C. for 20 h. The mixture was cooled to rt, evaporated to half-volume, and solids filtered. The collected precipitate was air dried to afford the title compound as a colorless solid (1.50 g, 99%). ¹H NMR (400 MHz, DMSO-d₆) δ=12.50 (br s, 1H), 7.35-7.10 (m, 3H), 6.85 (d, J=9.0 Hz, 2H), 5.91 (d, J=0.8 Hz, 1H), 5.45-5.09 (m, 2H), 4.31 (d, J=6.3 Hz, 2H), 3.70 (s, 3H); [M+H]=304.4.

Step 2. 7-Chloro-5-(fluoromethyl)-N-(4-methoxybenzyl)-[1,2,4]triazolo[1,5-a]pyrimidin-2-amine. The title compound was prepared in a manner analogous to Intermediate 3, Step 2, (15% yield); [M+H]=322.27.

Intermediate 62-Intermediate 75 were prepared in a manner analogous to Intermediate 3 with the appropriate starting material substitutions.

Intermediate 62. 7-Chloro-N-((2,3-dihydro-1H-inden-5-yl)methyl)-5-methyl-[1,2,4]triazolo[1,5-a]pyrimidin-2-amine

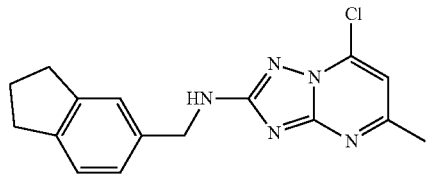 [SMILES: Cc1cc(Cl)n2nc(NCc3ccc4c(c3)CCC4)nc2n1]

¹H NMR (400 MHz, DMSO-d₆) δ=7.62-7.59 (t, 1H), 7.21 (s, 1H), 7.18 (s, 1H), 7.12-7.07 (m, 2H), 4.41-4.40 (d, 2H), 2.80-2.76 (m, 4H), 2.46 (s, 3H), 1.99-1.92 (m, 2H); [M+H]=314.1.

Intermediate 63. N-Benzyl-7-chloro-5-methyl-[1,2,4]triazolo[1,5-a]pyrimidin-2-amine

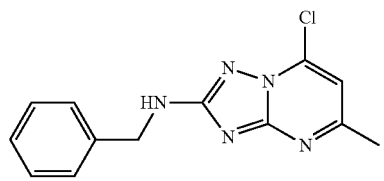 [SMILES: Cc1cc(Cl)n2nc(NCc3ccccc3)nc2n1]

¹H NMR (400 MHz, DMSO-d₆) δ=7.40-7.24 (m, 5H), 6.82 (s, 1H), 5.20-5.18 (br, 1H), 4.68-4.66 (d, 2H), 2.59 (s, 3H); [M+H]=274.1.

Intermediate 64. 7-Chloro-N-(3-(difluoromethyl)-4-methoxybenzyl)-5-methyl-[1,2,4]triazolo[1,5-a]pyrimidin-2-amine

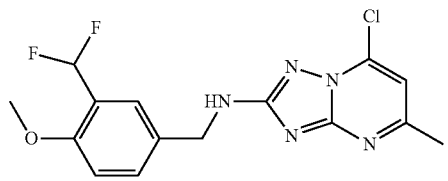

[M+H]=354.29.

Intermediate 65. 7-Chloro-N-(3-(difluoromethyl)benzyl)-5-methyl-[1,2,4]triazolo[1,5-a]pyrimidin-2-amine

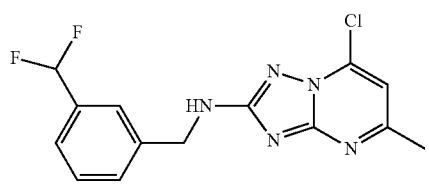 [SMILES: Cc1cc(Cl)n2nc(NCc3cccc(C(F)F)c3)nc2n1]

[M+H]=324.31.

Intermediate 66. 7-Chloro-5-methyl-N-((1-phenyl-1H-pyrazol-4-yl)methyl)-[1,2,4]triazolo[1,5-a]pyrimidin-2-amine

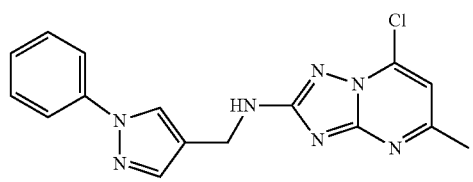 [SMILES: Cc1cc(Cl)n2nc(NCc3cnn(-c4ccccc4)c3)nc2n1]

[M+H]=340.22.

Intermediate 67. 7-Chloro-5-methyl-N-(3-methylbenzyl)-[1,2,4]triazolo[1,5-a]pyrimidin-2-amine

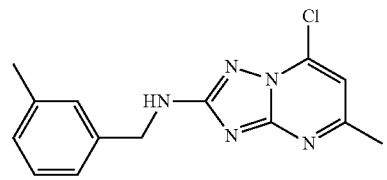 [SMILES: Cc1cccc(CNc2nc3nc(C)cc(Cl)n3n2)c1]

[M+H]=288.32.

Intermediate 68. 7-Chloro-N-((2,3-dihydrobenzo[b][1,4]dioxin-6-yl)methyl)-5-methyl-[1,2,4]triazolo[1,5-a]pyrimidin-2-amine

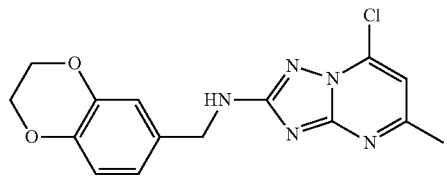 [SMILES: Cc1cc(Cl)n2nc(NCc3ccc4c(c3)OCCO4)nc2n1]

[M+H]=332.20.

Intermediate 69. 7-Chloro-N-(2,6-difluoro-4-methoxybenzyl)-5-methyl-[1,2,4]triazolo[1,5-a]pyrimidin-2-amine

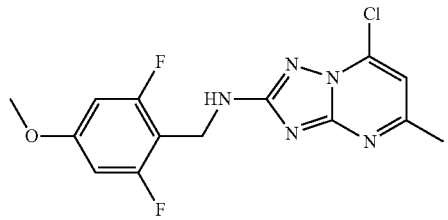

[M+H]=340.27.

Intermediate 70. 7-Chloro-N-(2-fluoro-5-methylbenzyl)-5-methyl-[1,2,4]triazolo[1,5-a]pyrimidin-2-amine

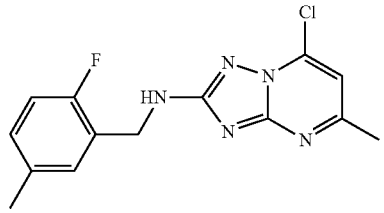 [SMILES: Cc1ccc(F)c(CNc2nc3nc(C)cc(Cl)n3n2)c1]

[M+H]=306.33.

Intermediate 71. 7-Chloro-N-(2-fluorobenzyl)-5-methyl-[1,2,4]triazolo[1,5-a]pyrimidin-2-amine

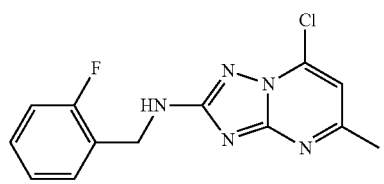 [SMILES: Cc1cc(Cl)n2nc(NCc3ccccc3F)nc2n1]

[M+H]=292.17.

Intermediate 72. 7-Chloro-N-(3-methoxybenzyl)-5-methyl-[1,2,4]triazolo[1,5-a]pyrimidin-2-amine

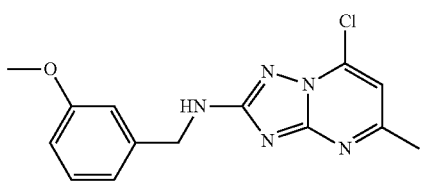

[M+H]=304.18.

Intermediate 73. 7-Chloro-N-((2,3-dihydrobenzofuran-5-yl)methyl)-5-methyl-[1,2,4]triazolo[1,5-a]pyrimidin-2-amine

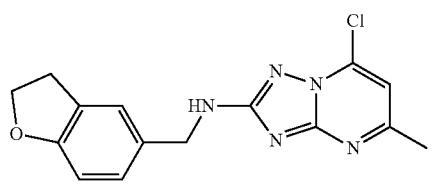 [SMILES: Cc1cc(Cl)n2nc(NCc3ccc4c(c3)CCO4)nc2n1]

[M+H]=316.19.

Intermediate 74. 7-Chloro-N-((2,3-dihydrobenzofuran-6-yl)methyl)-5-methyl-[1,2,4]triazolo[1,5-a]pyrimidin-2-amine

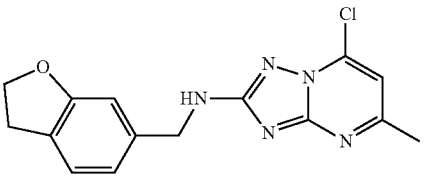 [SMILES: Cc1cc(Cl)n2nc(NCc3ccc4c(c3)OCC4)nc2n1]

[M+H]=316.33.

Intermediate 75. 7-Chloro-N-(3-chlorobenzyl)-5-methyl-[1,2,4]triazolo[1,5-a]pyrimidin-2-amine

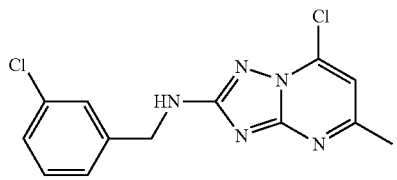 [SMILES: Cc1cc(Cl)n2nc(NCc3cccc(Cl)c3)nc2n1]

[M+H]=308.14.

Intermediate 76. 1-(Tetrahydro-2H-pyran-4-yl)but-2-yn-1-one

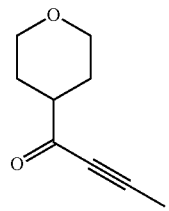

Step 1. N-Methoxy-N-methyltetrahydro-2H-pyran-4-carboxamide. N,N-diisopropylethylamine (8.1 mL, 46 mmol) was slowly added to a cold (0° C.) solution of tetrahydro-2H-pyran-4-carboxylic acid (2 g, 15 mmol) and O,N-Dimethyl-hydroxylamine hydrochloride (2.25 g, 23.05 mmol) in DCM (20 mL). To the above solution was added 2,4,6-tripropyl-1,3,5,2,4,6-trioxatriphosphinane 2,4,6-trioxide (11 mL, 50% w/w; 18.4 mmol) slowly while at 0° C. The mixture was warmed to rt and allowed to stir for 2 h. The reaction mixture was quenched with ice cubes then diluted with water (10 mL) and extracted with DCM (2×30 mL). The organic fractions were combined, washed with aq. sodium bicarbonate solution, dried ($Na_2SO_4$), filtered, and concentrated under reduced pressure to provide the title compound as an oily liquid (2.56 g, 96%). $^1$H NMR (400 MHz, $CD_3OD$) δ=3.96 (ddd, J=1.7, 4.0, 11.5 Hz, 2H), 3.75 (s, 3H), 3.49 (dt, J=2.4, 11.7 Hz, 2H), 3.19 (s, 3H), 3.10-2.92, (m, 1H), 1.83-1.60 (m, 4H); [M+H]=174.2.

Step 2. 1-(Tetrahydro-2H-pyran-4-yl)but-2-yn-1-one. A solution of N-methoxy-N-methyloxane-4-carboxamide (1 g, 5.8 mmol) in toluene (1.5 mL) was slowly added to a cooled (−15° C.) solution of prop-1-yn-1-ylmagnesium bromide (18 mL, 0.5 mol/L, 9.24 mmol). The reaction mixture was stirred at rt for 2 h, then cooled to 0° C. and an additional 0.5 eq of prop-1-yn-1-ylmagnesium bromide was added. The reaction mixture was warmed to room temperature and stirred overnight. The reaction was cooled to 0° C. and treated slowly with acetic acid (2.7 eq, 0.89 mL) in water (1.2 mL). The resulting gummy solid was stirred for 2 h. The reaction mixture was diluted with toluene and the organic layers were separated. The organic layer was extracted with water then brine. The combined organics were dried (Na$_2$SO$_4$), filtered, and concentrated under reduced pressure to provide the title compound as an oil (0.787 g, 89%) which was used crude without further purification. $^1$H NMR (400 MHz, CDCl$_3$) δ=4.06-3.95 (m, 2H), 3.50-3.39 (m, 2H), 2.64-2.54 (m, 1H), 2.07-2.03 (m, 3H), 1.96-1.86 (m, 2H), 1.84-1.72 (m, 2H); [M+H]=153.12.

EXAMPLES

Example 1. N-(4-Methoxybenzyl)-5-methyl-7-(tetrahydro-2H-pyran-4-yl)-[1,2,4]triazolo[1,5-a]pyrimidin-2-amine

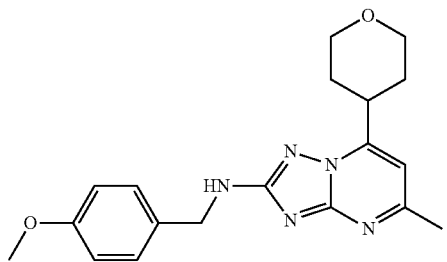

Method A.

Step 1. 7-(3,6-Dihydro-2H-pyran-4-yl)-N-(4-methoxybenzyl)-5-methyl-[1,2,4]triazolo[1,5-a]pyrimidin-2-amine. A solution of 7-chloro-N-(4-methoxybenzyl)-5-methyl-[1,2,4]triazolo[1,5-a]pyrimidin-2-amine (Intermediate 3, 152 mg, 0.5 mmol) in 1,4-dioxane (5 mL) and water (2 mL) was treated with Cs$_2$CO$_3$ (325 mg, 1 mmol) and 2-(3,6-dihydro-2H-pyran-4-yl)-4,4,5,5-tetramethyl-1,3,2-dioxaborolane (158 mg, 0.75 mmol) and the reaction mixture purged with nitrogen for 3 minutes. After this time Pd(dppf)Cl$_2$.DCM adduct (20 mg, 0.03 mmol) was added and the mixture was heated at 90° C. for 10 minutes. The reaction mixture was cooled, evaporated to a small volume, and partitioned between water and EtOAc. The organic portion was dried (MgSO$_4$), filtered, and concentrated under reduced pressure. Purification (FCC, SiO$_2$, EtOAc then 10% MeOH/EtOAc) provided the title compound (83 mg, 47%); [M+H]=352.35.

Step 2. N-(4-Methoxybenzyl)-5-methyl-7-(tetrahydro-2H-pyran-4-yl)-[1,2,4]triazolo[1,5-a]pyrimidin-2-amine. A solution of 7-(3,6-dihydro-2H-pyran-4-yl)-N-(4-methoxybenzyl)-5-methyl-[1,2,4]triazolo[1,5-a]pyrimidin-2-amine (165 mg, 0.47 mmol) in nitrogen purged MeOH (10 mL) and EtOAc (10 mL) was treated with 20% palladium hydroxide on carbon (150 mg) then hydrogenated on a Hydrogen Parr at 50-60 psi hydrogen for 8 h. The reaction mixture was then filtered though a plug of CELITE® with the aid of EtOAc and the solvent was evaporated. Purification (FCC, SiO$_2$, EtOAc-10% MeOH/EtOAc) afforded the title compound as an off-white solid (136 mg, 82%). $^1$H NMR (400 MHz, DMSO-d$_6$) δ=7.36 (t, J=6.5 Hz, 1H), 7.28 (d, J=8.6 Hz, 2H), 6.89-6.80 (m, 3H), 4.36 (d, J=6.3 Hz, 2H), 4.01-3.94 (m, 2H), 3.70 (s, 3H), 3.54-3.37 (m, 3H), 2.47 (s, 3H), 1.97-1.89 (m, 2H), 1.74 (dq, J=4.5, 12.3 Hz, 2H); [M+H]=354.40.

Method B.

A solution of N$^3$-(4-methoxybenzyl)-1H-1,2,4-triazole-3,5-diamine (Intermediate 1, 386 mg, 1.76 mmol) in AcOH (5 mL) was treated with 1-(tetrahydro-2H-pyran-4-yl)butane-1,3-dione (Intermediate 4, 330 mg, 1.94 mmol) and the mixture heated at 80° C. for 2 h. The reaction mixture was concentrated under reduced pressure. Purification (FCC, SiO$_2$, EtOAc-10% MeOH/EtOAc) afforded the title compound which was recrystallized from EtOAc to remove traces of undesired regioisomer, to provide the title compound as a colorless solid (623 mg, 86%). $^1$H NMR (400 MHz, DMSO-d$_6$) δ=7.35 (t, J=6.3 Hz, 1H), 7.28 (d, J=8.6 Hz, 2H), 6.87-6.81 (m, 3H), 4.36 (d, J=6.3 Hz, 2H), 4.01-3.94 (m, 2H), 3.70 (s, 3H), 3.49 (dt, J=1.8, 11.8 Hz, 2H), 3.45-3.37 (m, 1H), 2.47 (s, 3H), 1.93 (dd, J=1.6, 12.5 Hz, 2H), 1.74 (dq, J=4.5, 12.3 Hz, 2H); [M+H]=354.43.

Example 2. 7-Cyclopropyl-N-((2,3-dihydrobenzofuran-5-yl)methyl)-5-methyl-[1,2,4]triazolo[1,5-a]pyrimidin-2-amine

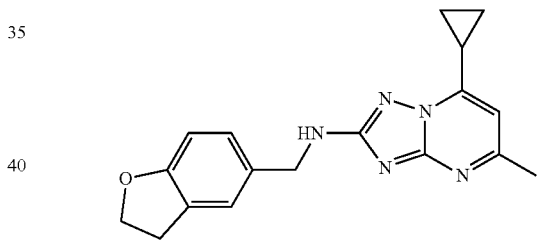

A solution of 7-chloro-N-((2,3-dihydrobenzofuran-5-yl)methyl)-5-methyl-[1,2,4]triazolo[1,5-a]pyrimidin-2-amine (Intermediate 73, 200 mg, 0.63 mmol), cyclopropylboronic acid (60 mg, 0.7 mmol), and potassium carbonate (263 mg, 1.9 mmol) in THF (2 mL) was purged with a stream of nitrogen for 10 min and Pd(dppf)Cl$_2$.DCM adduct (51.7 mg, 0.06 mmol) was added. The reaction mixture was allowed to stir at 100° C. for 3 days. The mixture was then diluted with EtOAc and water and the organic portion was washed with brine, dried (MgSO$_4$), filtered, and concentrated under reduced pressure. Purification (FCC, SiO$_2$, 20-100% EtOAc/hexanes) afforded the title compound as a light yellow solid. The title compound was recrystallized from EtOAc to provide an off-white solid which was recrystallized from MeOH to afford the title compound as a colorless solid (45 mg, 22% yield). $^1$H NMR (400 MHz, CDCl$_3$) δ=7.17-7.10 (m, 1H), 6.73 (d, J=8.2 Hz, 1H), 6.17 (s, 1H), 4.85 (t, J=6.1 Hz, 1H), 4.59-4.51 (m, 4H), 3.18 (t, J=8.8 Hz, 2H), 2.68-2.54 (m, 1H), 2.53-2.49 (m, 3H), 1.33-1.26 (m, 2H), 1.13-1.06 (m, 2H); [M+H]=322.17.

Example 3. 7-Cyclopropyl-N-((2,3-dihydrobenzofuran-6-yl)methyl)-5-methyl-[1,2,4]triazolo[1,5-a]pyrimidin-2-amine

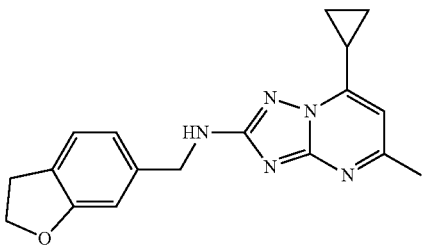 [SMILES: Cc1cc(C2CC2)n2nc(NCc3ccc4c(c3)OCC4)nc2n1]

A solution of 7-chloro-N-((2,3-dihydrobenzofuran-6-yl)methyl)-5-methyl-[1,2,4]triazolo[1,5-a]pyrimidin-2-amine (Intermediate 74, 200 mg, 0.63 mmol), cyclopropylboronic acid (60 mg, 0.7 mmol), and potassium carbonate (263 mg, 1.9 mmol) in THF (2 mL) was purged with a stream of nitrogen for 10 min and Pd(dppf)Cl$_2$.DCM (52 mg, 0.06 mmol) was added. The reaction mixture was allowed to stir at 90° C. for 16 h then 100° C. for 24 h. The mixture was diluted with EtOAc and water and the organic portion isolated and washed with brine, dried (MgSO$_4$), filtered, and concentrated under reduced pressure. Purification (FCC, SiO$_2$, 10-100% of 10% MeOH in DCM/DCM) then again (FCC, SiO$_2$, 10-75% of 10% MeOH in DCM/DCM) afforded the title compound as a light yellow solid. Recrystallization in EtOAc afforded the title compound as a light yellow/beige crystalline solid (38 mg, 19% yield). $^1$H NMR (400 MHz, CDCl$_3$) δ=7.13 (d, J=7.4 Hz, 1H), 6.88 (dd, J=1.4, 7.6 Hz, 1H), 6.85 (s, 1H), 6.16 (s, 1H), 4.90 (t, J=6.1 Hz, 1H), 4.61-4.51 (m, 4H), 3.17 (t, J=8.6 Hz, 2H), 2.67-2.56 (m, 1H), 2.53-2.50 (m, 3H), 1.32-1.26 (m, 2H), 1.13-1.06 (m, 2H); [M+H]=322.16.

Example 4. 7-Cyclopropyl-N-(4-methoxybenzyl)-5-methyl-[1,2,4]triazolo[1,5-a]pyrimidin-2-amine

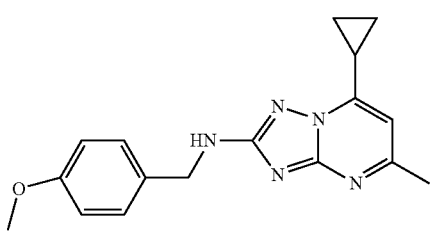

A solution of 7-chloro-N-(4-methoxybenzyl)-5-methyl-[1,2,4]triazolo[1,5-a]pyrimidin-2-amine (Intermediate 3, 200 mg, 0.66 mmol), cyclopropylboronic acid (62 mg, 0.72 mmol), and potassium carbonate (263 mg, 1.9 mmol) in THF (2 mL) was purged with a stream of nitrogen for 10 min and Pd(dppf)Cl$_2$.DCM (54 mg, 0.07 mmol) was added. The reaction mixture was allowed to stir at 90° C. for 16 h. The mixture was diluted with EtOAc and water and the organic portion isolated and washed with brine, dried (MgSO$_4$), filtered, and concentrated under reduced pressure. Purification (FCC, SiO$_2$, 50-100% EtOAc/hexanes) then re-purification (FCC, SiO$_2$, 10-75% of a solution of 10% MeOH in DCM/DCM) provided the title compound as a foamy solid. Further purification (mass-directed RP HPLC chromatography, CH$_3$CN/water; with formic acid as the modifier) afforded the title compound. The pure fractions were basified with a few drops of ammonia hydroxide and concentrated to afford the title compound as a colorless solid (37 mg, 18% yield). $^1$H NMR (400 MHz, CDCl$_3$) δ=7.36-7.31 (m, 2H), 6.89-6.83 (m, 2H), 6.17 (s, 1H), 4.89 (t, J=5.9 Hz, 1H), 4.57 (d, J=5.9 Hz, 2H), 3.81-3.78 (m, 3H), 2.68-2.57 (m, 1H), 2.51 (s, 3H), 1.33-1.25 (m, 2H), 1.13-1.07 (m, 2H); [M+H]=309.87.

Example 5. 7-Cyclopentyl-N-((2,3-dihydro-1H-inden-5-yl)methyl)-5-methyl-[1,2,4]triazolo[1,5-a]pyrimidin-2-amine

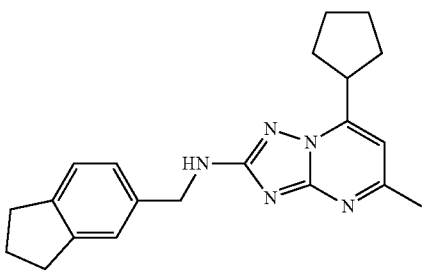 [SMILES: Cc1cc(C2CCCC2)n2nc(NCc3ccc4c(c3)CCC4)nc2n1]

A suspension of 7-chloro-N-((2,3-dihydro-1H-inden-5-yl)methyl)-5-methyl-[1,2,4]triazolo[1,5-a]pyrimidin-2-amine (Intermediate 62, 157 mg, 0.5 mmol) and copper(I) iodide (95 mg, 0.5 mmol) in THF (2 mL) was cooled to 0-5° C. in an ice bath and treated drop-wise with cyclopentylmagnesium bromide (1 mL, 2 mol/L, 2 mmol). After 2 h the reaction mixture was treated with a saturated aqueous solution of NH$_4$Cl (2 mL) and EtOAc (10 mL). The organic portion was separated and washed with brine (2×10 mL), dried (MgSO$_4$), filtered, and concentrated under reduced pressure. Purification (FCC, SiO$_2$, 50%-100% EtOAc/hexanes) afforded the title compound as a brown colored oil (54 mg, 31% yield). $^1$H NMR (400 MHz, CDCl$_3$) δ=7.31-7.25 (m, 1H), 7.16 (s, 2H), 6.55 (s, 1H), 5.12 (br s, 1H), 4.59 (d, J=5.5 Hz, 2H), 3.62 (quin, J=8.0 Hz, 1H), 2.87 (t, J=7.2 Hz, 4H), 2.55 (s, 3H), 2.29-2.18 (m, 2H), 2.05 (quin, J=7.4 Hz, 2H), 1.89-1.64 (m, 6H); [M+H]=348.26.

Example 6. N-((2,3-Dihydro-1H-inden-5-yl)methyl)-7-isopropyl-5-methyl-[1,2,4]triazolo[1,5-a]pyrimidin-2-amine

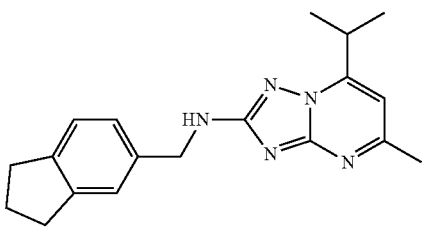 [SMILES: Cc1cc(C(C)C)n2nc(NCc3ccc4c(c3)CCC4)nc2n1]

A suspension of 7-chloro-N-((2,3-dihydro-1H-inden-5-yl)methyl)-5-methyl-[1,2,4]triazolo[1,5-a]pyrimidin-2-amine (Intermediate 62, 157 mg, 0.5 mmol) and copper(I) iodide (95.2 mg, 0.5 mmol) in THF (2 mL) was cooled to 0-5° C. in an ice bath and treated drop-wise with isopropy- 1magnesium bromide (1 mL, 2.0 mol/L, 2.0 mmol). After 2 h the mixture was treated with a saturated aqueous solution of NH$_4$Cl (2 mL) and EtOAc (10 mL). The organic portion was separated and washed with brine (2×10 mL), dried (MgSO$_4$), filtered, and concentrated under reduced pressure. Purification (FCC, SiO$_2$, 50% then 100% EtOAc/hexanes) afforded the title compound as an impure (~80% purity by LC/MS analysis) brown colored oil. Impure product was further purified by mass-directed RP HPLC chromatography (CH$_3$CN/water) with formic acid as the modifier to afford the title compound as a semi-solid (2.5 mg, 1.6% yield); [M+H]=322.26.

Example 7. N-(3-Chlorobenzyl)-7-isopropyl-5-methyl-[1,2,4]triazolo[1,5-a]pyrimidin-2-amine

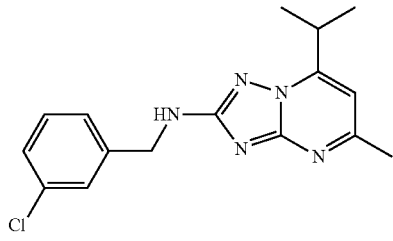 [SMILES: Cc1cc(C(C)C)n2nc(NCc3cccc(Cl)c3)nc2n1]

A suspension of 7-chloro-N-(3-chlorobenzyl)-5-methyl-[1,2,4]triazolo[1,5-a]pyrimidin-2-amine (Intermediate 75, 308 mg, 1 mmol) and copper(I) iodide (191 mg, 1 mmol) in THF (5 mL) at −10° C. was treated drop-wise with isopropylmagnesium chloride (3 mL, 2 mol/L, 6 mmol) and allowed to stir 1 h after which time a saturated aqueous solution of NH$_4$Cl (3 mL) was added. The reaction mixture was diluted with EtOAc (10 mL) and the organic portion washed with brine (2×10 mL) then dried (MgSO$_4$), filtered, and concentrated under reduced pressure. Purification (FCC, SiO$_2$, EtOAc) afforded the title compound which was then triturated with a 50% EtOAc/hexanes solution. The resulting solids were air dried to afford the title compound as a pale yellow crystalline solid (20 mg, 6% yield). $^1$H NMR (400 MHz, CDCl$_3$) δ=7.42 (s, 1H), 7.32-7.19 (m, 3H), 6.55 (s, 1H), 5.17 (d, J=5.5 Hz, 1H), 4.62 (d, J=6.3 Hz, 2H), 3.56 (td, J=7.0, 13.8 Hz, 1H), 2.57 (s, 3H), 1.37 (d, J=7.0 Hz, 6H); [M+H]=316.23.

Example 8. N-Benzyl-7-isopropyl-5-methyl-[1,2,4]triazolo[1,5-a]pyrimidin-2-amine

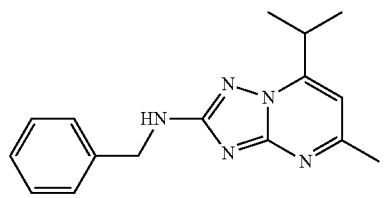 [SMILES: Cc1cc(C(C)C)n2nc(NCc3ccccc3)nc2n1]

A suspension of N-benzyl-7-chloro-5-methyl-[1,2,4]triazolo[1,5-a]pyrimidin-2-amine (Intermediate 63, 274 mg, 1 mmol) and copper(I)iodide (191 mg, 1 mmol) in THF (5 mL) was cooled to 0-5° C. in an ice bath and treated drop-wise with isopropylmagnesium chloride (3 mL, 2 mol/L, 6 mmol). After 2 h the reaction mixture was treated with a saturated aqueous solution of NH$_4$Cl (2 mL) and EtOAc (10 mL). The organic portion was separated and washed with brine (2×10 mL), dried (MgSO$_4$), filtered, and concentrated under reduced pressure. Purification (FCC, SiO$_2$, 80% EtOAc/hexanes) afforded the title compound which was then triturated with a 20% EtOAc/hexanes solution to afford the title compound as a pale yellow solid (65 mg, 23% yield). $^1$H NMR (400 MHz, CDCl$_3$) δ=7.41 (d, J=7.0 Hz, 2H), 7.32 (t, J=7.2 Hz, 2H), 7.28-7.21 (m, 1H), 6.54 (s, 1H), 5.01 (t, J=5.5 Hz, 1H), 4.64 (d, J=6.3 Hz, 2H), 3.58 (td, J=6.8, 13.7 Hz, 1H), 2.57 (s, 3H), 1.37 (d, J=7.0 Hz, 6H); [M+H]=282.22.

Example 9. 7-(tert-Butyl)-N-(3-chlorobenzyl)-5-methyl-[1,2,4]triazolo[1,5-a]pyrimidin-2-amine

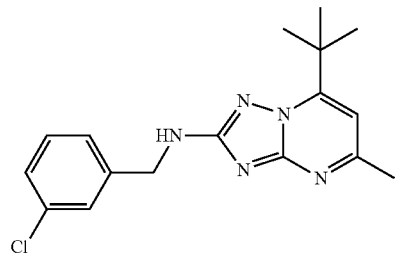 [SMILES: Cc1cc(C(C)(C)C)n2nc(NCc3cccc(Cl)c3)nc2n1]

A suspension of 7-chloro-N-(3-chlorobenzyl)-5-methyl-[1,2,4]triazolo[1,5-a]pyrimidin-2-amine (Intermediate 75, 308 mg, 1.0 mmol) and copper(I)iodide (191 mg, 1 mmol) in THF (5 mL) at −10° C. was treated drop-wise with tert-butylmagnesium chloride (3 mL, 2 mol/L, 6 mmol) and allowed to stir 1 h. To the reaction mixture was added a saturated aqueous solution of NH$_4$Cl (3 mL). The reaction mixture was diluted with EtOAc (10 mL) and the organic portion washed with brine (2×10 mL) then dried (MgSO$_4$), filtered, and concentrated under reduced pressure. Purification (FCC, SiO$_2$, 100% EtOAc) afforded a pale yellow crystalline product which was triturated with a 50% EtOAc/hexanes solution (7 mg, 2% yield). $^1$H NMR (400 MHz, CDCl$_3$) δ=7.43 (s, 1H), 7.32-7.19 (m, 3H), 6.57 (s, 1H), 5.05 (br s, 1H), 4.60 (d, J=5.9 Hz, 2H), 2.57 (s, 3H), 1.52 (s, 9H); [M+H]=330.24.

Example 10. 7-Isopropyl-N-(4-methoxybenzyl)-5-methyl-[1,2,4]triazolo[1,5-a]pyrimidin-2-amine

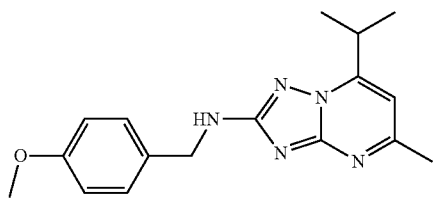

A suspension of 7-chloro-N-(4-methoxybenzyl)-5-methyl-[1,2,4]triazolo[1,5-a]pyrimidin-2-amine (Intermediate 3, 152 mg, 0.5 mmol) and Fe(acac)$_3$ (18 mg, 0.05 mmol) in a mixture of THF (1 mL) and NMP (100 µL) at 0-5° C. was treated with isopropylmagnesium chloride (1.5 mL, 2 mol/L, 3 mmol) and stirred for 1 h. The reaction mixture was quenched treated with a saturated aqueous solution of NH₄Cl (3 mL) and EtOAc (5 mL). The organic portion was further washed with brine (2×5 mL), dried (MgSO₄), filtered, and concentrated under reduced pressure. Purification (FCC, SiO₂, EtOAc) afforded the title compound as yellow-colored foam (39 mg, 25% yield). ¹H NMR (400 MHz, CDCl₃) δ=7.34 (d, J=8.6 Hz, 2H), 6.86 (d, J=8.6 Hz, 2H), 6.55 (s, 1H), 4.95 (t, J=5.9 Hz, 1H), 4.57 (d, J=5.9 Hz, 2H), 3.79 (s, 3H), 3.59 (td, J=6.8, 13.7 Hz, 1H), 2.57 (s, 3H), 1.38 (d, J=7.0 Hz, 6H); [M+H]=312.27.

Example 11. 7-(sec-butyl)-N-(4-Methoxybenzyl)-5-methyl-[1,2,4]triazolo[1,5-a]pyrimidin-2-amine

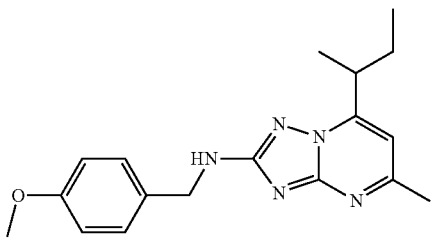

A suspension of 7-chloro-N-(4-methoxybenzyl)-5-methyl-[1,2,4]triazolo[1,5-a]pyrimidin-2-amine (Intermediate 3, 152 mg, 0.5 mmol) and Fe(acac)₃ (18 mg, 0.05 mmol) in a mixture of THF (1 mL) and NMP (100 µL) at 0-5° C. was treated with isobutylmagnesium chloride (1.25 mL, 2 mol/L, 2.5 mmol) and stirred for 1 h. The reaction mixture was quenched with a saturated aqueous solution of NH₄Cl (3 mL) and EtOAc (5 mL). The organic portion was further washed with brine (2×5 mL), dried (MgSO₄), filtered, and concentrated under reduced pressure. Purification (FCC, SiO₂, EtOAc) afforded the title compound as yellow-colored foam (40 mg, 25% yield). ¹H NMR (400 MHz, CDCl₃) δ=7.33 (d, J=8.6 Hz, 2H), 6.85 (d, J=8.6 Hz, 2H), 6.51 (s, 1H), 4.98 (t, J=5.9 Hz, 1H), 4.55 (d, J=6.3 Hz, 2H), 3.78 (s, 3H), 3.42 (sxt, J=6.9 Hz, 1H), 2.56 (s, 3H), 1.94-1.80 (m, 1H), 1.68 (td, J=7.4, 13.7 Hz, 1H), 1.34 (d, J=7.0 Hz, 3H), 0.93 (t, J=7.4 Hz, 3H); [M+H]=326.30.

Example 12. N-(4-Methoxybenzyl)-5-methyl-7-(tetrahydrofuran-2-yl)-[1,2,4]triazolo[1,5-a]pyrimidin-2-amine

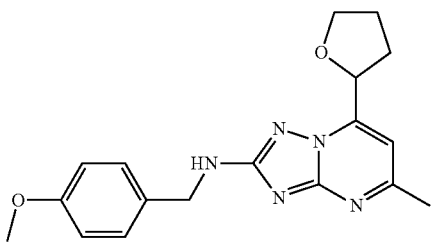

A solution of 7-chloro-N-(4-methoxybenzyl)-5-methyl-[1,2,4]triazolo[1,5-a]pyrimidin-2-amine (Intermediate 3, 61 mg, 0.2 mmol) and Pd(PPh₃)₄ (5.8 mg, 0.01 mmol) in a mixture of THF (2 mL) was treated with cyclobutylzinc(II) bromide (1.2 mL, 0.5 mol/L, 0.6 mmol) and stirred for 4 h at 50° C. The reaction was then cooled and treated with half-saturated brine solution (5 mL) and EtOAc (10 mL). The organic portion was further washed with brine (10 mL). The organic portion was dried (MgSO₄), filtered, and concentrated under reduced pressure. Purification (FCC, SiO₂, EtOAc) then (FCC, SiO₂, 10% MeOH/EtOAc) afforded the title compound as a pale-yellow foam (19 mg, 28% yield). ¹H NMR (400 MHz, CDCl₃) δ=7.30 (d, J=9.0 Hz, 2H), 6.84 (d, J=8.6 Hz, 2H), 5.96 (s, 1H), 5.00-4.84 (m, 2H), 4.58 (d, J=5.9 Hz, 2H), 3.77 (s, 3H), 2.61-2.50 (m, 6H), 2.49-2.39 (m, 2H), 2.02-1.91 (m, 1H), 1.82-1.68 (m, 1H); [M+H]=340.28.

Example 13. N-(5-Chloro-2-fluorobenzyl)-5-methyl-7-(tetrahydro-2H-pyran-4-yl)-[1,2,4]triazolo[1,5-a]pyrimidin-2-amine

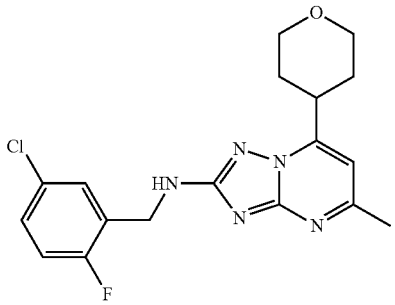 [SMILES: Cc1cc(C2CCOCC2)n2nc(NCc3cc(Cl)ccc3F)nc2n1]

A mixture of 2-bromo-5-methyl-7-(tetrahydro-2H-pyran-4-yl)-[1,2,4]triazolo[1,5-a]pyrimidine (Intermediate 5, 51 mg, 0.17 mmol) and (5-chloro-2-fluorophenyl)methanamine (220 mg, 1.38 mmol) were heated at 150° C. in a sand-bath to form a melt which was then subjected to microwave irradiation at 200° C. for 25 min. The cooled mixture was dissolved in DCM, washed with water, dried (MgSO₄), filtered, and concentrated under reduced pressure. The resulting solid was crystallized from MeOH to afford the title compound as a colorless solid (30 mg, 46%). ¹H NMR (400 MHz, CDCl₃) δ=7.48 (dd, J=2.5, 6.5 Hz, 1H), 7.18 (ddd, J=2.7, 4.4, 8.5 Hz, 1H), 7.01-6.94 (m, 1H), 6.54 (s, 1H), 5.15 (t, J=6.5 Hz, 1H), 4.63 (d, J=6.3 Hz, 2H), 4.13 (dd, J=3.9, 11.3 Hz, 2H), 3.64 (dt, J=2.0, 11.9 Hz, 2H), 3.56-3.47 (m, 1H), 2.58 (s, 3H), 2.04 (dd, J=2.0, 12.5 Hz, 2H), 1.87-1.75 (m, 2H); [M+H]=376.1.

Example 14. N-[(3,5-Difluorophenyl)methyl]-5-methyl-7-(oxan-4-yl)-[1,2,4]triazolo[1,5-a]pyrimidin-2-amine

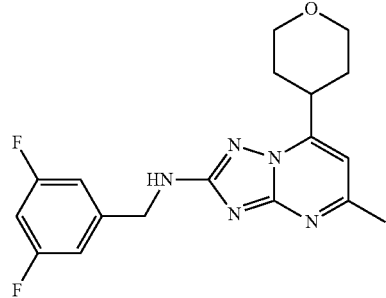 [SMILES: Cc1cc(C2CCOCC2)n2nc(NCc3cc(F)cc(F)c3)nc2n1]

To a solution of 1-(tetrahydro-2H-pyran-4-yl)but-2-yn-1-one (Intermediate 76, 210 mg, 1.38 mmol) in EtOH (0.63 mL) was added pyrrolidine (115 µL, 1.38 mmol). The reaction mixture was stirred for 15 minutes, then a solution of N$^3$-(3,5-difluorobenzyl)-1H-1,2,4-triazole-3,5-diamine (Intermediate 37, 326 mg, 1.45 mmol) in acetic acid (1.18 mL, 20.7 mmol) was added. The reaction mixture was heated to 55° C. for 1 h. The temperature was increased to 80° C. and water (4 mL) was added. To the resulting precipitate was added water until all the precipitate went back into solution. The reaction mixture cooled to room temperature. The resulting precipitate was collected and washed with water, and then heptanes. The crude title compound was recrystallized from isopropylacetate (10 mL) to afford the title compound (280 mg, 56%) as an off-white crystalline solid. $^1$H NMR (400 MHz, CDCl$_3$) δ=7.00-6.92 (m, 2H), 6.70 (tt, J=2.3, 8.9 Hz, 1H), 6.57 (s, 1H), 5.19 (t, J=6.4 Hz, 1H), 4.64 (d, J=6.5 Hz, 2H), 4.14 (dd, J=3.9, 11.4 Hz, 2H), 3.68-3.60 (m, 2H), 3.52 (tt, J=3.5, 12.0 Hz, 1H), 2.61 (s, 3H), 2.63-2.59 (m, 3H), 2.08-2.01 (m, 2H), 1.83 (dq, J=4.4, 12.4 Hz, 2H); [M+H]=360.2.

Example 15-Example 30 were prepared in a manner analogous to Example 1, Method A, with the appropriate starting material substitutions.

Example 15. N-[(2-Fluoro-4-methoxyphenyl)methyl]-5-methyl-7-(oxan-4-yl)-[1,2,4]triazolo[1,5-a]pyrimidin-2-amine

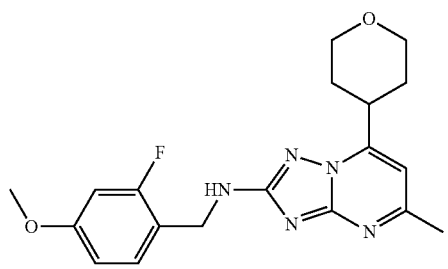

$^1$H NMR (400 MHz, DMSO-d$_6$) δ=7.40-7.28 (m, 2H), 6.83 (s, 1H), 6.75 (dd, J=2.7, 12.1 Hz, 1H), 6.69 (dd, J=2.3, 8.6 Hz, 1H), 4.38 (d, J=6.3 Hz, 2H), 3.97 (dd, J=3.1, 11.3 Hz, 2H), 3.71 (s, 3H), 3.48 (dt, J=1.8, 11.8 Hz, 2H), 3.43-3.34 (m, 1H), 2.46 (s, 3H), 1.96-1.86 (m, 2H), 1.71 (dq, J=4.3, 12.4 Hz, 2H); [M+H]=372.42.

Example 16. N-(2,3-Dihydro-1,4-benzodioxin-6-ylmethyl)-5-methyl-7-(oxan-4-yl)-[1,2,4]triazolo[1,5-a]pyrimidin-2-amine

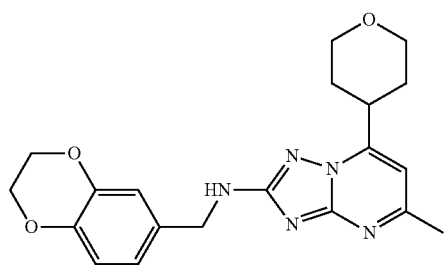 [SMILES: Cc1cc(C2CCOCC2)n2nc(NCc3ccc4c(c3)OCCO4)nc2n1]

$^1$H NMR (400 MHz, DMSO-d$_6$) δ=7.37 (t, J=6.5 Hz, 1H), 6.89-6.68 (m, 4H), 4.30 (d, J=6.3 Hz, 2H), 4.18 (s, 4H), 3.98 (dd, J=3.3, 11.2 Hz, 2H), 3.56-3.37 (m, 3H), 2.47 (s, 3H), 1.99-1.89 (m, 2H), 1.73 (dq, J=4.3, 12.3 Hz, 2H); [M+H]=382.41.

Example 17. 5-Methyl-7-(oxan-4-yl)-N-[(1-phenyl-1H-pyrazol-4-yl)methyl]-[1,2,4]triazolo[1,5-a]pyrimidin-2-amine

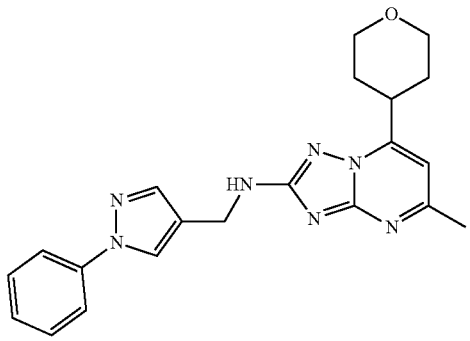 [SMILES: Cc1cc(C2CCOCC2)n2nc(NCc3cnn(-c4ccccc4)c3)nc2n1]

$^1$H NMR (400 MHz, DMSO-d$_6$) δ=8.39 (s, 1H), 7.79-7.73 (m, 2H), 7.70 (s, 1H), 7.45 (dd, J=7.4, 8.6 Hz, 2H), 7.30-7.19 (m, 2H), 6.86 (s, 1H), 4.36 (d, J=5.9 Hz, 2H), 3.95 (dd, J=3.5, 11.3 Hz, 2H), 3.56-3.39 (m, 3H), 2.47 (s, 3H), 1.93 (dd, J=1.6, 12.5 Hz, 2H), 1.74 (dq, J=4.7, 12.4 Hz, 2H); [M+H]=390.42.

Example 18. 1-[4-(2-[(4-Methoxyphenyl)methyl]amino-5-methyl-[1,2,4]triazolo[1,5-a]pyrimidin-7-yl)piperidin-1-yl]ethan-1-one

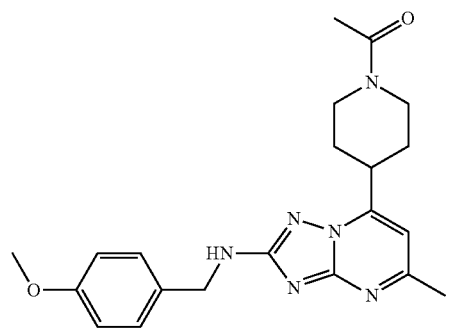

$^1$H NMR (400 MHz, DMSO-d$_6$) δ=7.37 (t, J=6.5 Hz, 1H), 7.29 (d, J=8.6 Hz, 2H), 6.91-6.78 (m, 3H), 4.55 (d, J=13.3 Hz, 1H), 4.37 (d, J=6.3 Hz, 2H), 3.96 (d, J=13.7 Hz, 1H), 3.71 (s, 3H), 3.43 (tt, J=3.3, 11.9 Hz, 1H), 3.26-3.13 (m, 1H), 2.71-2.59 (m, 1H), 2.46 (s, 3H), 2.08-1.94 (m, 5H), 1.67 (dq, J=4.1, 12.5 Hz, 1H), 1.52 (dq, J=4.1, 12.5 Hz, 1H); [M+H]=395.41.

Example 19. 1-{4-[2-({[3-(Difluoromethyl)-4-methoxyphenyl]methyl}amino)-5-methyl-[1,2,4]triazolo[1,5-a]pyrimidin-7-yl]piperidin-1-yl}ethan-1-one

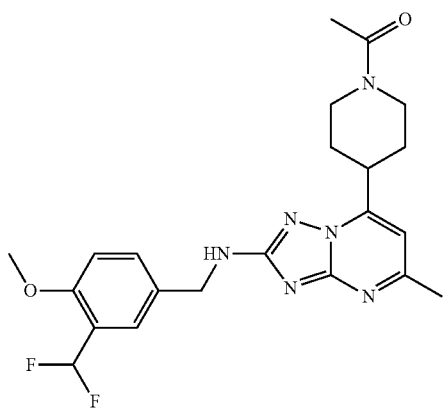

¹H NMR (400 MHz, DMSO-d₆) δ=7.57-7.42 (m, 3H), 7.09 (d, J=8.6 Hz, 1H), 7.05 (t, J=56.0 Hz, 1H), 6.84 (s, 1H), 4.55 (d, J=12.9 Hz, 1H), 4.40 (d, J=6.7 Hz, 2H), 3.96 (d, J=13.7 Hz, 1H), 3.81 (s, 3H), 3.43 (tt, J=3.5, 12.0 Hz, 1H), 3.25-3.14 (m, 1H), 2.71-2.59 (m, 1H), 2.46 (s, 3H), 2.09-1.94 (m, 5H), 1.67 (dq, J=4.3, 12.4 Hz, 1H), 1.51 (dq, J=4.5, 12.5 Hz, 1H); [M+H]=445.42.

Example 20. 1-{4-[2-({[3-(Difluoromethyl)phenyl]methyl}amino)-5-methyl-[1,2,4]triazolo[1,5-a]pyrimidin-7-yl]piperidin-1-yl}ethan-1-one

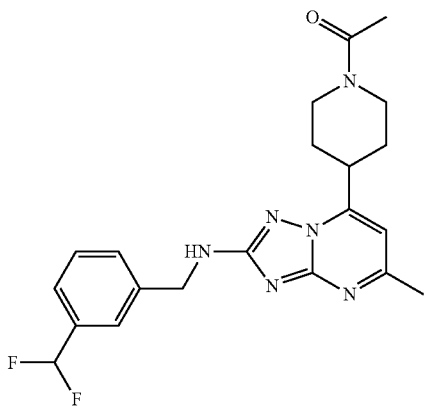 [SMILES: CC(=O)N1CCC(c2cc(C)nc3nc(NCc4cccc(C(F)F)c4)nn23)CC1]

[M+H]=415.40.

Example 21. N-[(3-Chloro-4-methoxyphenyl)methyl]-5-methyl-7-(oxan-4-yl)-[1,2,4]triazolo[1,5-a]pyrimidin-2-amine

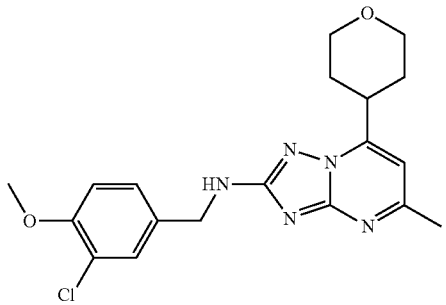

[M+H]=388.38.

Example 22. 7-(4,4-Difluorocyclohexyl)-N-[(4-methoxyphenyl)methyl]-5-methyl-[1,2,4]triazolo[1,5-a]pyrimidin-2-amine

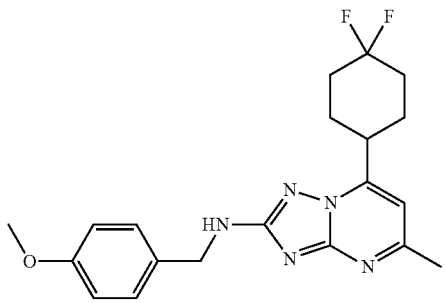

[M+H]=388.46.

Example 23. N-{[3-(Difluoromethyl)phenyl]methyl}-5-methyl-7-(oxan-4-yl)-[1,2,4]triazolo[1,5-a]pyrimidin-2-amine

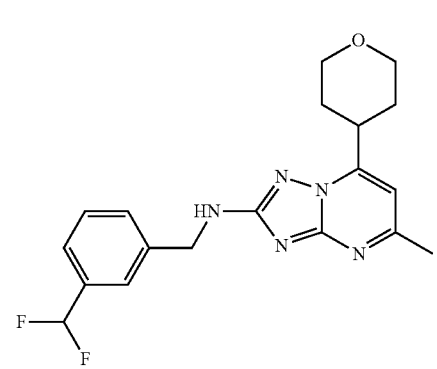 [SMILES: Cc1cc(C2CCOCC2)n2nc(NCc3cccc(C(F)F)c3)nc2n1]

¹H NMR (400 MHz, CDCl₃) δ=7.60-7.47 (m, 2H), 7.44-7.36 (m, 2H), 6.90-6.41 (m, 2H), 5.14 (t, J=6.3 Hz, 1H), 4.67 (d, J=6.3 Hz, 2H), 4.18-4.02 (m, 2H), 3.61 (dt, J=2.0, 11.9 Hz, 2H), 3.54-3.42 (m, 1H), 2.58 (s, 3H), 2.08-1.96 (m, 2H), 1.87-1.74 (m, 2H); [M+H]=374.45.

Example 24. N-[(3-Methoxyphenyl)methyl]-5-methyl-7-(oxan-4-yl)-[1,2,4]triazolo[1,5-a]pyrimidin-2-amine

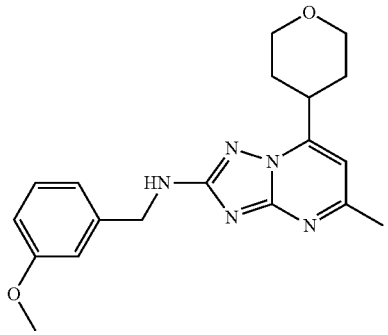 [SMILES: COc1cccc(CNc2nc3nc(C)cc(C4CCOCC4)n3n2)c1]

¹H NMR (400 MHz, CDCl₃) δ=7.24 (d, J=7.8 Hz, 1H), 7.03-6.93 (m, 2H), 6.81 (dd, J=2.5, 8.4 Hz, 1H), 6.54 (s, 1H), 4.97 (t, J=6.1 Hz, 1H), 4.62 (d, J=5.9 Hz, 2H), 4.12 (dd, J=3.9, 11.3 Hz, 2H), 3.80 (s, 3H), 3.63 (dt, J=2.0, 11.9 Hz, 2H), 3.54 (tt, J=3.5, 11.9 Hz, 1H), 2.59 (s, 3H), 2.11-2.00 (m, 2H), 1.90-1.74 (m, 2H); [M+H]=354.48.

Example 25. N-{[3-(Difluoromethyl)-4-methoxyphenyl]methyl}-5-methyl-7-(oxan-4-yl)-[1,2,4]triazolo[1,5-a]pyrimidin-2-amine

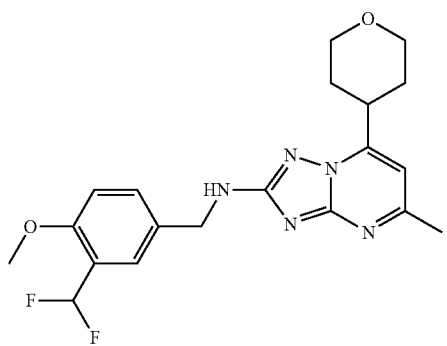

¹H NMR (400 MHz, CDCl₃) δ=7.62 (s, 1H), 7.47 (dd, J=1.0, 8.4 Hz, 1H), 7.07-6.76 (m, 2H), 6.53 (s, 1H), 5.08 (br s, 1H), 4.58 (d, J=6.3 Hz, 2H), 4.11 (dd, J=3.9, 11.3 Hz, 2H), 3.84 (s, 3H), 3.63 (dt, J=1.8, 11.8 Hz, 2H), 3.53 (tt, J=3.5, 11.9 Hz, 1H), 2.57 (s, 3H), 2.04 (dd, J=1.6, 12.9 Hz, 2H), 1.80 (dq, J=4.3, 12.4 Hz, 2H); [M+H]=404.41.

Example 26. N-[(2-Fluorophenyl)methyl]-5-methyl-7-(oxan-4-yl)-[1,2,4]triazolo[1,5-a]pyrimidin-2-amine

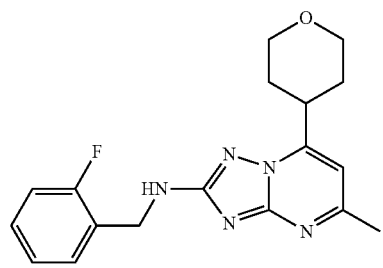

¹H NMR (400 MHz, CDCl₃) δ=7.47 (t, J=7.2 Hz, 1H), 7.31-6.95 (m, 3H), 6.52 (s, 1H), 5.09 (br s, 1H), 4.68 (d, J=6.3 Hz, 2H), 4.11 (d, J=8.6 Hz, 2H), 3.77-3.42 (m, 3H), 2.57 (s, 3H), 2.03 (d, J=12.1 Hz, 2H), 1.85-1.72 (m, 2H); [M+H]=341.98.

Example 27. N-[(2-Fluoro-5-methylphenyl)methyl]-5-methyl-7-(oxan-4-yl)-[1,2,4]triazolo[1,5-a]pyrimidin-2-amine

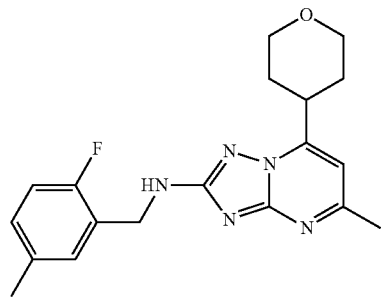 [SMILES: Cc1ccc(F)c(CNc2nc3nc(C)cc(C4CCOCC4)n3n2)c1]

¹H NMR (400 MHz, CDCl₃) δ=7.27-7.24 (m, 1H), 7.04-6.98 (m, 1H), 6.95-6.88 (m, 1H), 6.52 (s, 1H), 5.01 (t, J=6.3 Hz, 1H), 4.64 (d, J=6.3 Hz, 2H), 4.12 (dd, J=3.9, 11.3 Hz, 2H), 3.71-3.45 (m, 3H), 2.63-2.54 (m, 3H), 2.34-2.20 (m, 3H), 2.11-1.96 (m, 2H), 1.80 (dq, J=4.5, 12.5 Hz, 2H); [M+H]=356.48.

Example 28. 5-Methyl-N-[(3-methylphenyl)methyl]-7-(oxan-4-yl)-[1,2,4]triazolo[1,5-a]pyrimidin-2-amine

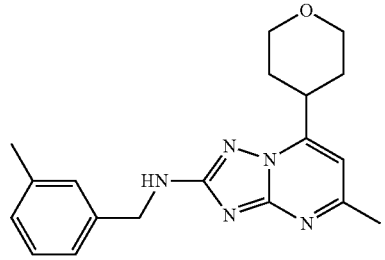 [SMILES: Cc1cccc(CNc2nc3nc(C)cc(C4CCOCC4)n3n2)c1]

¹H NMR (400 MHz, CDCl₃) δ=7.24-7.23 (m, 1H), 7.24-7.15 (m, 3H), 7.07 (d, J=6.3 Hz, 1H), 6.53 (s, 1H), 4.97 (t, J=5.9 Hz, 1H), 4.59 (d, J=6.3 Hz, 2H), 4.11 (dd, J=3.9, 11.3 Hz, 2H), 3.62 (dt, J=2.0, 11.9 Hz, 2H), 3.53 (tt, J=3.6, 12.1 Hz, 1H), 2.58 (s, 3H), 2.33 (s, 3H), 2.08-2.01 (m, 2H), 1.86-1.73 (m, 2H); [M+H]=354.14.

Example 29. 5-(Difluoromethyl)-N-[(4-methoxyphenyl)methyl]-7-(oxan-4-yl)-[1,2,4]triazolo[1,5-a]pyrimidin-2-amine

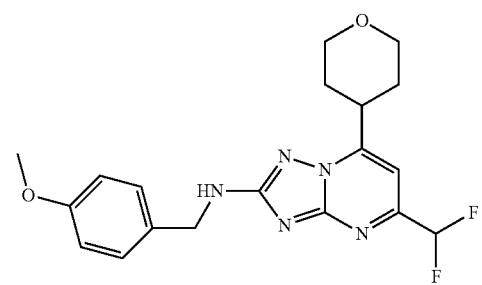 [SMILES: COc1ccc(CNc2nc3nc(C(F)F)cc(C4CCOCC4)n3n2)cc1]

¹H NMR (400 MHz, CDCl₃) δ=7.33 (d, J=8.6 Hz, 2H), 7.01 (s, 1H), 6.87 (d, J=8.6 Hz, 2H), 6.58 (t, J=54.0 Hz, 1H), 5.18 (t, J=5.9 Hz, 1H), 4.60 (d, J=5.9 Hz, 2H), 4.15 (dd, J=3.5, 11.0 Hz, 2H), 3.80 (s, 3H), 3.71-3.60 (m, 3H), 2.16-2.04 (m, 2H), 1.97-1.80 (m, 2H); [M+H]=390.47.

Example 30. 5-(Fluoromethyl)-N-[(4-methoxyphenyl)methyl]-7-(oxan-4-yl)-[1,2,4]triazolo[1,5-a]pyrimidin-2-amine

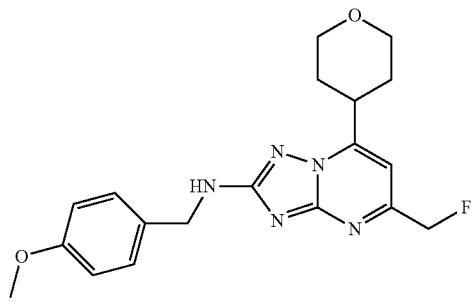 [SMILES: COc1ccc(CNc2nc3nc(CF)cc(C4CCOCC4)n3n2)cc1]

¹H NMR (400 MHz, CDCl₃) δ=7.32 (d, J=8.6 Hz, 2H), 6.89 (d, J=1.2 Hz, 1H), 6.86 (d, J=8.6 Hz, 2H), 5.47 (d, J=44.0 Hz, 2H), 4.97 (t, J=5.9 Hz, 1H), 4.58 (d, J=5.9 Hz, 2H), 4.20-4.07 (m, 2H), 3.79 (s, 3H), 3.70-3.55 (m, 3H), 2.14-2.03 (m, 2H), 1.93-1.78 (m, 2H); [M+H]=372.5.

Example 31-Example 77 were prepared in a manner analogous to Example 1, Method B, with the appropriate starting material substitutions.

Example 31. N-{[1-(3-Methoxyphenyl)-1H-pyrazol-4-yl]methyl}-5-methyl-7-(oxan-4-yl)-[1,2,4]triazolo[1,5-a]pyrimidin-2-amine

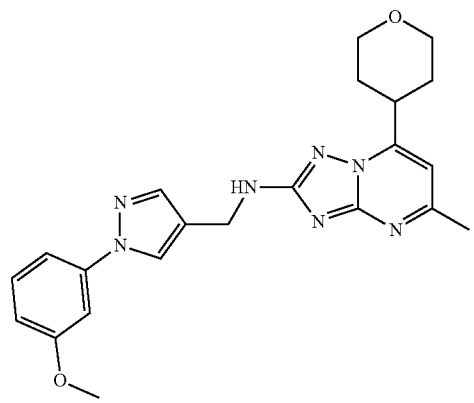 [SMILES: COc1cccc(-n2cc(CNc3nc4nc(C)cc(C5CCOCC5)n4n3)cn2)c1]

¹H NMR (400 MHz, DMSO-d₆) δ=8.42 (s, 1H), 7.71 (s, 1H), 7.45-7.30 (m, 3H), 7.23 (t, J=5.9 Hz, 1H), 6.96-6.77 (m, 2H), 4.37 (d, J=5.9 Hz, 2H), 3.97 (dd, J=3.3, 11.2 Hz, 2H), 3.81 (s, 2H), 3.57-3.41 (m, 3H), 2.49 (s, 3H), 2.00-1.92 (m, 2H), 1.76 (dq, J=4.3, 12.4 Hz, 2H); [M+H]=420.49.

Example 32. N-[(2-Fluoro-5-methoxyphenyl)methyl]-5-methyl-7-(oxan-4-yl)-[1,2,4]triazolo[1,5-a]pyrimidin-2-amine

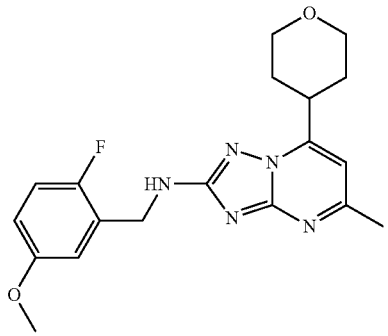 [SMILES: COc1ccc(F)c(CNc2nc3nc(C)cc(C4CCOCC4)n3n2)c1]

¹H NMR (400 MHz, CDCl₃) δ=7.01 (dd, J=3.1, 5.9 Hz, 1H), 6.96 (t, J=9.2 Hz, 1H), 6.73 (td, J=3.6, 8.8 Hz, 1H), 6.53 (s, 1H), 5.09 (t, J=6.5 Hz, 1H), 4.65 (d, J=6.3 Hz, 2H), 4.16-4.08 (m, 2H), 3.74 (s, 3H), 3.63 (dt, J=2.0, 11.9 Hz, 2H), 3.53 (tt, J=3.5, 11.9 Hz, 1H), 2.58 (s, 3H), 2.08-2.01 (m, 2H), 1.87-1.74 (m, 2H); [M+H]=372.46.

Example 33. N-Benzyl-5-methyl-7-(oxan-4-yl)-[1,2,4]triazolo[1,5-a]pyrimidin-2-amine

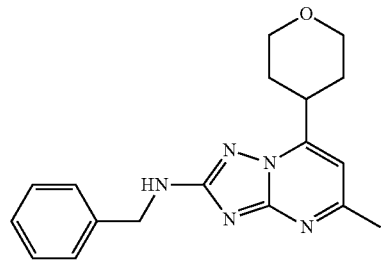 [SMILES: Cc1cc(C2CCOCC2)n2nc(NCc3ccccc3)nc2n1]

¹H NMR (400 MHz, CDCl₃) δ=7.44-7.37 (m, 2H), 7.32 (t, J=7.4 Hz, 2H), 7.28-7.21 (m, 1H), 6.53 (s, 1H), 5.06 (br s, 1H), 4.64 (d, J=6.3 Hz, 2H), 4.11 (dd, J=4.5, 11.5 Hz, 2H), 3.61 (dt, J=1.8, 11.8 Hz, 2H), 3.52 (tt, J=3.4, 12.1 Hz, 1H), 2.58 (s, 3H), 2.04 (dd, J=1.8, 12.7 Hz, 2H), 1.87-1.72 (m, 2H); [M+H]=324.42.

Example 34. N-[(4-Methoxyphenyl)methyl]-5-methyl-7-(4-methyloxan-4-yl)-[1,2,4]triazolo[1,5-a]pyrimidin-2-amine

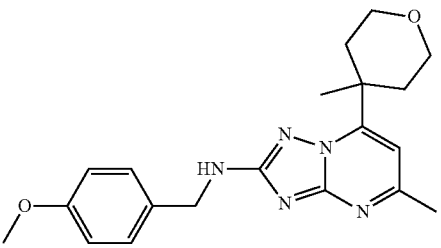

¹H NMR (400 MHz, CDCl₃) δ=7.33 (d, J=8.2 Hz, 2H), 6.86 (d, J=8.6 Hz, 2H), 6.55 (s, 1H), 4.93 (t, J=5.9 Hz, 1H), 4.54 (d, J=5.9 Hz, 2H), 3.87-3.68 (m, 6H), 2.59 (s, 3H), 2.37 (ddd, J=4.3, 8.9, 13.4 Hz, 2H), 2.15-2.02 (m, 2H), 1.60 (s, 3H); [M+H]=368.47.

Example 35. 5-Methyl-N-[(2-methylpyridin-4-yl)methyl]-7-(oxan-4-yl)-[1,2,4]triazolo[1,5-a]pyrimidin-2-amine

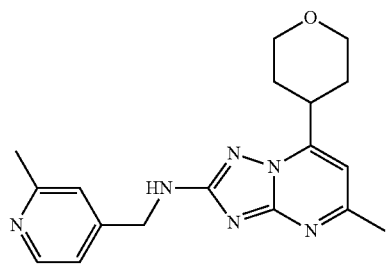 [SMILES: Cc1cc(CNc2nc3nc(C)cc(C4CCOCC4)n3n2)ccn1]

¹H NMR (400 MHz, DMSO-d₆) δ=11.92 (s, 1H), 8.31 (d, J=5.1 Hz, 1H), 7.51 (t, J=6.5 Hz, 1H), 7.18 (s, 1H), 7.14-7.08 (m, 1H), 6.85 (s, 1H), 4.41 (d, J=6.3 Hz, 2H), 3.95 (dd, J=3.1, 11.3 Hz, 2H), 3.51-3.34 (m, 3H), 2.46 (s, 3H), 2.40 (s, 3H), 1.90 (br s, 1H), 1.89 (s, 3H), 1.87 (d, J=1.6 Hz, 1H), 1.71 (dq, J=4.3, 12.4 Hz, 2H); [M+H]=338.76.

Example 36. 5-Methyl-N-{[1-(2-methylphenyl)-1H-pyrazol-4-yl]methyl}-7-(oxan-4-yl)-[1,2,4]triazolo[1,5-a]pyrimidin-2-amine

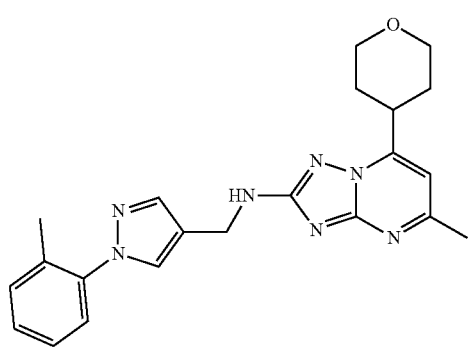 [SMILES: Cc1cc(C2CCOCC2)n2nc(NCc3cnn(-c4ccccc4C)c3)nc2n1]

¹H NMR (400 MHz, CDCl₃) δ=7.72 (s, 1H), 7.63 (s, 1H), 7.31-7.21 (m, 4H), 6.54 (s, 1H), 5.02 (t, J=5.9 Hz, 1H), 4.58 (d, J=6.3 Hz, 2H), 4.14-4.07 (m, 2H), 3.62 (dt, J=2.0, 11.9 Hz, 2H), 3.58-3.49 (m, 1H), 2.58 (s, 3H), 2.23 (s, 3H), 2.10-2.07 (m, 1H), 2.05 (dd, J=2.3, 4.3 Hz, 1H), 1.90-1.76 (m, 2H); [M+H]=404.20.

Example 37. 5-Methyl-7-(oxan-4-yl)-N-[(3-phenyl-1,2-oxazol-5-yl)methyl]-[1,2,4]triazolo[1,5-a]pyrimidin-2-amine

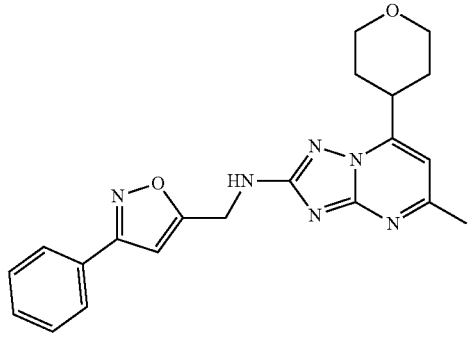 [SMILES: Cc1cc(C2CCOCC2)n2nc(NCc3cc(-c4ccccc4)no3)nc2n1]

¹H NMR (400 MHz, DMSO-d₆) δ=7.85-7.77 (m, 2H), 7.60 (t, J=6.1 Hz, 1H), 7.50-7.42 (m, 3H), 6.86 (d, J=5.9 Hz, 2H), 4.62 (d, J=5.9 Hz, 2H), 3.92 (dd, J=3.1, 11.3 Hz, 2H), 3.52-3.36 (m, 3H), 1.91 (d, J=12.1 Hz, 2H), 1.71 (dq, J=4.1, 12.3 Hz, 2H); [M+H]=391.17.

Example 38. N-[(4-Methoxyphenyl)methyl]-5-methyl-7-(oxan-3-yl)-[1,2,4]triazolo[1,5-a]pyrimidin-2-amine

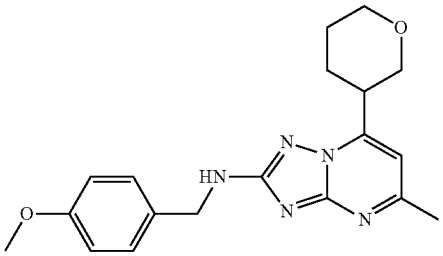

¹H NMR (400 MHz, CDCl₃) δ=7.32 (d, J=8.6 Hz, 2H), 6.85 (d, J=8.6 Hz, 2H), 6.66 (s, 1H), 4.93 (t, J=5.9 Hz, 1H), 4.55 (d, J=6.3 Hz, 2H), 4.24-4.15 (m, 1H), 3.92 (td, J=4.2, 11.2 Hz, 1H), 3.79 (s, 3H), 3.71-3.56 (m, 3H), 2.57 (s, 3H), 2.22-2.11 (m, 1H), 1.95 (dtd, J=4.9, 8.9, 13.4 Hz, 1H), 1.84-1.67 (m, 2H); [M+H]=354.46.

Example 39. N-[(3-Bromophenyl)methyl]-5-methyl-7-(oxan-4-yl)-[1,2,4]triazolo[1,5-a]pyrimidin-2-amine

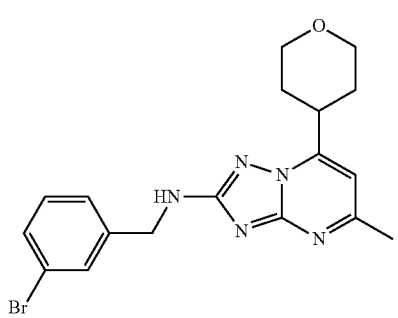 [SMILES: Cc1cc(C2CCOCC2)n2nc(NCc3cccc(Br)c3)nc2n1]

¹H NMR (400 MHz, CDCl₃) δ=7.57 (t, J=1.6 Hz, 1H), 7.37 (qd, J=1.0, 7.8 Hz, 1H), 7.34-7.30 (m, 1H), 7.20-7.14 (m, 1H), 6.53 (s, 1H), 5.15 (t, J=6.5 Hz, 1H), 4.60 (d, J=6.3 Hz, 2H), 4.15-4.07 (m, 2H), 3.62 (dt, J=2.0, 11.9 Hz, 2H), 3.51 (tt, J=3.5, 11.9 Hz, 1H), 2.60-2.56 (m, 3H), 2.07-1.99 (m, 2H), 1.86-1.77 (m, 2H); [M+H]=404.02.

Example 40. N-[(3-Chlorophenyl)methyl]-5-methyl-7-(oxan-4-yl)-[1,2,4]triazolo[1,5-a]pyrimidin-2-amine

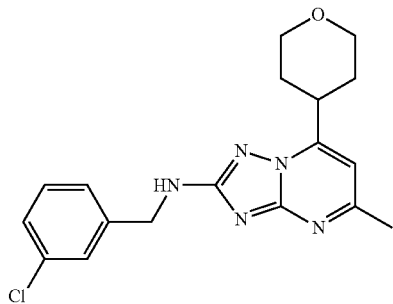 [SMILES: Cc1cc(C2CCOCC2)n2nc(NCc3cccc(Cl)c3)nc2n1]

¹H NMR (400 MHz, CDCl₃) δ=7.42-7.39 (m, 1H), 7.30-7.25 (m, 2H), 7.24-7.20 (m, 2H), 6.53 (s, 1H), 5.13 (t, J=6.3 Hz, 1H), 4.60 (d, J=6.3 Hz, 2H), 4.11 (dd, J=3.5, 11.0 Hz, 2H), 3.62 (dt, J=2.0, 11.9 Hz, 2H), 3.51 (tt, J=3.5, 12.1 Hz, 1H), 2.58 (s, 3H), 2.08-1.98 (m, 2H), 1.87-1.74 (m, 2H); [M+H]=358.13.

Example 41. 5-Methyl-7-(oxan-4-yl)-N-{[3-(trifluoromethyl)phenyl]methyl}-[1,2,4]triazolo[1,5-a]pyrimidine-2-amine

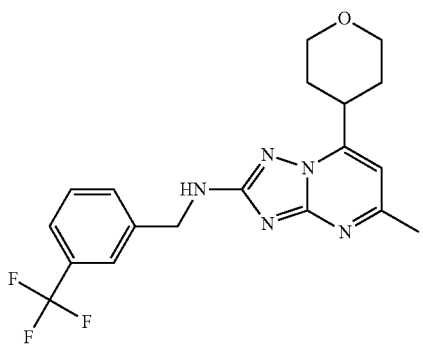 [SMILES: Cc1cc(C2CCOCC2)n2nc(NCc3cccc(C(F)(F)F)c3)nc2n1]

¹H NMR (400 MHz, CDCl₃) δ=7.68 (s, 1H), 7.60 (d, J=7.8 Hz, 1H), 7.53-7.48 (m, 1H), 7.45-7.40 (m, 1H), 6.54 (s, 1H), 5.21 (t, J=6.3 Hz, 1H), 4.68 (d, J=6.3 Hz, 2H), 4.15-4.06 (m, 2H), 3.66-3.56 (m, 2H), 3.50 (tt, J=3.7, 12.0 Hz, 1H), 2.60-2.56 (m, 3H), 2.06-1.97 (m, 2H), 1.87-1.73 (m, 2H); [M+H]=392.61.

Example 42. N-(2,3-Dihydro-1-benzofuran-5-ylmethyl)-5-methyl-7-(oxan-4-yl)-[1,2,4]triazolo[1,5-a]pyrimidin-2-amine

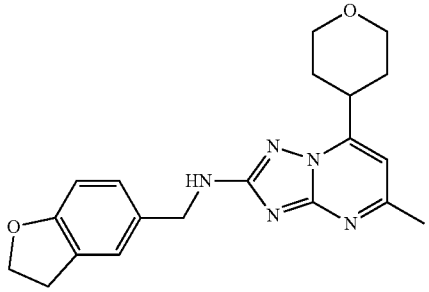 [SMILES: Cc1cc(C2CCOCC2)n2nc(NCc3ccc4c(c3)CCO4)nc2n1]

¹H NMR (400 MHz, CDCl₃) δ=7.24 (s, 1H), 7.12 (dd, J=1.8, 8.0 Hz, 1H), 6.71 (d, J=8.2 Hz, 1H), 6.52 (s, 1H), 4.97 (t, J=5.9 Hz, 1H), 4.58-4.50 (m, 4H), 4.16-4.06 (m, 2H), 3.61 (dt, J=2.0, 11.7 Hz, 2H), 3.52 (tt, J=3.5, 12.1 Hz, 1H), 3.16 (t, J=8.6 Hz, 2H), 2.60-2.54 (m, 3H), 2.09-1.99 (m, 2H), 1.87-1.73 (m, 2H); [M+H]=366.12.

Example 43. 5-Methyl-7-(4-methyloxan-4-yl)-N-[(2-methylpyridin-4-yl)methyl]-[1,2,4]triazolo[1,5-a]pyrimidin-2-amine

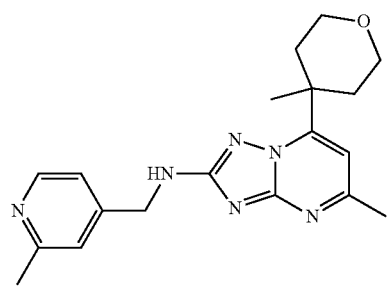 [SMILES: Cc1cc(CNc2nc3nc(C)cc(C4(C)CCOCC4)n3n2)ccn1]

¹H NMR (400 MHz, CDCl₃) δ=8.37 (d, J=5.1 Hz, 1H), 7.17 (s, 1H), 7.10 (d, J=5.1 Hz, 1H), 6.53 (s, 1H), 5.89 (t, J=6.1 Hz, 1H), 4.55 (d, J=5.9 Hz, 2H), 3.84-3.59 (m, 4H), 2.55 (s, 3H), 2.48 (s, 3H), 2.28 (ddd, J=4.1, 9.0, 13.5 Hz, 2H), 2.04-1.93 (m, 2H), 1.49 (s, 3H); [M+H]=353.49.

Example 44. N-[(4-Methoxyphenyl)methyl]-5-methyl-7-(oxolan-3-yl)-[1,2,4]triazolo[1,5-a]pyrimidin-2-amine

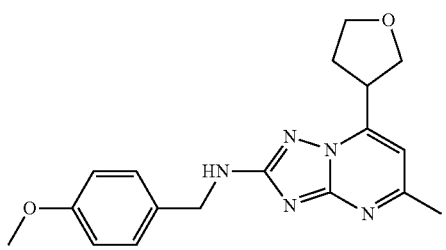

¹H NMR (400 MHz, CDCl₃) δ=7.31 (d, J=8.6 Hz, 2H), 6.84 (d, J=8.6 Hz, 2H), 6.61 (s, 1H), 5.09 (t, J=5.9 Hz, 1H), 4.54 (d, J=5.9 Hz, 2H), 4.18 (dd, J=7.0, 8.6 Hz, 1H), 4.10-4.00 (m, 2H), 3.99-3.89 (m, 2H), 3.77 (s, 3H), 2.56 (s, 3H), 2.51-2.40 (m, 1H), 2.21-2.08 (m, 1H); [M+H]=340.46.

Example 45. N-[(2,2-Difluoro-2H-1,3-benzodioxol-5-yl)methyl]-5-methyl-7-(oxan-4-yl)-[1,2,4]triazolo[1,5-a]pyrimidin-2-amine

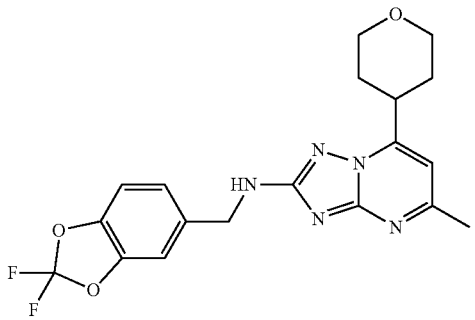 [SMILES: Cc1cc(C2CCOCC2)n2nc(NCc3ccc4c(c3)OC(F)(F)O4)nc2n1]

$^1$H NMR (400 MHz, CDCl$_3$) δ=7.26 (s, 1H), 7.17 (d, J=1.6 Hz, 1H), 7.14-7.07 (m, 1H), 6.97 (d, J=8.2 Hz, 1H), 6.54 (s, 1H), 5.26 (t, J=6.5 Hz, 1H), 4.60 (d, J=6.3 Hz, 2H), 4.16-4.06 (m, 2H), 3.61 (dt, J=2.2, 11.8 Hz, 2H), 3.49 (tt, J=3.6, 12.1 Hz, 1H), 2.58 (s, 3H), 2.08-1.97 (m, 2H), 1.89-1.74 (m, 2H); [M+H]=404.5.

Example 46. 5-Methyl-N-[(3-methyl-1-phenyl-1H-pyrazol-4-yl)methyl]-7-(oxan-4-yl)-[1,2,4]triazolo[1,5-a]pyrimidin-2-amine

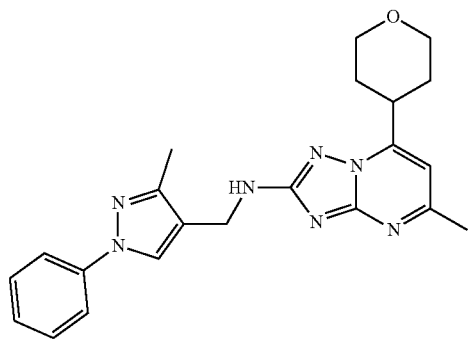 [SMILES: Cc1cc(C2CCOCC2)n2nc(NCc3cn(-c4ccccc4)nc3C)nc2n1]

$^1$H NMR (400 MHz, CDCl$_3$) δ=7.89 (s, 1H), 7.63-7.57 (m, 2H), 7.45-7.36 (m, 2H), 7.25-7.17 (m, 1H), 6.54 (s, 1H), 4.91 (t, J=5.9 Hz, 1H), 4.51 (d, J=5.9 Hz, 2H), 4.16-4.04 (m, 2H), 3.62 (dt, J=2.0, 11.7 Hz, 2H), 3.54 (tt, J=3.5, 12.1 Hz, 1H), 2.58 (s, 3H), 2.38 (s, 3H), 2.11-2.00 (m, 3H), 1.89-1.75 (m, 2H); [M+H]=404.49.

Example 47. 5-Methyl-N-[(2-methylphenyl)methyl]-7-(oxan-4-yl)-[1,2,4]triazolo[1,5-a]pyrimidin-2-amine

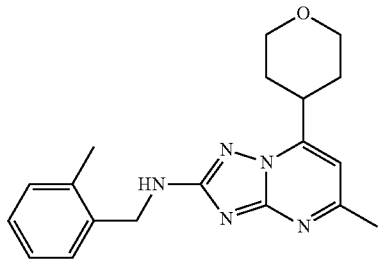

$^1$H NMR (400 MHz, CDCl$_3$) δ=7.39-7.35 (m, 1H), 7.20-7.13 (m, 3H), 6.53 (s, 1H), 4.83 (t, J=5.9 Hz, 1H), 4.61 (d, J=5.9 Hz, 2H), 4.12 (dd, J=3.5, 11.0 Hz, 2H), 3.63 (dt, J=2.0, 11.9 Hz, 2H), 3.54 (tt, J=3.5, 11.9 Hz, 1H), 2.60-2.55 (m, 3H), 2.40 (s, 3H), 2.09-2.01 (m, 2H), 1.87-1.74 (m, 2H); [M+H]=337.87.

Example 48. N-[(2-Chlorophenyl)methyl]-5-methyl-7-(oxan-4-yl)-[1,2,4]triazolo[1,5-a]pyrimidin-2-amine

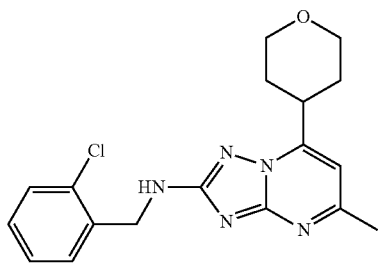 [SMILES: Cc1cc(C2CCOCC2)n2nc(NCc3ccccc3C)nc2n1]

$^1$H NMR (400 MHz, CDCl$_3$) δ=7.57-7.51 (m, 1H), 7.39-7.33 (m, 1H), 7.22-7.16 (m, 2H), 6.52 (s, 1H), 5.18 (t, J=6.5 Hz, 1H), 4.72 (d, J=6.7 Hz, 2H), 4.16-4.07 (m, 2H), 3.62 (dt, J=2.0, 11.9 Hz, 2H), 3.51 (tt, J=3.5, 12.1 Hz, 1H), 2.57 (s, 3H), 2.07-1.98 (m, 2H), 1.86-1.73 (m, 2H); [M+H]=357.2.

Example 49. N-[(2,5-Difluorophenyl)methyl]-5-methyl-7-(oxan-4-yl)-[1,2,4]triazolo[1,5-a]pyrimidin-2-amine

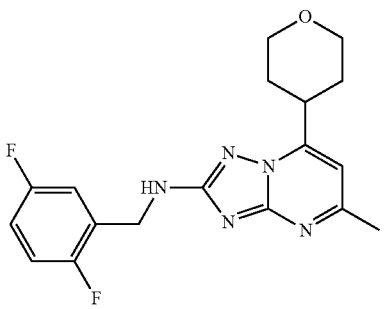 [SMILES: Cc1cc(C2CCOCC2)n2nc(NCc3cc(F)ccc3F)nc2n1]

¹H NMR (400 MHz, CDCl₃) δ=7.20 (ddd, J=3.3, 5.6, 8.7 Hz, 1H), 7.03-6.95 (m, 1H), 6.93-6.85 (m, 1H), 6.54 (s, 1H), 5.08 (t, J=6.5 Hz, 1H), 4.65 (d, J=6.3 Hz, 2H), 4.12 (dd, J=3.7, 10.8 Hz, 2H), 3.63 (dt, J=2.0, 11.9 Hz, 2H), 3.51 (tt, J=3.7, 12.0 Hz, 1H), 2.58 (s, 3H), 2.07-1.99 (m, 2H), 1.86-1.73 (m, 2H); [M+H]=360.58.

Example 50. N-[(2,6-Difluoro-4-methoxyphenyl)methyl]-5-methyl-7-(oxan-4-yl)-[1,2,4]triazolo[1,5-a]pyrimidin-2-amine

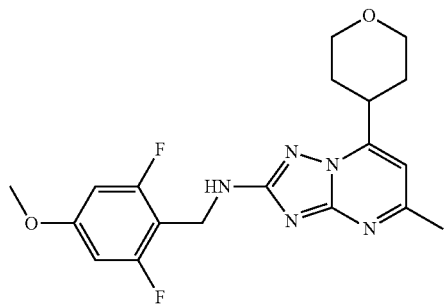

¹H NMR (400 MHz, CDCl₃) δ=6.60 (s, 1H), 6.53 (s, 1H), 6.46-6.39 (m, 2H), 5.88-5.71 (m, 1H), 4.59 (d, J=6.1 Hz, 2H), 4.15 (dd, J=4.2, 11.3 Hz, 2H), 3.76 (s, 3H), 3.67 (dt, J=1.8, 11.8 Hz, 2H), 3.55 (tt, J=3.5, 12.0 Hz, 1H), 2.57 (s, 3H), 2.09-2.03 (m, 2H), 1.79 (dq, J=4.3, 12.4 Hz, 2H); [M+H]=390.3.

Example 51. N-[(2,6-Difluorophenyl)methyl]-5-methyl-7-(oxan-4-yl)-[1,2,4]triazolo[1,5-a]pyrimidin-2-amine

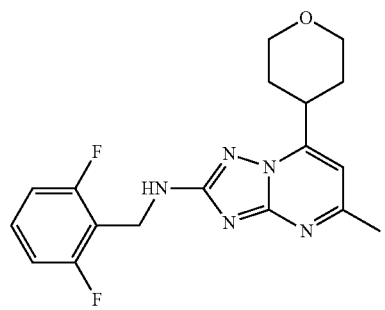 [SMILES: Cc1cc(C2CCOCC2)n2nc(NCc3c(F)cccc3F)nc2n1]

¹H NMR (400 MHz, CDCl₃) δ=7.21 (tt, J=6.5, 8.4 Hz, 1H), 6.90-6.81 (m, 2H), 6.51 (s, 1H), 5.05 (t, J=6.5 Hz, 1H), 4.70 (d, J=6.3 Hz, 2H), 4.17-4.10 (m, 2H), 3.65 (dt, J=2.0, 11.7 Hz, 2H), 3.54 (tt, J=3.5, 11.9 Hz, 1H), 2.56 (s, 3H), 2.09-2.00 (m, 2H), 1.84-1.72 (m, 2H); [M+H]=360.59.

Example 52. N-{[2-(Difluoromethyl)pyridin-4-yl]methyl}-5-methyl-7-(oxan-4-yl)-[1,2,4]triazolo[1,5-a]pyrimidin-2-amine

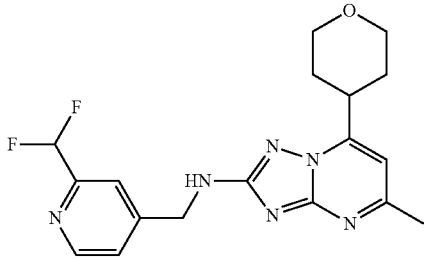 [SMILES: Cc1cc(C2CCOCC2)n2nc(NCc3ccnc(C(F)F)c3)nc2n1]

¹H NMR (400 MHz, CDCl₃) δ=8.55 (d, J=5.1 Hz, 1H), 7.68 (s, 1H), 7.51-7.41 (m, 1H), 6.54 (s, 1H), 6.60 (t, J=56.0 Hz, 1H), 5.82 (t, J=6.5 Hz, 1H), 4.71 (d, J=6.7 Hz, 2H), 4.15-4.03 (m, 2H), 3.58 (dt, J=2.2, 11.8 Hz, 2H), 3.46 (tt, J=3.5, 11.9 Hz, 1H), 2.57 (s, 3H), 1.86-1.71 (m, 2H); [M+H]=375.5.

Example 53. N-[(2,6-Dimethylpyridin-4-yl)methyl]-5-methyl-7-(oxan-4-yl)-[1,2,4]triazolo[1,5-a]pyrimidin-2-amine

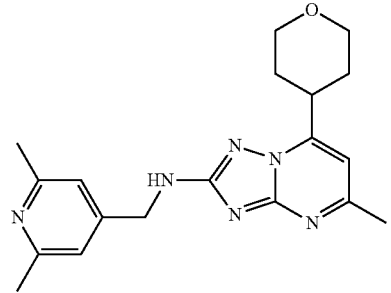 [SMILES: Cc1cc(CNc2nc3nc(C)cc(C4CCOCC4)n3n2)cc(C)n1]

¹H NMR (400 MHz, CDCl₃) δ=6.99 (s, 2H), 6.56 (s, 1H), 5.82 (t, J=6.1 Hz, 1H), 4.56 (d, J=6.3 Hz, 2H), 4.18-4.06 (m, 2H), 3.60 (dt, J=2.0, 11.9 Hz, 2H), 3.54-3.42 (m, 1H), 2.52-2.47 (m, 6H), 2.08 (s, 3H), 2.05-1.96 (m, 2H), 1.87-1.72 (m, 2H); [M+H]=353.5.

Example 54. 5-Methyl-N-[(5-methylpyridin-3-yl)methyl]-7-(oxan-4-yl)-[1,2,4]triazolo[1,5-a]pyrimidin-2-amine

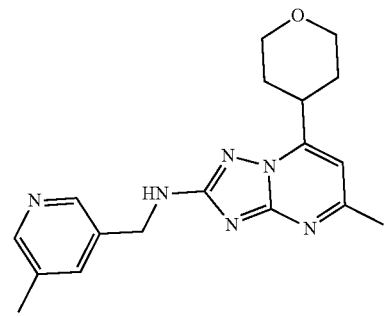 [SMILES: Cc1cncc(CNc2nc3nc(C)cc(C4CCOCC4)n3n2)c1]

¹H NMR (400 MHz, CDCl₃) δ=8.45 (d, J=1.6 Hz, 1H), 8.33 (d, J=1.6 Hz, 1H), 7.55 (d, J=0.8 Hz, 1H), 6.54 (s, 1H), 5.08 (t, J=6.3 Hz, 1H), 4.61 (d, J=6.3 Hz, 2H), 4.11 (dd, J=3.5, 10.6 Hz, 2H), 3.62 (dt, J=2.0, 11.9 Hz, 2H), 3.51 (tt, J=3.5, 11.9 Hz, 1H), 2.58 (s, 3H), 2.30 (d, J=0.8 Hz, 3H), 2.07-2.00 (m, 2H), 1.87-1.74 (m, 2H); [M+H]=339.20.

Example 55. 7-(4-Fluorooxan-4-yl)-N-[(4-methoxyphenyl)methyl]-5-methyl-[1,2,4]triazolo[1,5-a]pyrimidin-2-amine

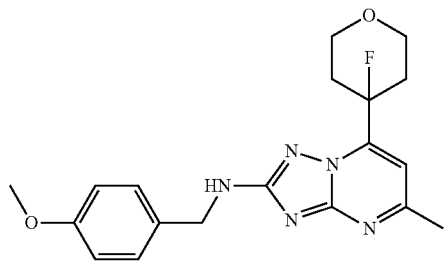

¹H NMR (400 MHz, CDCl₃) δ=7.34 (d, J=8.6 Hz, 2H), 6.91-6.79 (m, 3H), 5.02 (t, J=5.9 Hz, 1H), 4.53 (d, J=6.3 Hz, 2H), 4.04-3.95 (m, 2H), 3.93-3.82 (m, 2H), 3.79 (s, 3H), 3.38-3.09 (m, 2H), 2.61 (s, 3H), 1.64 (d, J=6.7 Hz, 2H); [M+H]=372.5.

Example 56. N-[(3,4-Difluorophenyl)methyl]-5-methyl-7-(oxan-4-yl)-[1,2,4]triazolo[1,5-a]pyrimidin-2-amine

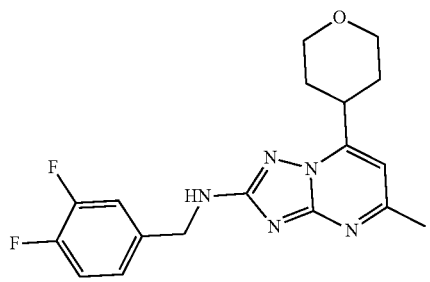 [SMILES: Cc1cc(C2CCOCC2)n2nc(NCc3ccc(F)c(F)c3)nc2n1]

¹H NMR (400 MHz, CDCl₃) δ=7.26-7.21 (m, 1H), 7.14-7.05 (m, 2H), 6.55 (s, 1H), 5.05 (t, J=6.3 Hz, 1H), 4.58 (d, J=6.7 Hz, 2H), 4.12 (dd, J=4.3, 11.3 Hz, 2H), 3.61 (dt, J=1.8, 11.8 Hz, 2H), 3.50 (tt, J=3.7, 12.0 Hz, 1H), 2.58 (s, 3H), 2.06-1.99 (m, 2H), 1.88-1.75 (m, 2H); [M+H]=360.54.

Example 57. N-[(4-Fluorophenyl)methyl]-5-methyl-7-(oxan-4-yl)-[1,2,4]triazolo[1,5-a]pyrimidin-2-amine

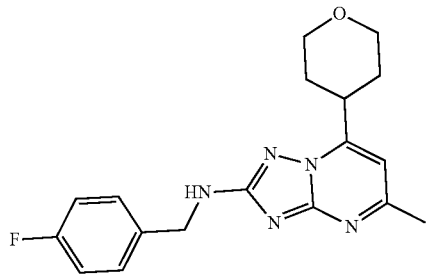 [SMILES: Cc1cc(C2CCOCC2)n2nc(NCc3ccc(F)cc3)nc2n1]

¹H NMR (400 MHz, CDCl₃) δ=7.41-7.33 (m, 2H), 6.99 (t, J=8.6 Hz, 2H), 6.53 (s, 1H), 5.00 (d, J=6.3 Hz, 1H), 4.59 (d, J=5.9 Hz, 2H), 4.11 (dd, J=3.9, 11.3 Hz, 2H), 3.61 (dt, J=1.8, 11.8 Hz, 2H), 3.50 (tt, J=3.6, 12.1 Hz, 1H), 2.58 (s, 3H), 2.03 (dd, J=1.8, 12.7 Hz, 2H), 1.80 (dq, J=4.5, 12.5 Hz, 2H); [M+H]=342.55.

Example 58. N-[(3-Fluorophenyl)methyl]-5-methyl-7-(oxan-4-yl)-[1,2,4]triazolo[1,5-a]pyrimidin-2-amine

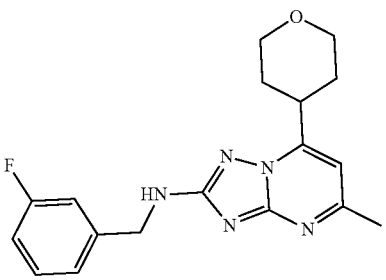 [SMILES: Cc1cc(C2CCOCC2)n2nc(NCc3cccc(F)c3)nc2n1]

¹H NMR (400 MHz, CDCl₃) δ=7.31-7.24 (m, 1H), 7.18-7.15 (m, 1H), 7.14-7.09 (m, 1H), 6.94 (dt, J=2.2, 8.3 Hz, 1H), 6.54 (s, 1H), 5.04 (br s, 1H), 4.63 (d, J=6.3 Hz, 2H), 4.11 (dd, J=3.5, 11.0 Hz, 2H), 3.61 (dt, J=2.0, 11.9 Hz, 2H), 3.51 (tt, J=3.5, 11.9 Hz, 1H), 2.58 (s, 3H), 2.07-1.99 (m, 2H), 1.87-1.74 (m, 2H); [M+H]=342.54.

Example 59. 5-Methyl-7-(oxan-4-yl)-N-{[2-(trifluoromethyl)pyridin-4-yl]methyl}-[1,2,4]triazolo[1,5-a]pyrimidin-2-amine

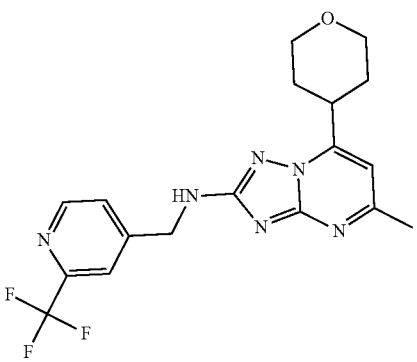 [SMILES: Cc1cc(C2CCOCC2)n2nc(NCc3ccnc(C(F)(F)F)c3)nc2n1]

¹H NMR (400 MHz, CDCl₃) δ=8.65 (d, J=5.1 Hz, 1H), 7.74 (s, 1H), 7.54 (d, J=4.7 Hz, 1H), 6.56 (s, 1H), 5.57 (t, J=6.1 Hz, 1H), 4.73 (d, J=6.3 Hz, 2H), 4.10 (dd, J=3.7, 10.8 Hz, 2H), 3.58 (dt, J=2.2, 11.8 Hz, 2H), 3.45 (tt, J=3.5, 11.9 Hz, 1H), 2.58 (s, 3H), 2.02-1.93 (m, 2H), 1.79 (dq, J=4.5, 12.5 Hz, 2H); [M+H]=393.13.

Example 60. 5-Methyl-7-(oxan-4-yl)-N-(quinolin-4-ylmethyl)-[1,2,4]triazolo[1,5-a]pyrimidin-2-amine

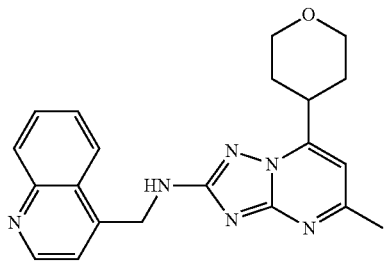 [SMILES: Cc1cc(C2CCOCC2)n2nc(NCc3ccnc4ccccc34)nc2n1]

¹H NMR (400 MHz, CDCl₃) δ=8.85 (d, J=4.7 Hz, 1H), 8.21-8.08 (m, 2H), 7.80-7.69 (m, 1H), 7.65-7.55 (m, 1H), 7.51 (d, J=4.3 Hz, 1H), 6.56 (s, 1H), 5.44 (t, J=6.1 Hz, 1H), 5.16 (d, J=6.3 Hz, 2H), 4.09 (dd, J=3.5, 11.0 Hz, 2H), 3.57 (dt, J=2.0, 11.9 Hz, 2H), 3.48 (tt, J=3.6, 12.0 Hz, 1H), 2.59 (s, 3H), 2.04-1.96 (m, 2H), 1.86-1.72 (m, 2H); [M+H]=375.5.

Example 61. 5-Methyl-N-[(3-methyl-1-phenyl-1H-pyrazol-4-yl)methyl]-7-(4-methyloxan-4-yl)-[1,2,4]triazolo[1,5-a]pyrimidin-2-amine

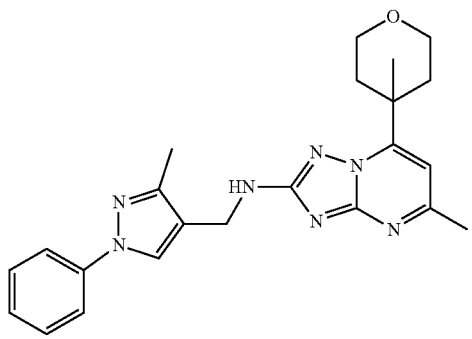

¹H NMR (400 MHz, CDCl₃) δ=7.90 (s, 1H), 7.64-7.57 (m, 2H), 7.40 (dd, J=7.4, 8.6 Hz, 2H), 7.22 (tt, J=1.2, 7.4 Hz, 1H), 6.57 (s, 1H), 5.40 (d, J=5.5 Hz, 1H), 4.48 (d, J=5.9 Hz, 2H), 3.86-3.78 (m, 2H), 3.77-3.69 (m, 2H), 2.60 (s, 3H), 2.46-2.32 (m, 5H), 2.15-2.04 (m, 2H), 1.62 (s, 3H); [M+H]=418.5.

Example 62. 5-Methyl-7-(4-methyloxan-4-yl)-N-[(1-phenyl-1H-pyrazol-4-yl)methyl]-[1,2,4]triazolo[1,5-a]pyrimidin-2-amine

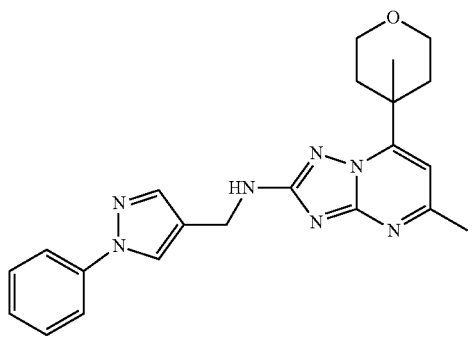

¹H NMR (400 MHz, CDCl₃) δ=7.97 (s, 1H), 7.73 (s, 1H), 7.68-7.59 (m, 2H), 7.43 (dd, J=7.4, 8.6 Hz, 2H), 7.31-7.21 (m, 1H), 6.58 (s, 1H), 5.64 (t, J=5.9 Hz, 1H), 4.54 (d, J=5.9 Hz, 2H), 3.87-3.78 (m, 2H), 3.77-3.70 (m, 2H), 2.60 (s, 3H), 2.39 (ddd, J=4.1, 9.0, 13.5 Hz, 2H), 2.16-2.05 (m, 2H), 1.62 (s, 3H); [M+H]=404.53.

Example 63. 7-Cyclopropyl-5-methyl-N-[(3-methyl-1-phenyl-1H-pyrazol-4-yl)methyl]-[1,2,4]triazolo[1,5-a]pyrimidin-2-amine

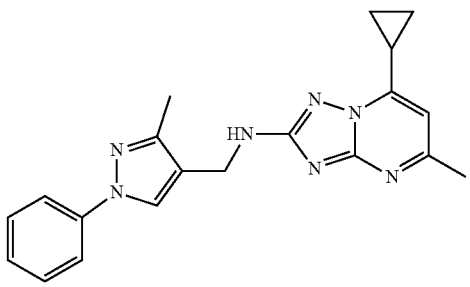 [SMILES: Cc1cc(C2CC2)n2nc(NCc3cn(-c4ccccc4)nc3C)nc2n1]

¹H NMR (400 MHz, CDCl₃) δ=7.91 (s, 1H), 7.62 (dd, J=1.2, 8.6 Hz, 2H), 7.41 (t, J=8.0 Hz, 2H), 7.25-7.20 (m, 1H), 6.19 (s, 1H), 4.85 (t, J=5.7 Hz, 1H), 4.54 (d, J=5.9 Hz, 2H), 2.63 (tt, J=5.1, 8.6 Hz, 1H), 2.53 (s, 3H), 2.39 (s, 3H), 1.36-1.28 (m, 2H), 1.15-1.07 (m, 2H); [M+H]=360.5.

Example 64. N-[(1R)-1-(4-Methoxyphenyl)ethyl]-5-methyl-7-(oxan-4-yl)-[1,2,4]triazolo[1,5-a]pyrimidin-2-amine

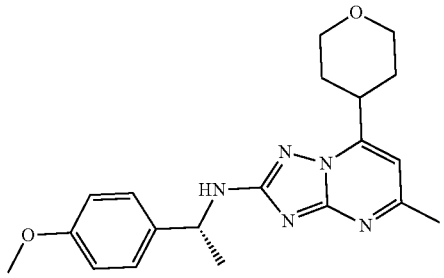

¹H NMR (400 MHz, CDCl₃) δ=7.36-7.31 (m, 2H), 6.87-6.81 (m, 2H), 6.48 (s, 1H), 5.02-4.91 (m, 2H), 4.14-4.04 (m, 2H), 3.78-3.77 (m, 3H), 3.65-3.54 (m, 2H), 3.45 (tt, J=3.4, 12.1 Hz, 1H), 2.55 (s, 3H), 2.05-1.90 (m, 2H), 1.86-1.70 (m, 2H), 1.60-1.56 (m, 3H); [M+H]=368.65.

Example 65. N-{[1-(2,2-Difluoroethyl)-3-methyl-1H-pyrazol-4-yl]methyl}-5-methyl-7-(oxan-4-yl)-[1,2,4]triazolo[1,5-a]pyrimidin-2-amine

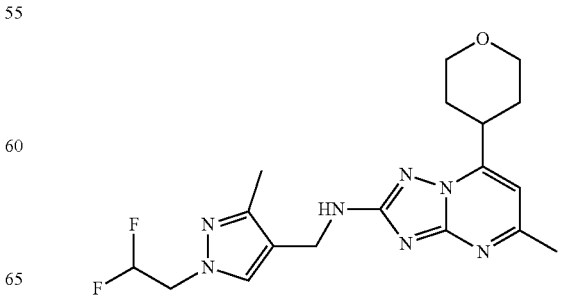

¹H NMR (400 MHz, CDCl₃) δ=7.43 (s, 1H), 6.56 (s, 1H), 6.21-5.85 (m, 1H), 4.78 (t, J=5.9 Hz, 1H), 4.44 (d, J=5.9 Hz, 2H), 4.34 (dt, J=4.3, 13.5 Hz, 2H), 4.14 (dd, J=3.7, 10.8 Hz, 2H), 3.64 (dt, J=2.0, 11.9 Hz, 2H), 3.55 (tt, J=3.7, 12.0 Hz, 1H), 2.60 (s, 3H), 2.29 (s, 3H), 2.11-2.02 (m, 2H), 1.91-1.77 (m, 2H); [M+H]=392.5.

Example 66. 5-Methyl-N-{[3-methyl-1-(propan-2-yl)-1H-pyrazol-4-yl]methyl}-7-(oxan-4-yl)-[1,2,4]triazolo[1,5-a]pyrimidin-2-amine

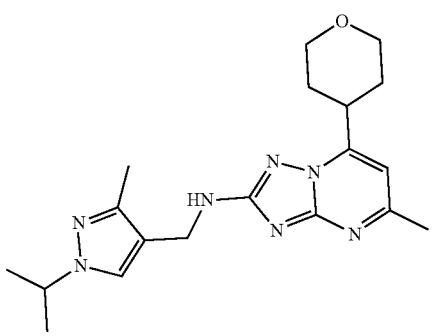 [SMILES: Cc1cc(C2CCOCC2)n2nc(NCc3cn(C(C)C)nc3C)nc2n1]

¹H NMR (400 MHz, CDCl₃) δ=7.37 (s, 1H), 6.53 (s, 1H), 4.70 (t, J=5.7 Hz, 1H), 4.45-4.40 (m, 2H), 4.39-4.31 (m, 1H), 4.17-4.12 (m, 1H), 4.12-4.08 (m, 1H), 3.63 (dt, J=2.0, 11.9 Hz, 2H), 3.54 (tt, J=3.5, 12.1 Hz, 1H), 2.61-2.54 (m, 3H), 2.31-2.22 (m, 3H), 2.06 (ddd, J=1.4, 3.3, 12.5 Hz, 2H), 1.88-1.77 (m, 2H), 1.48-1.47 (m, 1H), 1.48-1.42 (m, 6H); [M+H]=370.65.

Example 67. N-[(1-Cyclopentyl-3-methyl-1H-pyrazol-4-yl)methyl]-5-methyl-7-(oxan-4-yl)-[1,2,4]triazolo[1,5-a]pyrimidin-2-amine

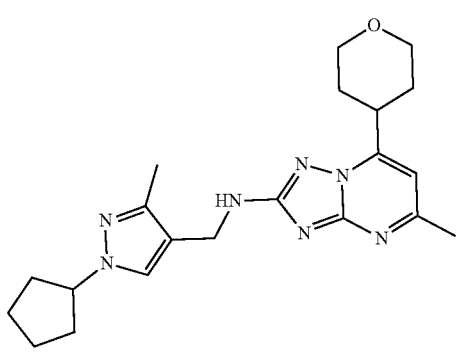 [SMILES: Cc1cc(C2CCOCC2)n2nc(NCc3cn(C4CCCC4)nc3C)nc2n1]

¹H NMR (400 MHz, CDCl₃) δ=7.36 (s, 1H), 6.53 (s, 1H), 4.72 (t, J=5.5 Hz, 1H), 4.51 (quin, J=7.2 Hz, 1H), 4.40 (d, J=5.5 Hz, 2H), 4.11 (dd, J=3.7, 11.2 Hz, 2H), 3.62 (dt, J=2.0, 11.9 Hz, 2H), 3.54 (tt, J=3.5, 12.1 Hz, 1H), 2.59-2.55 (m, 3H), 2.26 (s, 3H), 2.17-2.02 (m, 2H), 1.99-1.59 (m, 8H); [M+H]=396.86.

Example 68. N-[(2,4-Difluorophenyl)methyl]-5-methyl-7-(oxan-4-yl)-[1,2,4]triazolo[1,5-a]pyrimidin-2-amine

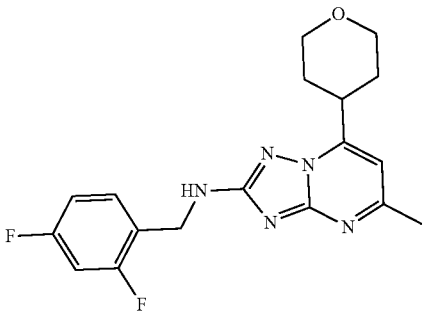 [SMILES: Cc1cc(C2CCOCC2)n2nc(NCc3ccc(F)cc3F)nc2n1]

¹H NMR (400 MHz, CDCl₃) δ=7.51-7.41 (m, 1H), 6.83-6.75 (m, 2H), 6.53 (s, 1H), 5.07 (t, J=6.5 Hz, 1H), 4.63 (d, J=6.7 Hz, 2H), 4.16-4.07 (m, 2H), 3.62 (dt, J=2.0, 11.9 Hz, 2H), 3.50 (tt, J=3.5, 11.9 Hz, 1H), 2.60-2.55 (m, 3H), 2.07-1.98 (m, 2H), 1.87-1.74 (m, 2H); [M+H]=359.17.

Example 69. N-[(1S)-1-(4-Methoxyphenyl)ethyl]-5-methyl-7-(oxan-4-yl)-[1,2,4]triazolo[1,5-a]pyrimidin-2-amine

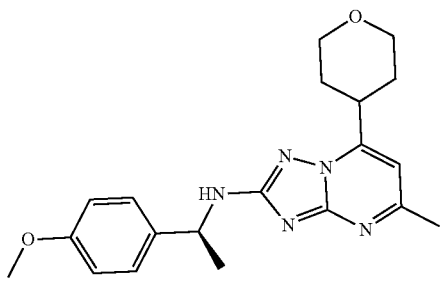

¹H NMR (400 MHz, CDCl₃) δ=7.37-7.30 (m, 2H), 6.87-6.79 (m, 2H), 6.48 (s, 1H), 5.20 (d, J=7.4 Hz, 1H), 4.96 (quin, J=6.9 Hz, 1H), 4.15-4.03 (m, 2H), 3.78-3.75 (m, 3H), 3.65-3.53 (m, 2H), 3.44 (tt, J=3.5, 12.1 Hz, 1H), 2.57-2.52 (m, 3H), 2.05-1.89 (m, 2H), 1.84-1.67 (m, 2H), 1.58 (d, J=7.0 Hz, 3H); [M+H]=367.78.

Example 70. N-[(3,5-Difluoropyridin-4-yl)methyl]-5-methyl-7-(oxan-4-yl)-[1,2,4]triazolo[1,5-a]pyrimidin-2-amine

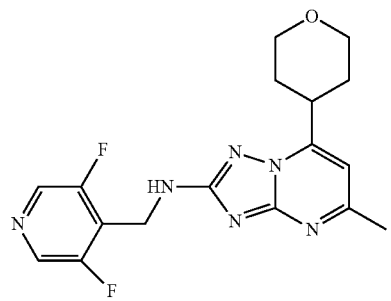 [SMILES: Cc1cc(C2CCOCC2)n2nc(NCc3c(F)cncc3F)nc2n1]

¹H NMR (400 MHz, DMSO-d₆) δ=8.45 (s, 2H), 7.59 (t, J=5.9 Hz, 1H), 6.84 (s, 1H), 4.54 (d, J=5.9 Hz, 2H), 4.00 (dd, J=3.3, 11.5 Hz, 2H), 3.49 (dt, J=1.6, 11.7 Hz, 2H), 3.42-3.34 (m, 1H), 2.47 (s, 3H), 1.88 (dd, J=1.8, 12.3 Hz, 2H), 1.77-1.63 (m, 2H); [M+H]=361.4.

Example 71. 7-Cyclobutyl-5-methyl-N-[(3-methyl-1-phenyl-1H-pyrazol-4-yl)methyl]-[1,2,4]triazolo[1,5-a]pyrimidin-2-amine

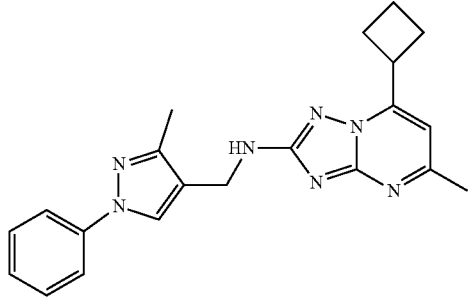 [SMILES: Cc1cc(C2CCC2)n2nc(NCc3cn(-c4ccccc4)nc3C)nc2n1]

¹H NMR (400 MHz, CDCl₃) δ=7.90 (s, 1H), 7.61 (dd, J=1.2, 8.6 Hz, 2H), 7.41 (dd, J=7.4, 8.6 Hz, 2H), 7.27-7.18 (m, 1H), 6.62 (d, J=0.8 Hz, 1H), 4.84 (t, J=5.9 Hz, 1H), 4.52 (d, J=5.9 Hz, 2H), 4.11-3.95 (m, 1H), 2.60 (s, 3H), 2.58-2.50 (m, 2H), 2.39 (s, 3H), 2.36-2.10 (m, 3H), 2.05-1.88 (m, 1H); [M+H]=374.51.

Example 72. 5-Methyl-N-[(3-methyl-1-phenyl-1H-pyrazol-4-yl)methyl]-7-(oxolan-3-yl)-[1,2,4]triazolo[1,5-a]pyrimidin-2-amine

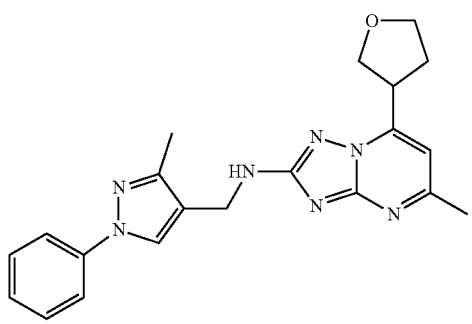 [SMILES: Cc1cc(C2CCOC2)n2nc(NCc3cn(-c4ccccc4)nc3C)nc2n1]

¹H NMR (400 MHz, CDCl₃) δ=7.91 (s, 1H), 7.65-7.57 (m, 2H), 7.40 (t, J=8.0 Hz, 2H), 7.26-7.17 (m, 1H), 6.64 (s, 1H), 5.07 (t, J=5.9 Hz, 1H), 4.52 (d, J=5.9 Hz, 2H), 4.20 (dd, J=7.0, 8.6 Hz, 1H), 4.13-3.91 (m, 4H), 2.57 (s, 3H), 2.55-2.45 (m, 1H), 2.38 (s, 3H), 2.24-2.10 (m, 1H); [M+H]=390.51.

Example 73. 4-Fluoro-3-({[5-methyl-7-(oxan-4-yl)-[1,2,4]triazolo[1,5-a]pyrimidin-2-yl]amino}methyl)benzonitrile

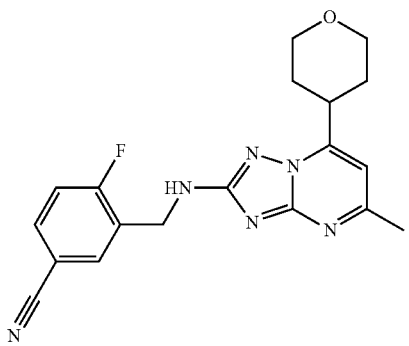 [SMILES: Cc1cc(C2CCOCC2)n2nc(NCc3cc(C#N)ccc3F)nc2n1]

¹H NMR (400 MHz, CDCl₃) δ=7.86 (dd, J=2.2, 6.8 Hz, 1H), 7.62-7.50 (m, 1H), 7.21-7.10 (m, 1H), 6.58 (s, 1H), 5.33 (t, J=6.7 Hz, 1H), 4.71 (d, J=6.7 Hz, 2H), 4.15 (dd, J=3.5, 11.0 Hz, 2H), 3.64 (dt, J=2.0, 11.9 Hz, 2H), 3.51 (tt, J=3.5, 11.9 Hz, 1H), 2.59 (s, 3H), 2.09-1.98 (m, 2H), 1.92-1.75 (m, 2H); [M+H]=367.48.

Example 74. 5-Methyl-N-[(3-methyl-1-phenyl-H-pyrazol-4-yl)methyl]-7-(propan-2-yl)-[1,2,4]triazolo[1,5-a]pyrimidin-2-amine

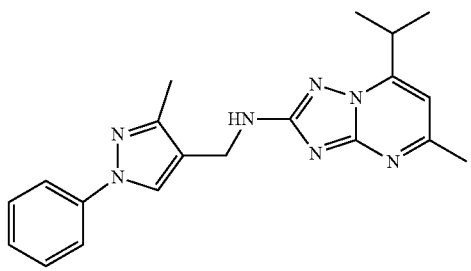 [SMILES: Cc1cc(C(C)C)n2nc(NCc3cn(-c4ccccc4)nc3C)nc2n1]

¹H NMR (400 MHz, CDCl₃) δ=7.91 (s, 1H), 7.61 (dd, J=1.2, 8.6 Hz, 2H), 7.41 (dd, J=7.4, 8.6 Hz, 2H), 7.26-7.20 (m, 1H), 6.57 (s, 1H), 4.88 (t, J=5.7 Hz, 1H), 4.53 (d, J=5.9 Hz, 2H), 3.61 (td, J=6.7, 13.9 Hz, 1H), 2.58 (s, 3H), 2.39 (s, 3H), 1.40 (d, J=7.0 Hz, 6H); [M+H]=362.50.

Example 75. N-[(4-Methoxyphenyl)methyl]-5-methyl-7-(1-methylcyclopropyl)-[1,2,4]triazolo[1,5-a]pyrimidin-2-amine

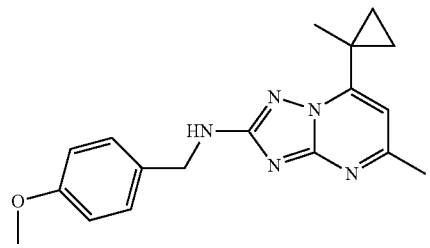 [SMILES: COc1ccc(CNc2nc3nc(C)cc(C4(C)CC4)n3n2)cc1]

¹H NMR (400 MHz, CDCl₃) δ ppm 0.87-0.95 (m, 2H) 1.12-1.20 (m, 2H) 1.53 (s, 3H) 2.55 (s, 3H) 3.80 (s, 3H) 4.58 (d, J=5.87 Hz, 2H) 4.92 (t, J=6.06 Hz, 1H) 6.58 (s, 1H) 6.86 (d, J=9.00 Hz, 2H) 7.36 (d, J=9.00 Hz, 2H); [M+H]=324.5.

Example 76. 5-Methyl-N-[(3-methyl-1-phenyl-1H-pyrazol-4-yl)methyl]-7-(1-methylcyclopropyl)-[1,2,4]triazolo[1,5-a]pyrimidin-2-amine

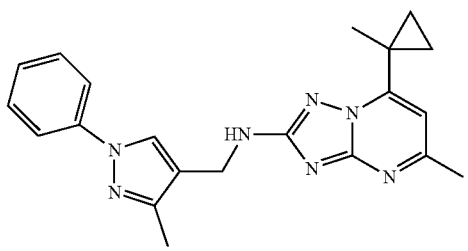 [SMILES: Cc1cc(C2(C)CC2)n2nc(NCc3cn(-c4ccccc4)nc3C)nc2n1]

¹H NMR (400 MHz, CDCl₃) δ=7.93 (s, 1H), 7.67-7.57 (m, 2H), 7.41 (dd, J=7.6, 8.4 Hz, 2H), 7.26-7.18 (m, 1H), 6.60 (s, 1H), 4.91 (t, J=5.9 Hz, 1H), 4.54 (d, J=6.3 Hz, 2H), 2.56 (s, 3H), 2.40 (s, 3H), 1.55 (s, 3H), 1.21-1.11 (m, 2H), 0.97-0.88 (m, 2H); [M+H]=374.5.

Example 77. N-[(4-Methoxyphenyl)methyl]-7-(2-methoxypropan-2-yl)-5-methyl-[1,2,4]triazolo[1,5-a]pyrimidin-2-amine

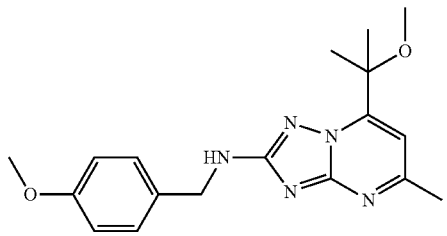

¹H NMR (400 MHz, CDCl₃) δ=7.36-7.30 (m, 2H), 6.88-6.86 (m, 1H), 6.86-6.83 (m, 2H), 4.55 (d, J=6.3 Hz, 2H), 3.79 (s, 3H), 3.36 (s, 3H), 2.59 (s, 3H), 1.76 (s, 6H); [M+H]=342.

Example 78-Example 86 were prepared in a manner analogous to Example 13, with the appropriate starting material substitutions.

Example 78. N-[(3-Chloro-2,4-difluorophenyl)methyl]-5-methyl-7-(oxan-4-yl)-[1,2,4]triazolo[1,5-a]pyrimidin-2-amine

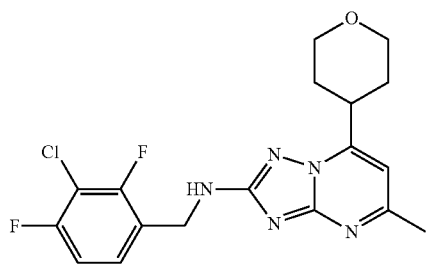 [SMILES: Cc1cc(C2CCOCC2)n2nc(NCc3ccc(F)c(Cl)c3F)nc2n1]

¹H NMR (400 MHz, CDCl₃) δ=7.39 (dt, J=6.1, 8.3 Hz, 1H), 7.28-7.22 (m, 3H), 6.90 (dt, J=2.0, 8.4 Hz, 1H), 6.54 (s, 1H), 5.08 (t, J=6.5 Hz, 1H), 4.66 (d, J=6.7 Hz, 2H), 4.12 (dd, J=4.1, 11.2 Hz, 2H), 3.68-3.58 (m, 2H), 3.49 (tt, J=3.4, 12.1 Hz, 1H), 2.61-2.55 (m, 3H), 2.02 (dd, J=1.8, 12.7 Hz, 2H), 1.86-1.75 (m, 2H); [M+H]=394.10.

Example 79. 5-Methyl-N-[(4-methyl-2-phenyl-1,3-oxazol-3-oxazol-5-yl)methyl]-7-(oxan-4-yl)-[1,2,4]triazolo[1,5-a]pyrimidin-2-amine

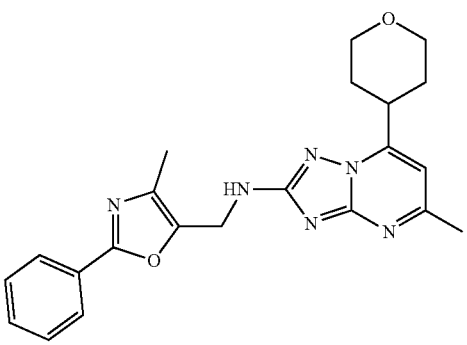 [SMILES: Cc1cc(C2CCOCC2)n2nc(NCc3oc(-c4ccccc4)nc3C)nc2n1]

¹H NMR (400 MHz, CDCl₃) δ=8.01-7.91 (m, 2H), 7.43-7.37 (m, 3H), 6.54 (s, 1H), 5.17 (t, J=6.1 Hz, 1H), 4.65 (d, J=6.3 Hz, 2H), 4.12 (dd, J=3.9, 11.3 Hz, 2H), 3.66-3.46 (m, 3H), 2.58 (s, 3H), 2.32 (s, 3H), 2.08-2.01 (m, 2H), 1.88-1.75 (m, 2H); [M+H]=406.06.

Example 80. N-[(5-Chloro-2,4-difluorophenyl)methyl]-5-methyl-7-(oxan-4-yl)-[1,2,4]triazolo[1,5-a]pyrimidin-2-amine

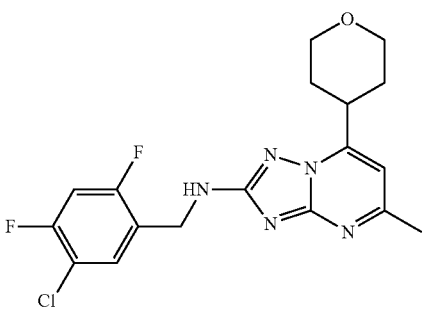 [SMILES: Cc1cc(C2CCOCC2)n2nc(NCc3cc(Cl)c(F)cc3F)nc2n1]

¹H NMR (400 MHz, CDCl₃) δ=7.57 (t, J=7.8 Hz, 1H), 6.90 (t, J=9.2 Hz, 1H), 6.55 (s, 1H), 5.13 (t, J=6.5 Hz, 1H), 4.60 (d, J=6.7 Hz, 2H), 4.13 (dd, J=3.5, 11.0 Hz, 2H), 3.64 (dt, J=2.0, 11.9 Hz, 2H), 3.57-3.45 (m, 1H), 2.58 (s, 3H), 2.08-2.00 (m, 2H), 1.88-1.75 (m, 2H); [M+H]=394.1.

Example 81. N-[(3-Bromo-5-fluorophenyl)methyl]-5-methyl-7-(oxan-4-yl)-[1,2,4]triazolo[1,5-a]pyrimidin-2-amine

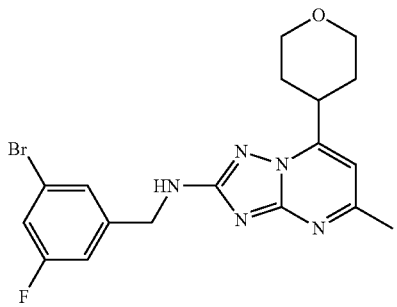 [SMILES: Cc1cc(C2CCOCC2)n2nc(NCc3cc(F)cc(Br)c3)nc2n1]

¹H NMR (400 MHz, CDCl₃) δ=7.36 (s, 1H), 7.16-7.03 (m, 2H), 6.55 (s, 1H), 5.19 (br s, 1H), 4.60 (d, J=6.7 Hz, 2H), 4.12 (dd, J=3.5, 11.0 Hz, 2H), 3.62 (dt, J=2.0, 11.9 Hz, 2H), 3.50 (tt, J=3.5, 11.9 Hz, 1H), 2.58 (s, 3H), 2.08-1.99 (m, 2H), 1.88-1.74 (m, 2H); [M+H]=420.25/422.24.

Example 82. 5-Methyl-N-[(1-methyl-3-phenyl-1H-pyrazol-5-yl)methyl]-7-(oxan-4-yl)-[1,2,4]triazolo[1,5-a]pyrimidin-2-amine

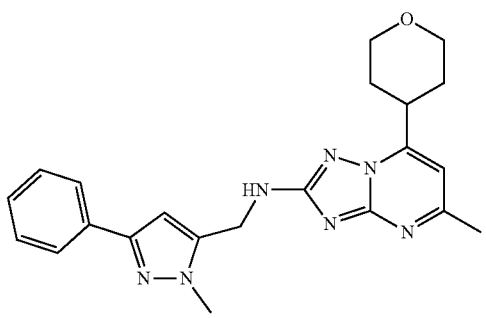 [SMILES: Cc1cc(C2CCOCC2)n2nc(NCc3cc(-c4ccccc4)nn3C)nc2n1]

¹H NMR (400 MHz, CDCl₃) δ=7.77-7.71 (m, 2H), 7.40-7.33 (m, 2H), 7.30-7.24 (m, 1H), 6.56 (d, J=9.4 Hz, 2H), 4.98 (t, J=5.9 Hz, 1H), 4.69 (d, J=5.9 Hz, 2H), 4.12 (dd, J=3.5, 11.0 Hz, 2H), 3.96 (s, 3H), 3.62 (dt, J=2.0, 11.7 Hz, 2H), 3.57-3.47 (m, 1H), 2.59 (s, 3H), 2.09-2.01 (m, 2H), 1.82 (dq, J=4.3, 12.4 Hz, 2H); [M+H]=404.2.

Example 83. N-[(3-Bromo-2-fluorophenyl)methyl]-5-methyl-7-(oxan-4-yl)-[1,2,4]triazolo[1,5-a]pyrimidin-2-amine

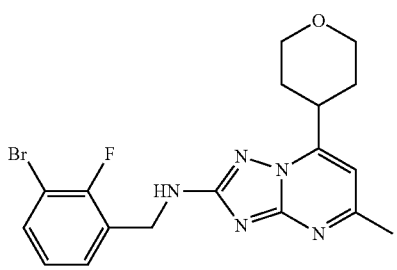 [SMILES: Cc1cc(C2CCOCC2)n2nc(NCc3cccc(Br)c3F)nc2n1]

¹H NMR (400 MHz, CDCl₃) δ=7.48-7.39 (m, 2H), 6.95 (t, J=8.0 Hz, 1H), 6.53 (s, 1H), 5.12 (t, J=6.7 Hz, 1H), 4.69 (d, J=6.3 Hz, 2H), 4.11 (dd, J=3.9, 11.3 Hz, 2H), 3.63 (dt, J=2.0, 11.7 Hz, 2H), 3.50 (tt, J=3.5, 11.9 Hz, 1H), 2.57 (s, 3H), 2.06-1.98 (m, 2H), 1.85-1.73 (m, 2H); [M+H]=420.23/422.25.

Example 84. N-[(3-Chloro-5-fluorophenyl)methyl]-5-methyl-7-(oxan-4-yl)-[1,2,4]triazolo[1,5-a]pyrimidin-2-amine

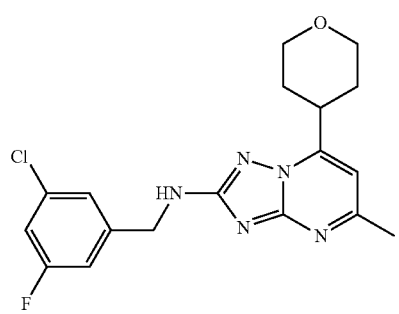 [SMILES: Cc1cc(C2CCOCC2)n2nc(NCc3cc(F)cc(Cl)c3)nc2n1]

¹H NMR (400 MHz, CDCl₃) δ=7.20 (t, J=1.4 Hz, 1H), 7.05-7.01 (m, 1H), 6.97 (td, J=2.2, 8.6 Hz, 1H), 6.55 (s, 1H), 5.15 (t, J=6.3 Hz, 1H), 4.60 (d, J=6.7 Hz, 2H), 4.12 (dd, J=3.5, 11.0 Hz, 2H), 3.62 (dt, J=2.0, 11.9 Hz, 2H), 3.55-3.45 (m, 1H), 2.60-2.57 (m, 3H), 2.06-1.98 (m, 2H), 1.87-1.74 (m, 2H); [M+H]=376.1.

Example 85. 5-Methyl-N-{[1-methyl-3-(trifluoromethyl)-1H-pyrazol-5-yl]methyl}-7-(oxan-4-yl)-[1,2,4]triazolo[1,5-a]pyrimidin-2-amine

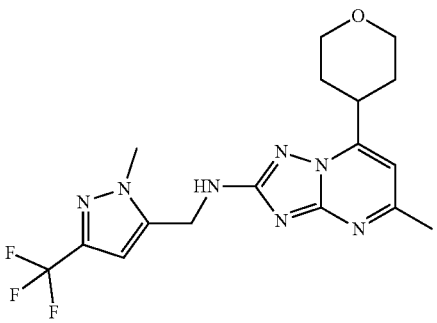 [SMILES: Cc1cc(C2CCOCC2)n2nc(NCc3cc(C(F)(F)F)nn3C)nc2n1]

¹H NMR (400 MHz, CDCl₃) δ=6.59 (s, 1H), 6.52 (s, 1H), 5.05 (br s, 1H), 4.68 (d, J=6.3 Hz, 2H), 4.13 (dd, J=3.5, 11.0 Hz, 2H), 3.98 (s, 3H), 3.62 (dt, J=2.2, 11.8 Hz, 2H), 3.56-3.43 (m, 1H), 2.60 (s, 3H), 2.08-1.98 (m, 2H), 1.90-1.76 (m, 2H); [M+H]=396.1.

Example 86. 3-({[5-Methyl-7-(oxan-4-yl)-[1,2,4]triazolo[1,5-a]pyrimidin-2-yl]amino}methyl)benzonitrile

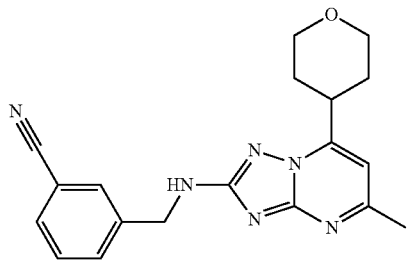 [SMILES: Cc1cc(C2CCOCC2)n2nc(NCc3cccc(C#N)c3)nc2n1]

$^1$H NMR (400 MHz, CDCl$_3$) δ=7.72 (s, 1H), 7.65 (d, J=7.8 Hz, 1H), 7.54 (td, J=1.5, 7.6 Hz, 1H), 7.45-7.39 (m, 1H), 6.57 (s, 1H), 5.25 (br s, 1H), 4.67 (d, J=6.3 Hz, 2H), 4.12 (dd, J=3.9, 11.3 Hz, 2H), 3.62 (dt, J=2.0, 11.9 Hz, 2H), 3.50 (tt, J=3.5, 11.9 Hz, 1H), 2.59 (s, 3H), 2.06-1.98 (m, 2H), 1.81 (dq, J=4.3, 12.5 Hz, 2H); [M+H]=349.2.

PHARMACOLOGICAL EXAMPLES

The present disclosure will be further illustrated by the following pharmacological examples. These examples are understood to be exemplary only and are not intended to limit the scope of the embodiments disclosed herein.

Enzymatic Assay

An IMAP TR-FRET-based phosphodiesterase assay was developed using the PDE2A isoform. IMAP technology is based on high-affinity binding of phosphate by immobilized metal (MIII) coordination complexes on nanoparticles. The IMAP "binding reagent" recognizes phosphate groups on AMP or GMP generated from cAMP or cGMP in a PDE reaction. Cyclic nucleotides that carry a phosphodiester bond and not a free phosphate are not recognized by the binding reagent. The time resolved fluorescence resonance energy transfer (TR-FRET) is afforded by a Terbium (Tb)-Donor pre-bound to the nanoparticles. FRET occurs when the fluorescent-labeled AMP or GMP product of a PDE reaction binds and comes into close proximity to the Tb-Donor complex. Due to the long lifetime of Tb fluorescence, detection can be run in time-resolved mode to reduce or eliminate interference from auto-fluorescent compounds.

The IMAP TR-FRET PDE2A assay was performed in 1536-well white plates. A total of 250 pg per well of FLAG-tagged PDE2A1 (amino acids 2-941) was dispensed in 2.5 µL IMAP assay buffer consisting of 10 mM Tris pH 7.2, 10 mM MgCl$_2$, 1 mM DTT, and 0.1% fatty acid free BSA. 30 nL of compound was then added from 1 mM stocks in DMSO using a Kalypsys Pintool. Plates were incubated for 5 min at room temperature before dispensing 1.5 µL of 533 nM FAM-cAMP substrate for a final concentration of 200 nM. Following a brief centrifugation, plates were incubated for 30 min at room temperature. The assay was terminated by adding 5 µL IMAP binding reagent Tb complex to each well which was prepared according to manufacturer's recommendations (Molecular Devices). Plates were incubated an additional 90 minutes at room temperature and read on a Viewlux plate reader. All compounds were solvated at a concentration of 10 mM in DMSO and tested in 11-point half-log dose-response. Curve fitting and IC$_{50}$ values were determined using a standard four parameter fit.

| PDE2 (PIC$_{50}$) | Example Numbers |
|---|---|
| >7 | 13, 15, 17, 19, 20, 21, 23, 25, 29, 30, 31, 36, 37, 38, 39, 40, 41, 42, 46, 50, 52, 53, 54, 55, 59, 60, 61, 62, 66, 67, 72, 74, 76, 78, 79, 80, 81, 82, 83, 84, 85, |
| 6-7 | 1, 5, 6, 9, 11, 14, 16, 18, 22, 24, 26, 27, 28, 32, 33, 34, 35, 43, 44, 45, 47, 48, 49, 51, 56, 57, 58, 63, 64, 65, 68, 70, 71, 73, 75, 86 |
| 5-6 | 2, 3, 4, 7, 8, 10, 12, 69, 77 |

BIOLOGICAL EXAMPLES

The present disclosure will be further illustrated by the following biological examples. These examples are understood to be exemplary only and are not intended to limit the scope of the embodiments disclosed herein.

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present embodiments, as will be understood by those of ordinary skill in the art. These assays can be directed towards the evaluation of, without limitation, hippocampus-, cortex-, and/or amygdala-dependent memory formation or cognitive performance.

Biological Example 1

Effect of PDE2 Inhibitors on Contextual Memory
Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, Behav. Neurosci. 1984, 98, 269-277; Fanselow, Behav. Neurosci. 1984, 98, 79-95; and Phillips and LeDoux, Behav. Neurosci. 1992, 106, 274-285).

Contextual conditioning has been extensively used to investigate the neural substrates mediating fear-motivated learning (e.g., Phillips and LeDoux, Behav. Neurosci. 1992, 106, 274-285; Kim et al., Behav. Neurosci. 1993, 107, 1093-1098; and Bourtchouladze et al., Learn. Mem. 1998, 5, 365-374). Studies in mice and rats have provided evidence for functional interaction between hippocampal and nonhippocampal systems during contextual conditioning training (e.g., Maren et al., *Behav. Brain Res.* 1997, 88, 261-274; Maren et al., *Neurobiol. Learn. Mem.* 1997, 67, 142-149; and Frankland et al., *Behav. Neurosci.* 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning, as well as strain and genetic background differences in mice (e.g., Bourtchouladze et al., *Cell* 1994, 79, 59-68; Bourtchouladze et al., *Learn Mem.* 1998, 5, 365-374; Kogan et al., *Current Biology* 1997, 7, 1-11; Silva et al., *Current Biology* 1996, 6, 1509-1518; Abel et al., *Cell* 1997, 88, 615-626; Giese et al., *Science* 1998, 279, 870-873; Logue et al., *Neuroscience* 1997, 80, 1075-1086; Chen et al., *Behav. Neurosci.* 1996, 110, 1177-1180; and Nguyen et al., *Learn Mem.* 2000, 7, 170-179).

Because robust learning can be triggered with a few minutes training session, contextual conditioning has been especially useful to study the biology of temporally distinct processes of short- and long-term memory (e.g., Kim et al., *Behav. Neurosci.* 1993, 107, 1093-1098; Bourtchouladze et al., *Cell* 1994, 79, 59-68; Abel et al., *Cell* 1997, 88, 615-626; Logue et al., *Behav. Neurosci.* 1997, 111, 104-113; Bourtchouladze et al., *Learn. Mem.* 1998, 5, 365-374; and Nguyen et al., *Learn. Mem.* 2000, 7, 170-179). As such, contextual conditioning provides an excellent model to evaluate the effects of novel drug compounds on hippocampal-dependent memory formation.

Procedures

Previous investigations have established that training with 1× or 2×CS-US pairings induces sub-maximal (weak) memory in wild-type mice (e.g., U.S.2009/0053140; Tully et al., *Nat. Rev. Drug Discov.* 2003, 2, 267-77; and Bourtchouladze et al., *Learn. Mem.* 1998, 5, 365-374). Such sub-maximal memory is facilitated by augmenting CREB, while inhibition of CREB impairs maximal memory induced with 5×CS-US pairings (Barad et al., *Proc Natl Acad Sci.* 1998, 95, 15020-15025; Peters et al., *Genes Brain Behav.* 2009, 8, 320-329). Accordingly, contextual conditioning in this study was performed as described by Barad et al., *Proc Natl Acad Sci.* 1998, 95, 15020-15025 and Peters et al., *Genes Brain Behav.* 2009, 8, 320-329.

Long-Evans male rats (each weighting about 330-450 grams) were used for contextual conditioning. Rats were group-housed in standard laboratory and maintained on a 12:12 light-dark cycle. The experiments were always conducted during the light phase of the cycle. Except for testing times, the animals had ad libidum access to food and water. To assess contextual memory, a modified contextual fear conditioning task originally developed for evaluation of memory in CREB knock-out mice was used (Bourtchouladze et al., 1994). Training sessions comprised a baseline period in the conditioning chamber (Med Associates, Inc.) followed by presentation of unconditioned stimuli (1-5 footshocks each at 0.2-1.0 mA for 2-sec) spaced at 60-sec intervals. Thirty seconds following the last shock, the animal was returned to its home cage. One to 7 days later, the animals were returned to the chamber and freezing behavior was scored. Freezing (complete immobility except respiration) was scored by Video Freeze software (Med Associates, Inc.) over an 8 minute test period. Treatment with cognition enhancers is expected to significantly increase freezing when compared to controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate post-hoc tests using GraphPad Prism software package.

Results

Exemplary compounds of Formula (I) were tested for enhancement of contextual memory in the fear conditioning assay. For one or more compounds, significant enhancing effects were seen at several concentrations, including 0.03 mg/kg, and 0.3 mg/kg, and 1 mg/kg.

Biological Example 2

Effect of PDE2 Inhibitors on Novel Object Recognition

Rationale

Novel Object Recognition (NOR) is an assay of recognition learning and memory retrieval; it takes advantage of the spontaneous preference of rodents to investigate a novel object compared with a familiar one. It is an ethologically relevant task, which in contrast to fear conditioning, does not result from negative reinforcement (foot shock) (e.g., Ennaceur and Delacour, *Behav. Brain Res.* 1988, 31, 47-59).

The NOR test has been employed extensively to assess the potential cognitive-enhancing properties of novel compounds derived from high-throughput screening. In object recognition, the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., *Proc. Natl. Acad. Sci. USA* 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, *Behav. Brain Res.* 1998, 97, 107-113; Teng et al., *J. Neurosci.* 2000, 20, 3853-3863; Mumby, *Brain Res.* 2001, 127, 159-181; Eichenbaum et al., *Annu. Rev. Neurosci.* 2007, 30, 127-152; Squire et al., *Nat. Rev. Neurosci.* 2007, 8, 872-883; and Vann and Alabasser, *Curr. Opin. Neurobiol.* 2011, 21, 440-445). Hence, object recognition provides an excellent behavioral model to evaluate drug-compound effects on cognitive tasks associated with function of the hippocampus and cortex.

Procedures

Object recognition was tested in Long-Evans male rats (each weighing about 330-450 grams) using the following protocol. Animals were briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 h later.

For novel object recognition, one object was replaced with one that is novel. All combinations and locations of objects were used in a balanced manner to reduce potential biases attributable to preference for particular locations or objects. Training and test trials were recorded and scored by video-tracking software (e.g. Noldus Ethovision). An animal was scored as exploring an object when its head was oriented toward the object within a distance of 1-2 cm (rat) or when its nose was touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., Proc. Natl. Acad. Sci. USA 2003, 100, 10518-10522). In each experiment, the experimenter was unaware (blind) to the treatment of the subjects during training and testing. Data were analyzed by one-way ANOVA with appropriate post-hoc tests using GraphPad Prism or JMP software package.

Results

Exemplary compounds of Formula (I) are tested for enhancement of memory in the NOR assay. For one or more compounds, significant enhancing effects are seen.

The specification, including the examples, is intended to be exemplary only, and it will be apparent to those skilled in the art that various modifications and variations can be made in the present embodiments without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound of Formula (I):

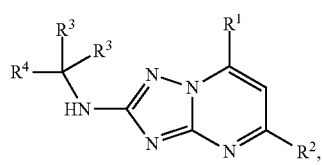

(I)

or pharmaceutically acceptable salts thereof,
wherein,
$R^1$ is —$C_{3-6}$cycloalkyl unsubstituted or substituted with one or more members selected from halo and —$C_{1-4}$alkyl; or $R^1$ is carbon-linked heterocycloalkyl selected from oxolan-2-yl, oxolan-3-yl, oxan-3-yl, oxan-4-yl, 3,6-dihydro-2H-pyran-4-yl, and piperidin-4-yl, each optionally substituted with halo, —$C_{1-4}$alkyl, or —C(=O)$CH_3$;
$R^2$ is —$C_{1-6}$alkyl, —$C_{1-6}$haloalkyl, or —$C_{3-6}$cycloalkyl;
each $R^3$ is independently —H, or —$C_{1-4}$alkyl; and $R^4$ is selected from the group consisting of:
(a) phenyl unsubstituted or substituted with one or more $R^a$, wherein each $R^a$ is independently selected from the group consisting of: —$C_{1-6}$alkyl, —$C_{1-6}$haloalkyl, —$OC_{1-6}$alkyl, —CN, and -halo, or optionally two $R^a$ come together to form a cyclopentyl, furan, dioxane, or 2,2-difluorodioxolane; and
(b) heteroaryl unsubstituted or substituted with one or more members, each independently selected from the group consisting of: halo, —$C_{1-6}$alkyl, —$C_{1-6}$haloalkyl, -cycloalkyl, phenyl, 2-methylphenyl and 3-methoxyphenyl.

2. The compound of claim 1, wherein $R^1$ is selected from the group consisting of cyclopropyl, 1-methylcyclopropyl, cyclobutyl, cyclopentyl, 4,4-difluorocyclohexyl, and carbon-linked heterocycloalkyl selected from oxolan-2-yl, oxolan-3-yl, oxan-3-yl, oxan-4-yl, -3,6-dihydro-2H-pyran-4-yl, and piperidin-4-yl, each unsubstituted or substituted with halo, —$C_{1-4}$alkyl, or —C(=O)$CH_3$.

3. The compound of claim 1, wherein $R^1$ is selected from the group consisting of cyclopropyl, 1-methylcyclopropyl, cyclobutyl, cyclopentyl, 4,4-difluorocyclohexyl, oxolan-2-yl, oxolan-3-yl, oxan-3-yl, -4-methyloxan-4-yl, 4-fluorooxan-4-yl, -3,6-dihydro-2H-pyran-4-yl, -oxan-4-yl, and 1-acetyl-piperidin-4-yl.

4. The compound of claim 1, wherein $R^2$ is —$C_{1-6}$alkyl, —$C_{1-6}$haloalkyl, or -cyclopropyl.

5. The compound of claim 1, wherein $R^2$ is —$CH_3$, —$CHF_2$, —$CH_2F$, —$CF_3$, or -cyclopropyl.

6. The compound of claim 1, wherein each $R^3$ is independently —H or —$CH_3$.

7. The compound of claim 1, wherein $R^4$ is phenyl substituted with one, two, three or four $R^a$ members, each independently selected from the group consisting of: —$C_{1-6}$alkyl, —$C_{1-6}$haloalkyl, —$OC_{1-6}$alkyl, —CN, —Br, —Cl, and —F, or optionally two $R^a$ members come together to form a cyclopentyl, furan, dioxane, or 2,2-difluorodioxolane ring.

8. The compound of claim 1, wherein each $R^a$ is independently —$C_{1-6}$alkyl, —$C_{1-6}$haloalkyl, —$OCH_3$, —CN, —Br, —Cl, or —F.

9. The compound of claim 1, wherein $R^4$ is selected from the group consisting of 2,2-difluoro-2H-1,3-benzodioxol-5-yl, 2,3-dihydro-1,4-benzodioxin-6-yl, 2,3-dihydro-1-benzofuran-5-yl, 2,3-dihydro-1-benzofuran-5-yl, 2,3-dihydro-1-benzofuran-6-yl, 2,3-dihydro-1H-inden-5-yl, 2,4-difluorophenyl, 2,5-difluorophenyl, 2,6-difluoro-4-methoxyphenyl, 2,6-difluorophenyl, 2-chlorophenyl, 2-fluoro-4-methoxyphenyl, 2-fluoro-5-methoxyphenyl, 2-fluoro-5-methylphenyl, 2-fluorophenyl, 2-methylphenyl, 3,4-difluorophenyl, 3,5-difluorophenyl, 3-bromo-2-fluorophenyl, 3-bromo-5-fluorophenyl, 3-bromophenyl, 3-chloro-2,4-difluorophenyl, 3-chloro-4-methoxyphenyl, 3-chloro-5-fluorophenyl, 3-chlorophenyl, 3-cyanophenyl, 3-fluorophenyl, 3-methoxyphenyl, 3-methylphenyl, 3-trifluoromethylphenyl, 4-fluorobenzonitrile, 4-fluorophenyl, 4-methoxyphenyl, 5-chloro-2,4-difluorophenyl, 5-chloro-2-fluorophenyl, difluoromethyl-4-methoxyphenyl, difluoromethylphenyl, and phenyl.

10. The compound of claim 1, wherein $R^4$ is selected from the group consisting of (2,2-difluoroethyl)-3-methyl-1H-pyrazol-4-yl, 1-(2-methylphenyl)-1H-pyrazol-4-yl, 1-cyclopentyl-3-methyl-1H-pyrazol-4-yl, 1-methyl-3-(trifluoromethyl)-1H-pyrazol-5-yl, 1-methyl-3-phenyl-1H-pyrazol-5-yl, 1-phenyl-1H-pyrazol-4-yl, 2-(trifluoromethyl)pyridin-4-yl, 2,6-dimethylpyridin-4-yl, 2-methylpyridin-4-yl, 3,5-difluoropyridin-4-yl, 3-methyl-1-(propan-2-yl)-1H-pyrazol- 4-yl, 3-methyl-1-phenyl-1H-pyrazol-4-yl, 3-phenyl-1,2-oxazol-5-yl, 4-methyl-2-phenyl-1,3-oxazol-5-yl, 5-methylpyridin-3-yl, difluoromethylpyridin-4-yl, and quinolin-4-yl.

11. The compound of claim 1, wherein $R^2$ is —$C_{1-4}$alkyl; and $R^4$ is phenyl substituted with one, two, or three $R^a$ members, each independently selected from the group consisting of: —$C_{1-6}$alkyl, —$C_{1-6}$haloalkyl, —$OC_{1-6}$alkyl, —Br, —Cl, and —F.

12. The compound of claim 1, wherein $R^1$ is an oxan-4-yl optionally substituted with halo, —$C_{1-4}$alkyl, or —C(=O)CH$_3$; and $R^2$ is —$C_{1-4}$alkyl.

13. The compound of claim 1, wherein $R^3$ is —H; and $R^4$ is selected from the group consisting of 2,4-difluorophenyl, 2,5-difluorophenyl, 2,6-difluoro-4-methoxyphenyl, 2,6-difluorophenyl, 2-chlorophenyl, 2-fluoro-4-methoxyphenyl, 2-fluoro-5-methoxyphenyl, 2-fluoro-5-methylphenyl, 2-fluorophenyl, 2-methylphenyl, 3,4-difluorophenyl, 3,5-difluorophenyl, 3-bromo-2-fluorophenyl, 3-bromo-5-fluorophenyl, 3-bromophenyl, 3-chloro-2,4-difluorophenyl, 3-chloro-4-methoxyphenyl, 3-chloro-5-fluorophenyl, 3-chlorophenyl, 3-fluorophenyl, 3-methoxyphenyl, 3-methylphenyl, 3-trifluoromethylphenyl, 4-fluorophenyl, 4-methoxyphenyl, 5-chloro-2,4-difluorophenyl, 5-chloro-2-fluorophenyl, difluoromethyl-4-methoxyphenyl, and difluoromethylphenyl.

14. The compound of claim 1, wherein $R^1$ is oxan-4-yl; and $R^2$ is —CH$_3$.

15. A compound selected from the group consisting of:
N-[(4-Methoxyphenyl)methyl]-5-methyl-7-(oxan-4-yl)-[1,2,4]triazolo[1,5-a]pyrimidin-2-amine;
7-Cyclopropyl-N-(2,3-dihydro-1-benzofuran-5-ylmethyl)-5-methyl-[1,2,4]triazolo[1,5-a]pyrimidin-2-amine;
7-Cyclopropyl-N-(2,3-dihydro-1-benzofuran-6-ylmethyl)-5-methyl-[1,2,4]triazolo[1,5-a]pyrimidin-2-amine;
7-Cyclopropyl-N-[(4-methoxyphenyl)methyl]-5-methyl-[1,2,4]triazolo[1,5-a]pyrimidin-2-amine;
7-Cyclopentyl-N-(2,3-dihydro-1H-inden-5-ylmethyl)-5-methyl-[1,2,4]triazolo[1,5-a]pyrimidin-2-amine;
N-(2,3-Dihydro-1H-inden-5-ylmethyl)-5-methyl-7-(propan-2-yl)-[1,2,4]triazolo[1,5-a]pyrimidin-2-amine;
N-[(3-Chlorophenyl)methyl]-5-methyl-7-(propan-2-yl)-[1,2,4]triazolo[1,5-a]pyrimidin-2-amine;
N-Benzyl-5-methyl-7-(propan-2-yl)-[1,2,4]triazolo[1,5-a]pyrimidin-2-amine;
7-tert-Butyl-N-[(3-chlorophenyl)methyl]-5-methyl-[1,2,4]triazolo[1,5-a]pyrimidin-2-amine;
N-[(4-Methoxyphenyl)methyl]-5-methyl-7-(propan-2-yl)-[1,2,4]triazolo[1,5-a]pyrimidin-2-amine;
7-(Butan-2-yl)-N-[(4-methoxyphenyl)methyl]-5-methyl-[1,2,4]triazolo[1,5-a]pyrimidin-2-amine;
N-[(4-Methoxyphenyl)methyl]-5-methyl-7-(oxolan-2-yl)-[1,2,4]triazolo[1,5-a]pyrimidin-2-amine;
N-[(5-Chloro-2-fluorophenyl)methyl]-5-methyl-7-(oxan-4-yl)-[1,2,4]triazolo[1,5-a]pyrimidin-2-amine;
N-[(3,5-Difluorophenyl)methyl]-5-methyl-7-(oxan-4-yl)-[1,2,4]triazolo[1,5-a]pyrimidin-2-amine;
N-[(2-Fluoro-4-methoxyphenyl)methyl]-5-methyl-7-(oxan-4-yl)-[1,2,4]triazolo[1,5-a]pyrimidin-2-amine;
N-(2,3-Dihydro-1,4-benzodioxin-6-ylmethyl)-5-methyl-7-(oxan-4-yl)-[1,2,4]triazolo[1,5-a]pyrimidin-2-amine;
5-Methyl-7-(oxan-4-yl)-N-[(1-phenyl-1H-pyrazol-4-yl)methyl]-[1,2,4]triazolo[1,5-a]pyrimidin-2-amine;
1-[4-(2-{[(4-Methoxyphenyl)methyl]amino}-5-methyl-[1,2,4]triazolo[1,5-a]pyrimidin-7-yl)piperidin-1-yl]ethan-1-one;
1-{4-[2-({[3-(Difluoromethyl)-4-methoxyphenyl]methyl}amino)-5-methyl-[1,2,4]triazolo[1,5-a]pyrimidin-7-yl]piperidin-1-yl}ethan-1-one;
1-{4-[2-({[3-(Difluoromethyl)phenyl]methyl}amino)-5-methyl-[1,2,4]triazolo[1,5-a]pyrimidin-7-yl]piperidin-1-yl}ethan-1-one;
N-[(3-Chloro-4-methoxyphenyl)methyl]-5-methyl-7-(oxan-4-yl)-[1,2,4]triazolo[1,5-a]pyrimidin-2-amine;
7-(4,4-Difluorocyclohexyl)-N-[(4-methoxyphenyl)methyl]-5-methyl-[1,2,4]triazolo[1,5-a]pyrimidin-2-amine;
N-{[3-(Difluoromethyl)phenyl]methyl}-5-methyl-7-(oxan-4-yl)-[1,2,4]triazolo[1,5-a]pyrimidin-2-amine;
N-[(3-Methoxyphenyl)methyl]-5-methyl-7-(oxan-4-yl)-[1,2,4]triazolo[1,5-a]pyrimidin-2-amine;
N-{[3-(Difluoromethyl)-4-methoxyphenyl]methyl}-5-methyl-7-(oxan-4-yl)-[1,2,4]triazolo[1,5-a]pyrimidin-2-amine;
N-[(2-Fluorophenyl)methyl]-5-methyl-7-(oxan-4-yl)-[1,2,4]triazolo[1,5-a]pyrimidin-2-amine;
N-[(2-Fluoro-5-methylphenyl)methyl]-5-methyl-7-(oxan-4-yl)-[1,2,4]triazolo[1,5-a]pyrimidin-2-amine;
5-Methyl-N-[(3-methylphenyl)methyl]-7-(oxan-4-yl)-[1,2,4]triazolo[1,5-a]pyrimidin-2-amine;
5-(Difluoromethyl)-N-[(4-methoxyphenyl)methyl]-7-(oxan-4-yl)-[1,2,4]triazolo[1,5-a]pyrimidin-2-amine;
5-(Fluoromethyl)-N-[(4-methoxyphenyl)methyl]-7-(oxan-4-yl)-[1,2,4]triazolo[1,5-a]pyrimidin-2-amine;
N-{[1-(3-Methoxyphenyl)-1H-pyrazol-4-yl]methyl}-5-methyl-7-(oxan-4-yl)-[1,2,4]triazolo[1,5-a]pyrimidin-2-amine;
N-[(2-Fluoro-5-methoxyphenyl)methyl]-5-methyl-7-(oxan-4-yl)-[1,2,4]triazolo[1,5-a]pyrimidin-2-amine;
N-Benzyl-5-methyl-7-(oxan-4-yl)-[1,2,4]triazolo[1,5-a]pyrimidin-2-amine;
N-[(4-Methoxyphenyl)methyl]-5-methyl-7-(4-methyloxan-4-yl)-[1,2,4]triazolo[1,5-a]pyrimidin-2-amine;
5-Methyl-N-[(2-methylpyridin-4-yl)methyl]-7-(oxan-4-yl)-[1,2,4]triazolo[1,5-a]pyrimidin-2-amine;
5-Methyl-N-{[1-(2-methylphenyl)-1H-pyrazol-4-yl]methyl}-7-(oxan-4-yl)-[1,2,4]triazolo[1,5-a]pyrimidin-2-amine;
5-Methyl-7-(oxan-4-yl)-N-[(3-phenyl-1,2-oxazol-5-yl)methyl]-[1,2,4]triazolo[1,5-a]pyrimidin-2-amine;
N-[(4-Methoxyphenyl)methyl]-5-methyl-7-(oxan-3-yl)-[1,2,4]triazolo[1,5-a]pyrimidin-2-amine;
N-[(3-Bromophenyl)methyl]-5-methyl-7-(oxan-4-yl)-[1,2,4]triazolo[1,5-a]pyrimidin-2-amine;
N-[(3-Chlorophenyl)methyl]-5-methyl-7-(oxan-4-yl)-[1,2,4]triazolo[1,5-a]pyrimidin-2-amine;
5-Methyl-7-(oxan-4-yl)-N-{[3-(trifluoromethyl)phenyl]methyl}-[1,2,4]triazolo[1,5-a]pyrimidin-2-amine;
N-(2,3-Dihydro-1-benzofuran-5-ylmethyl)-5-methyl-7-(oxan-4-yl)-[1,2,4]triazolo[1,5-a]pyrimidin-2-amine;
5-Methyl-7-(4-methyloxan-4-yl)-N-[(2-methylpyridin-4-yl)methyl]-[1,2,4]triazolo[1,5-a]pyrimidin-2-amine;
N-[(4-Methoxyphenyl)methyl]-5-methyl-7-(oxolan-3-yl)-[1,2,4]triazolo[1,5-a]pyrimidin-2-amine;
N-[(2,2-Difluoro-2H-1,3-benzodioxol-5-yl)methyl]-5-methyl-7-(oxan-4-yl)-[1,2,4]triazolo[1,5-a]pyrimidin-2-amine;
5-Methyl-N-[(3-methyl-1-phenyl-1H-pyrazol-4-yl)methyl]-7-(oxan-4-yl)-[1,2,4]triazolo[1,5-a]pyrimidin-2-amine;

5-Methyl-N-[(2-methylphenyl)methyl]-7-(oxan-4-yl)-[1,2,4]triazolo[1,5-a]pyrimidin-2-amine;
N-[(2-Chlorophenyl)methyl]-5-methyl-7-(oxan-4-yl)-[1,2,4]triazolo[1,5-a]pyrimidin-2-amine;
N-[(2,5-Difluorophenyl)methyl]-5-methyl-7-(oxan-4-yl)-[1,2,4]triazolo[1,5-a]pyrimidin-2-amine;
N-[(2,6-Difluoro-4-methoxyphenyl)methyl]-5-methyl-7-(oxan-4-yl)-[1,2,4]triazolo[1,5-a]pyrimidin-2-amine;
N-[(2,6-Difluorophenyl)methyl]-5-methyl-7-(oxan-4-yl)-[1,2,4]triazolo[1,5-a]pyrimidin-2-amine;
N-{[2-(Difluoromethyl)pyridin-4-yl]methyl}-5-methyl-7-(oxan-4-yl)-[1,2,4]triazolo[1,5-a]pyrimidin-2-amine;
N-[(2,6-Dimethylpyridin-4-yl)methyl]-5-methyl-7-(oxan-4-yl)-[1,2,4]triazolo[1,5-a]pyrimidin-2-amine;
5-Methyl-N-[(5-methylpyridin-3-yl)methyl]-7-(oxan-4-yl)-[1,2,4]triazolo[1,5-a]pyrimidin-2-amine;
7-(4-Fluorooxan-4-yl)-N-[(4-methoxyphenyl)methyl]-5-methyl-[1,2,4]triazolo[1,5-a]pyrimidin-2-amine;
N-[(3,4-Difluorophenyl)methyl]-5-methyl-7-(oxan-4-yl)-[1,2,4]triazolo[1,5-a]pyrimidin-2-amine;
N-[(4-Fluorophenyl)methyl]-5-methyl-7-(oxan-4-yl)-[1,2,4]triazolo[1,5-a]pyrimidin-2-amine;
N-[(3-Fluorophenyl)methyl]-5-methyl-7-(oxan-4-yl)-[1,2,4]triazolo[1,5-a]pyrimidin-2-amine;
5-Methyl-7-(oxan-4-yl)-N-{[2-(trifluoromethyl)pyridin-4-yl]methyl}-[1,2,4]triazolo[1,5-a]pyrimidin-2-amine;
5-Methyl-7-(oxan-4-yl)-N-(quinolin-4-ylmethyl)-[1,2,4]triazolo[1,5-a]pyrimidin-2-amine;
5-Methyl-N-[(3-methyl-1-phenyl-1H-pyrazol-4-yl)methyl]-7-(4-methyloxan-4-yl)-[1,2,4]triazolo[1,5-a]pyrimidin-2-amine;
5-Methyl-7-(4-methyloxan-4-yl)-N-[(1-phenyl-1H-pyrazol-4-yl)methyl]-[1,2,4]triazolo[1,5-a]pyrimidin-2-amine;
7-Cyclopropyl-5-methyl-N-[(3-methyl-1-phenyl-1H-pyrazol-4-yl)methyl]-[1,2,4]triazolo[1,5-a]pyrimidin-2-amine;
N-[(1R)-1-(4-Methoxyphenyl)ethyl]-5-methyl-7-(oxan-4-yl)-[1,2,4]triazolo[1,5-a]pyrimidin-2-amine;
N-{[1-(2,2-Difluoroethyl)-3-methyl-1H-pyrazol-4-yl]methyl}-5-methyl-7-(oxan-4-yl)-[1,2,4]triazolo[1,5-a]pyrimidin-2-amine;
5-Methyl-N-{[3-methyl-1-(propan-2-yl)-1H-pyrazol-4-yl]methyl}-7-(oxan-4-yl)-[1,2,4]triazolo[1,5-a]pyrimidin-2-amine;
N-[(1-Cyclopentyl-3-methyl-1H-pyrazol-4-yl)methyl]-5-methyl-7-(oxan-4-yl)-[1,2,4]triazolo[1,5-a]pyrimidin-2-amine;
N-[(2,4-Difluorophenyl)methyl]-5-methyl-7-(oxan-4-yl)-[1,2,4]triazolo[1,5-a]pyrimidin-2-amine;
N-[(1 S)-1-(4-Methoxyphenyl)ethyl]-5-methyl-7-(oxan-4-yl)-[1,2,4]triazolo[1,5-a]pyrimidin-2-amine;
N-[(3,5-Difluoropyridin-4-yl)methyl]-5-methyl-7-(oxan-4-yl)-[1,2,4]triazolo[1,5-a]pyrimidin-2-amine;
7-Cyclobutyl-5-methyl-N-[(3-methyl-1-phenyl-1H-pyrazol-4-yl)methyl]-[1,2,4]triazolo[1,5-a]pyrimidin-2-amine;
5-Methyl-N-[(3-methyl-1-phenyl-1H-pyrazol-4-yl)methyl]-7-(oxolan-3-yl)-[1,2,4]triazolo[1,5-a]pyrimidin-2-amine;
4-Fluoro-3-({[5-methyl-7-(oxan-4-yl)-[1,2,4]triazolo[1,5-a]pyrimidin-2-yl]amino}methyl)benzonitrile
5-Methyl-N-[(3-methyl-1-phenyl-1H-pyrazol-4-yl)methyl]-7-(propan-2-yl)-[1,2,4]triazolo[1,5-a]pyrimidin-2-amine;
N-[(4-Methoxyphenyl)methyl]-5-methyl-7-(1-methylcyclopropyl)-[1,2,4]triazolo[1,5-a]pyrimidin-2-amine;
5-Methyl-N-[(3-methyl-1-phenyl-1H-pyrazol-4-yl)methyl]-7-(1-methylcyclopropyl)-[1,2,4]triazolo[1,5-a]pyrimidin-2-amine;
N-[(4-Methoxyphenyl)methyl]-7-(2-methoxypropan-2-yl)-5-methyl-[1,2,4]triazolo[1,5-a]pyrimidin-2-amine;
N-[(3-Chloro-2,4-difluorophenyl)methyl]-5-methyl-7-(oxan-4-yl)-[1,2,4]triazolo[1,5-a]pyrimidin-2-amine;
5-Methyl-N-[(4-methyl-2-phenyl-1,3-oxazol-5-yl)methyl]-7-(oxan-4-yl)-[1,2,4]triazolo[1,5-a]pyrimidin-2-amine;
N-[(5-Chloro-2,4-difluorophenyl)methyl]-5-methyl-7-(oxan-4-yl)-[1,2,4]triazolo[1,5-a]pyrimidin-2-amine;
N-[(3-Bromo-5-fluorophenyl)methyl]-5-methyl-7-(oxan-4-yl)-[1,2,4]triazolo[1,5-a]pyrimidin-2-amine;
5-Methyl-N-[(1-methyl-3-phenyl-1H-pyrazol-5-yl)methyl]-7-(oxan-4-yl)-[1,2,4]triazolo[1,5-a]pyrimidin-2-amine;
N-[(3-Bromo-2-fluorophenyl)methyl]-5-methyl-7-(oxan-4-yl)-[1,2,4]triazolo[1,5-a]pyrimidin-2-amine;
N-[(3-Chloro-5-fluorophenyl)methyl]-5-methyl-7-(oxan-4-yl)-[1,2,4]triazolo[1,5-a]pyrimidin-2-amine;
5-Methyl-N-{[1-methyl-3-(trifluoromethyl)-1H-pyrazol-5-yl]methyl}-7-(oxan-4-yl)-[1,2,4]triazolo[1,5-a]pyrimidin-2-amine;
3-({[5-Methyl-7-(oxan-4-yl)-[1,2,4]triazolo[1,5-a]pyrimidin-2-yl]amino}methyl)benzonitrile;

and pharmaceutically acceptable salts thereof.

16. A compound selected from the group consisting of:

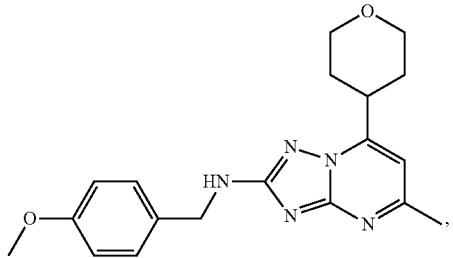

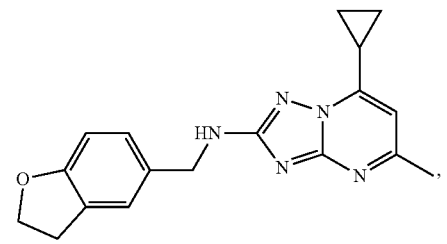

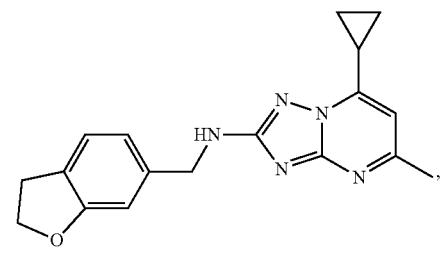

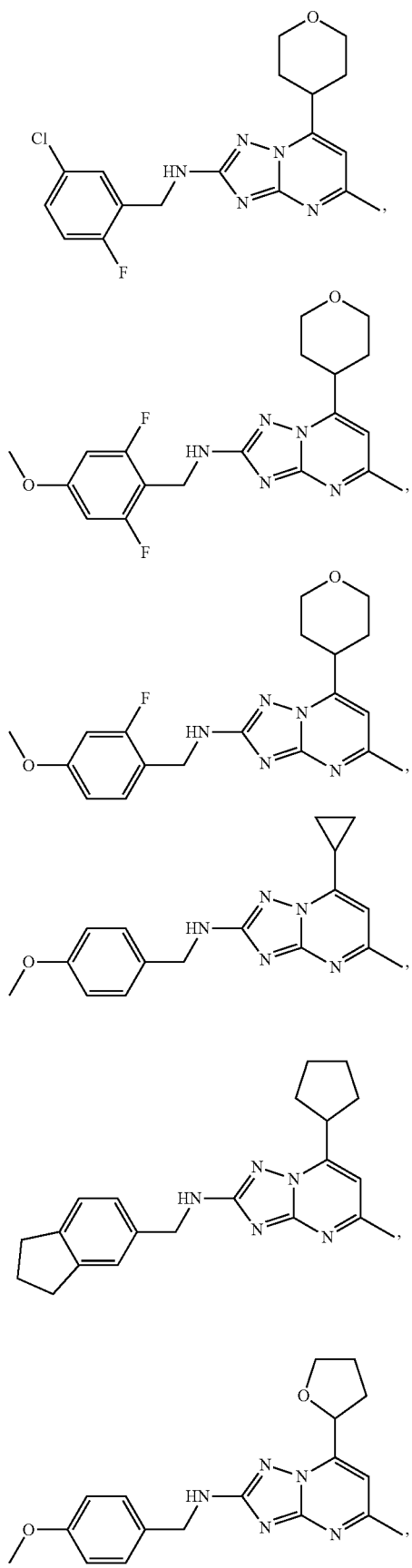
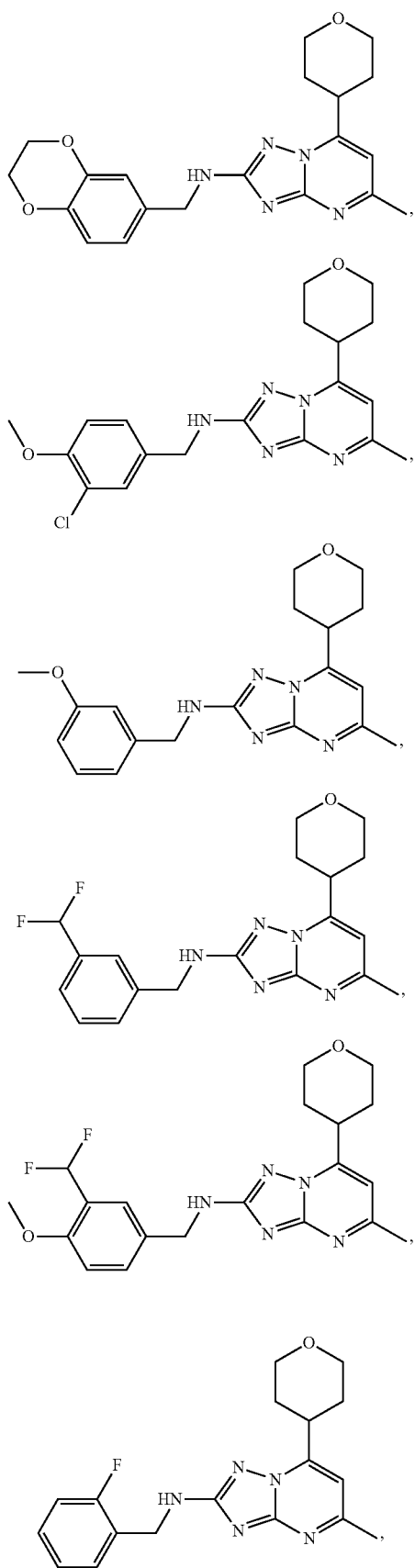

111
-continued
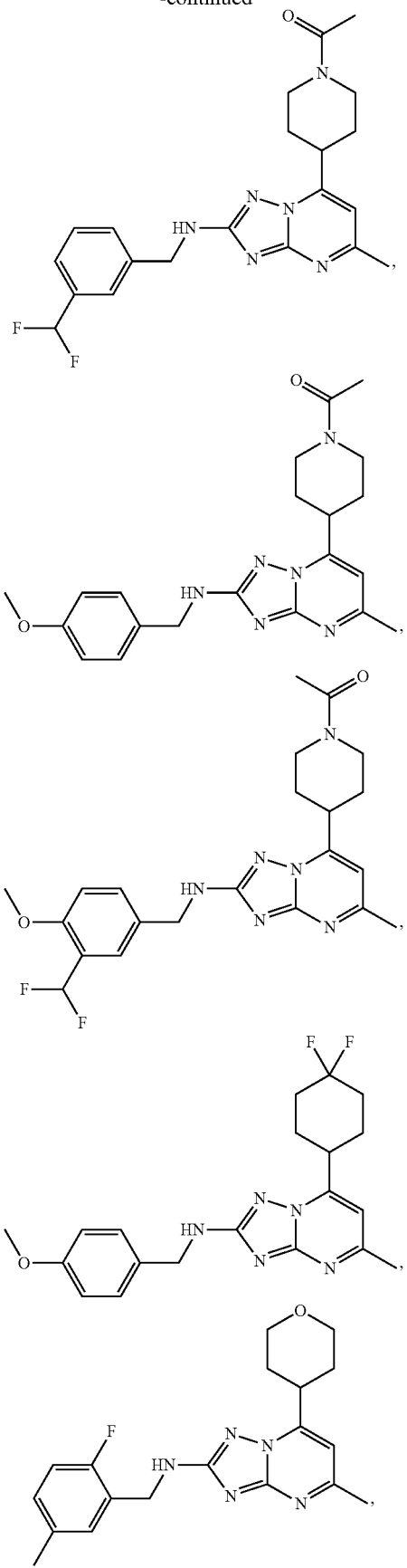
112
-continued
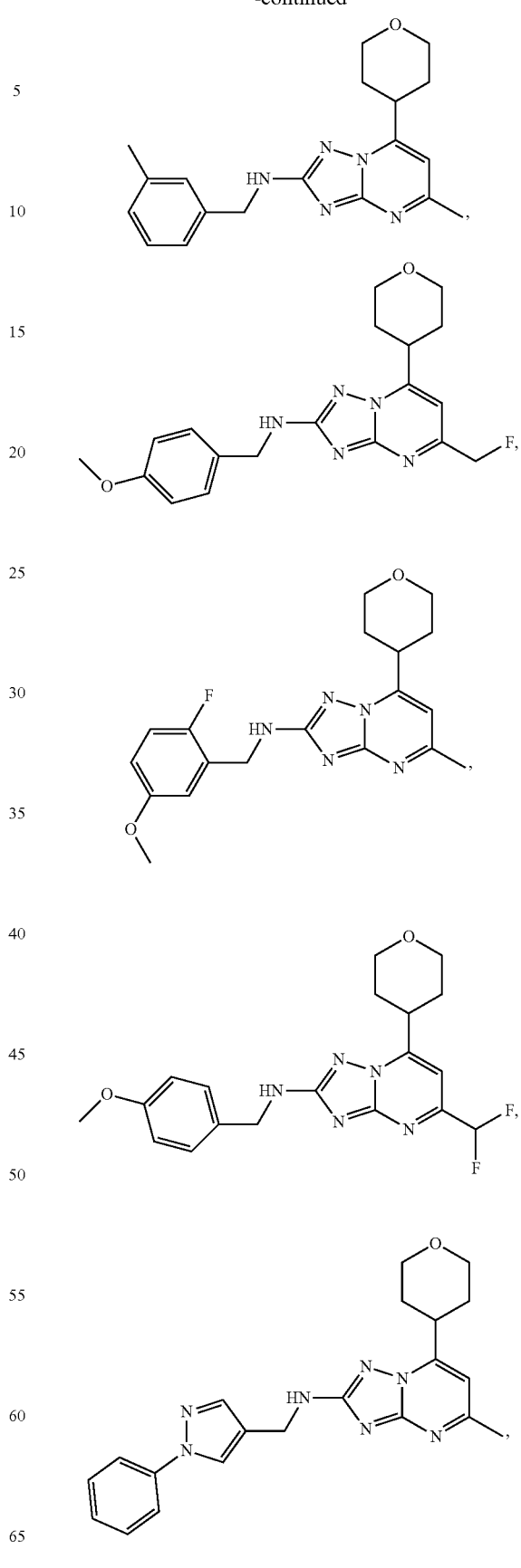

113
-continued
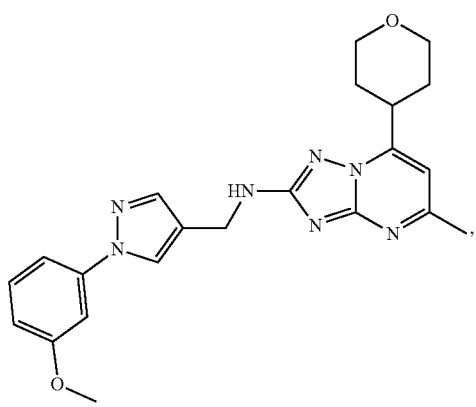
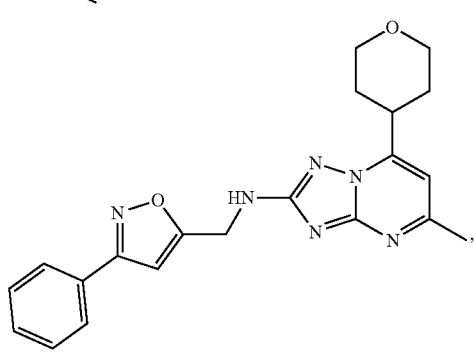
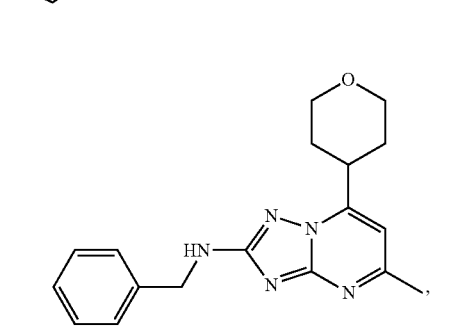
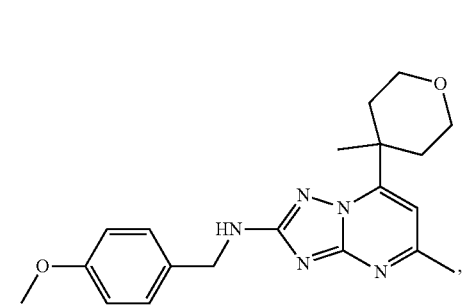
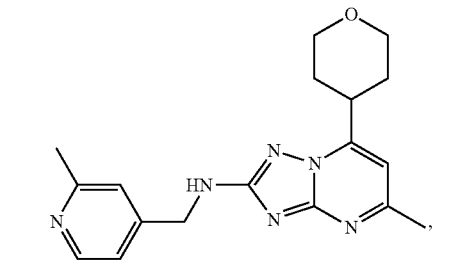
114
-continued
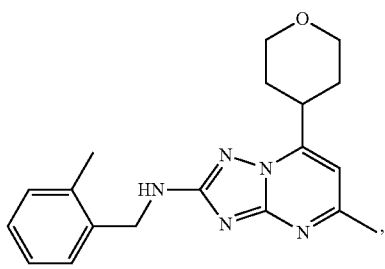
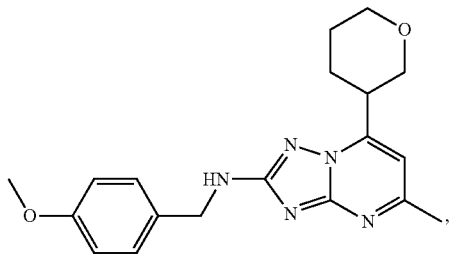
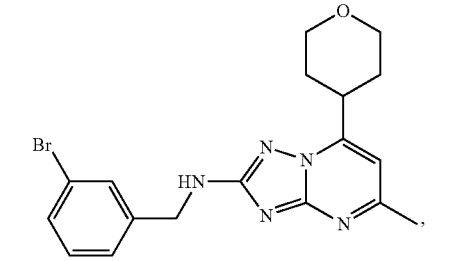
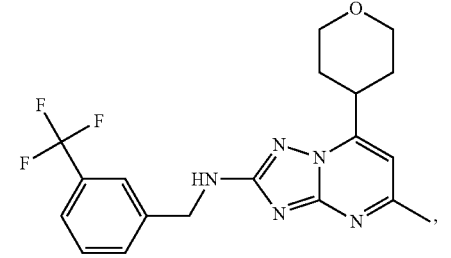
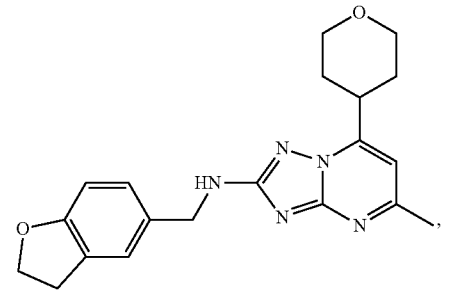
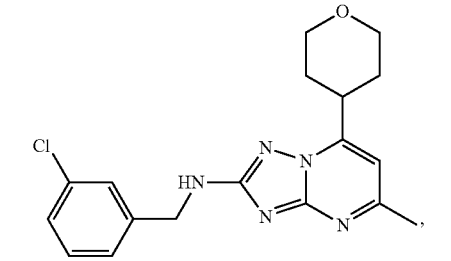

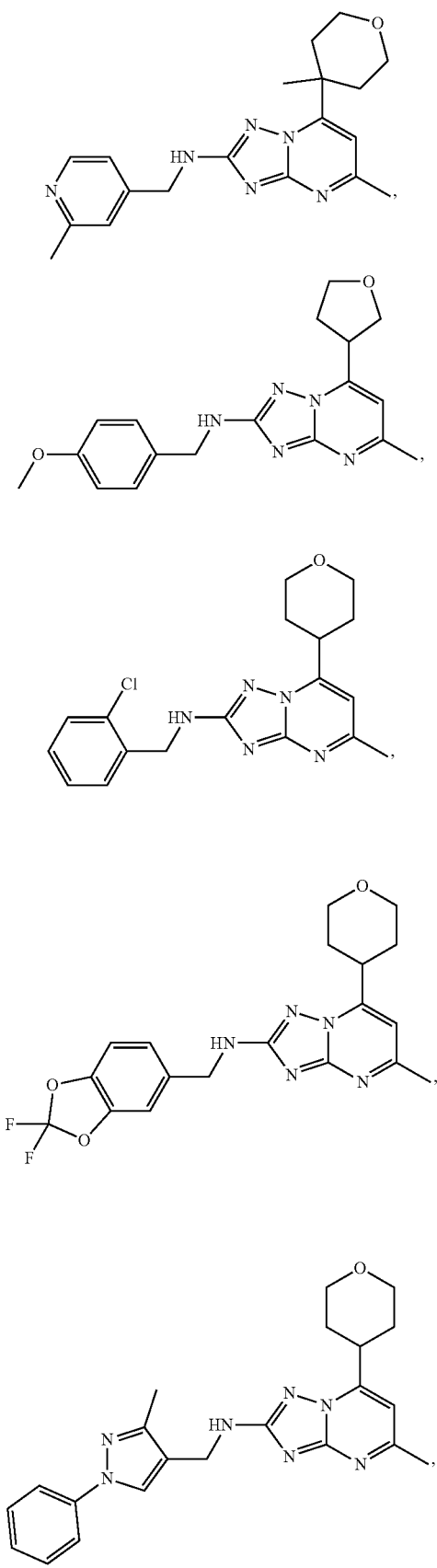
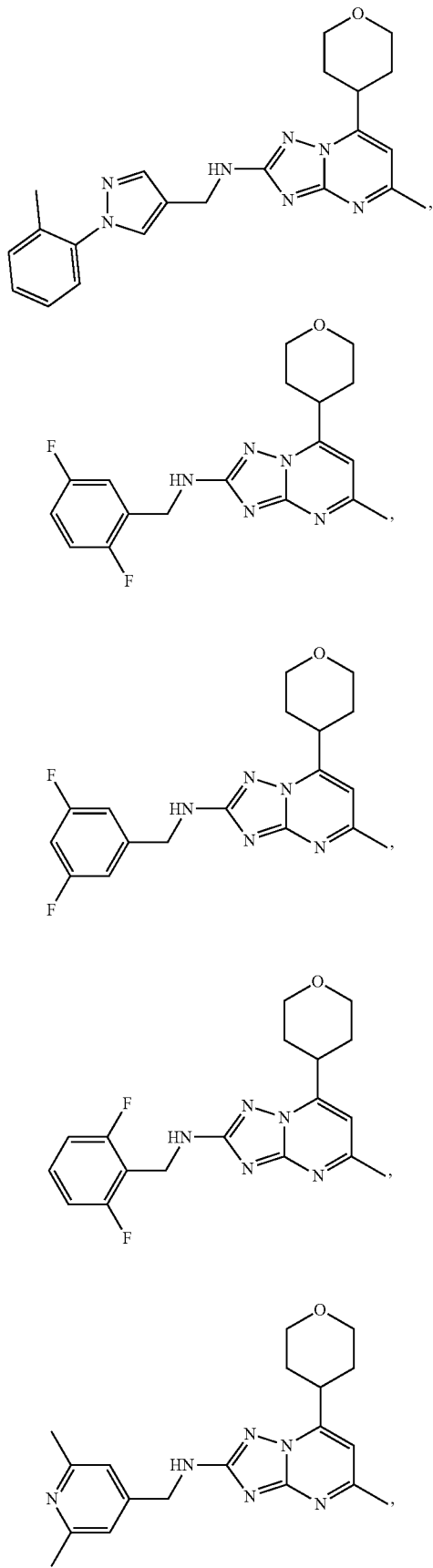

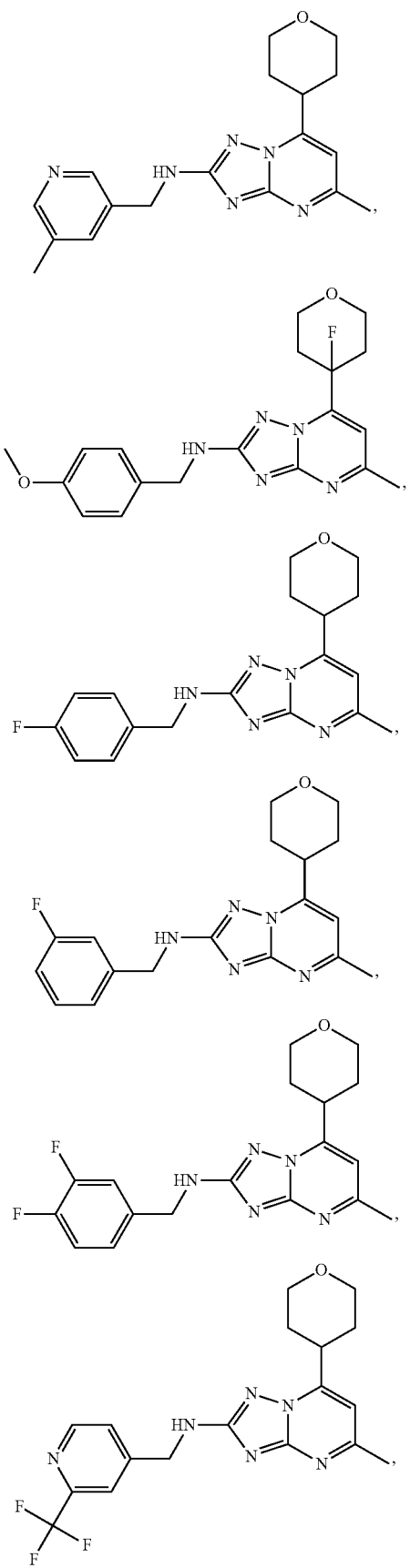
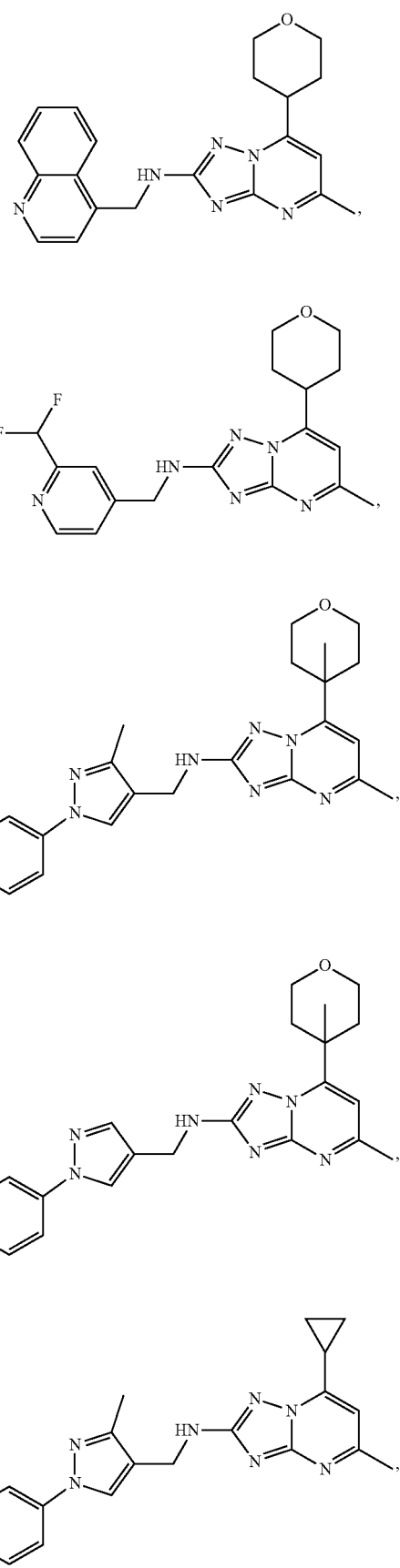

119
-continued
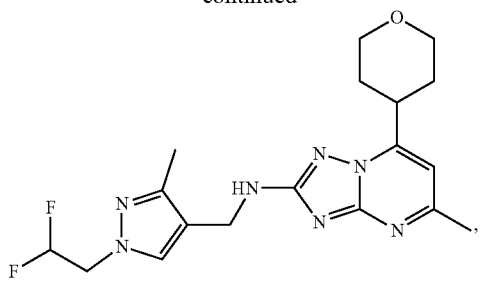
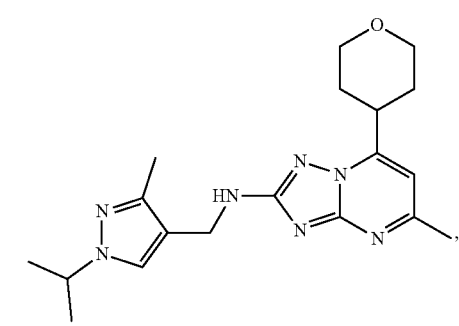
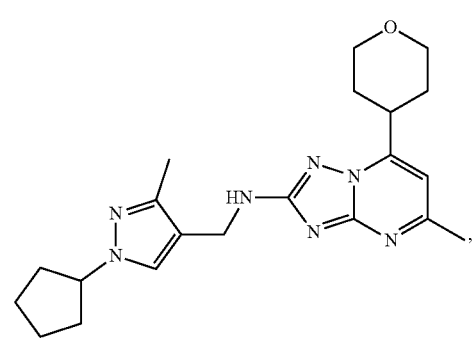
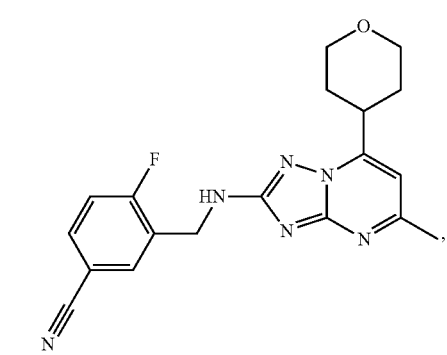
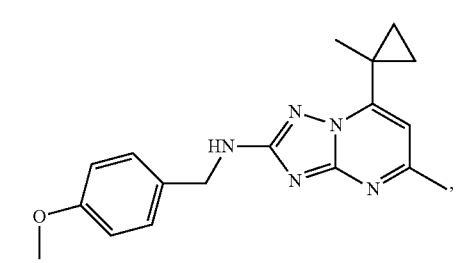
120
-continued
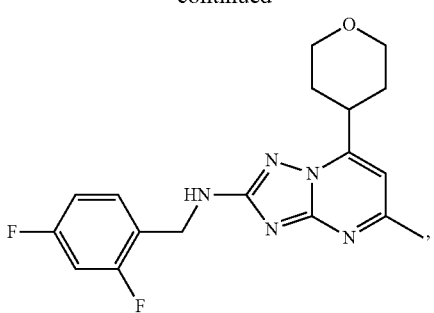
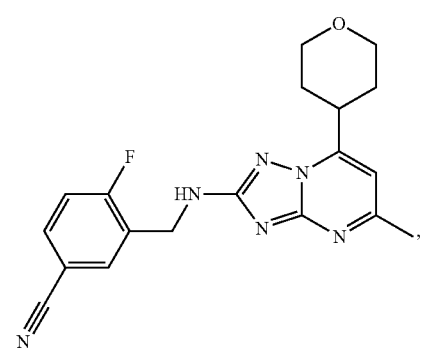
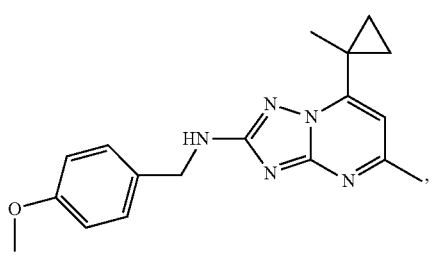
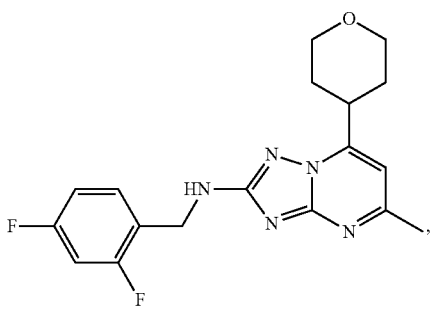
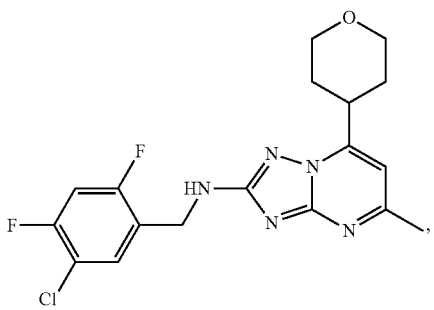

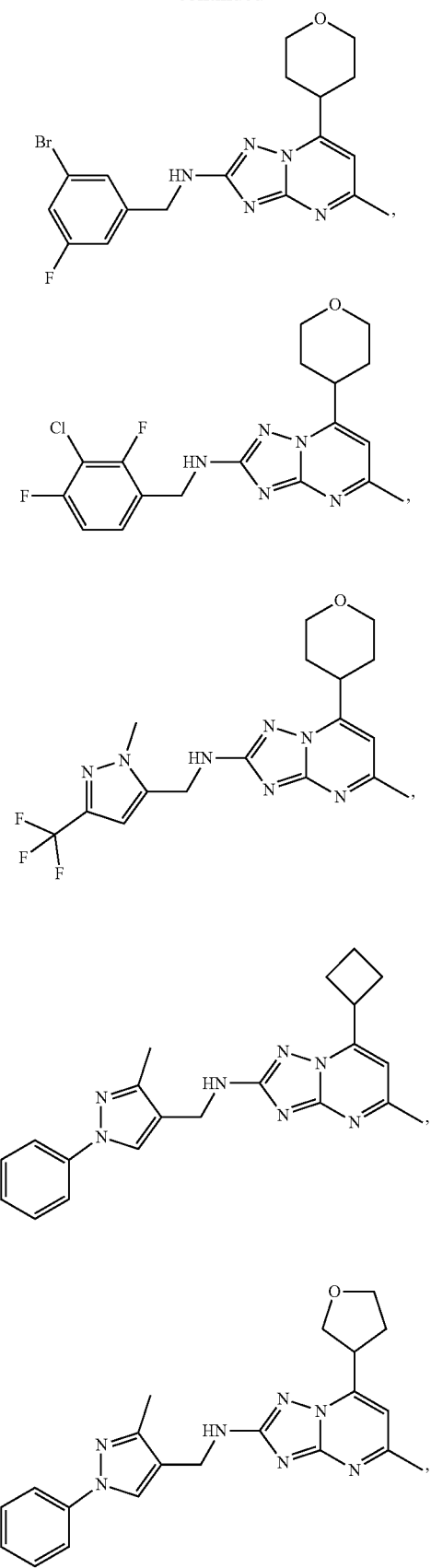
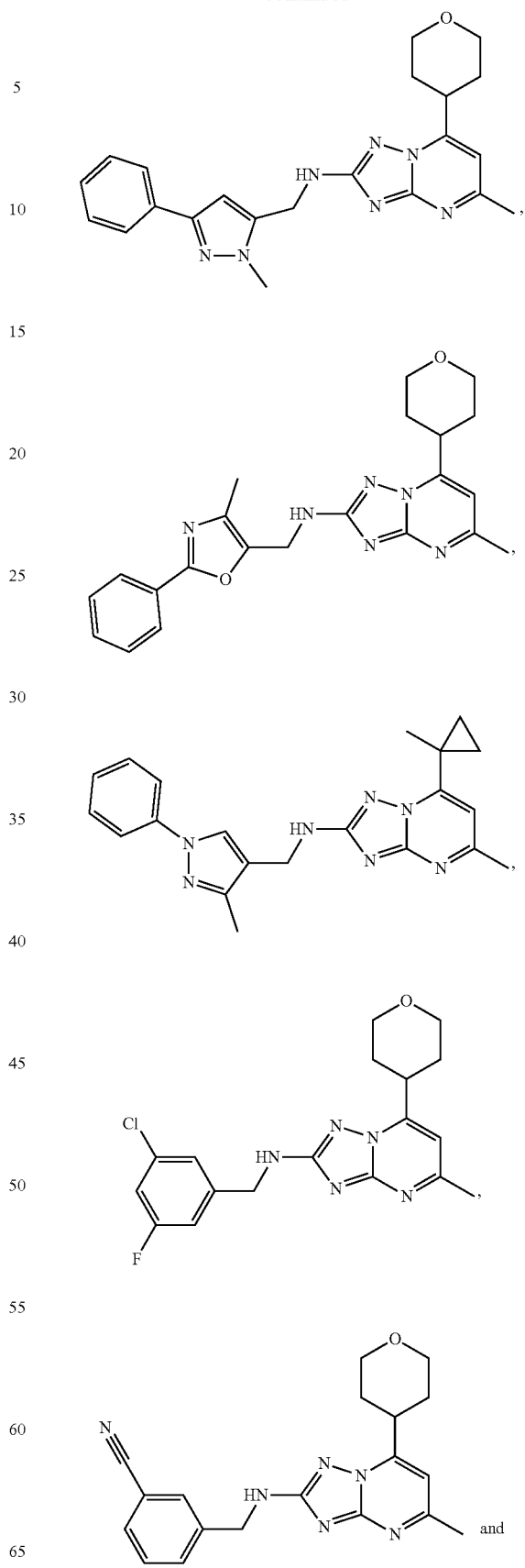

-continued

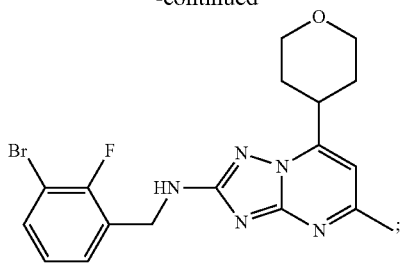

and pharmaceutically acceptable salts thereof.

17. A pharmaceutical composition comprising: a pharmaceutically acceptable excipient; and a therapeutically effective amount of at least one compound of claim 1.

18. A pharmaceutical composition comprising: a pharmaceutically acceptable excipient; and a therapeutically effective amount of at least one compound of claim 15.

19. A method of modulating PDE2 in a subject having a neurological disorder, comprising administering to a subject in need thereof an effective amount of a compound of claim 1, wherein the neurological disorder is selected from the group consisting of a central nervous system (CNS) disorder, a developmental disorder; a schizophrenia spectrum or psychotic disorder; a depressive disorder; an anxiety disorder; an obsessive-compulsive disorder; a dissociative disorder; a disruptive, impulse-control, or conduct disorder; a trauma- or stressor-related disorder; a feeding or eating disorder; a sleep-wake disorder; a sexual disorder; a substance-related or addictive disorder; and a personality disorder.

20. A method of modulating PDE2 in a subject having a neurological disorder, comprising administering to a subject in need thereof an effective amount of a compound of claim 1, wherein the neurological disorder is an acquired disorder selected from the group consisting of delirium, dementia, an age-associated cognitive deficit, a trauma-dependent loss of function, and a cognitive impairment due to chemotherapy.

* * * * *